(12) United States Patent
Holten-Andersen et al.

(10) Patent No.: US 11,590,207 B2
(45) Date of Patent: *Feb. 28, 2023

(54) DOSAGE REGIMEN FOR A CONTROLLED-RELEASE PTH COMPOUND

(71) Applicant: Ascendis Pharma Bone Diseases A/S, Hellerup (DK)

(72) Inventors: Lars Holten-Andersen, Vanløse (DK); Kennett Sprogøe, Holte (DK); David Brian Karpf, Mountain View, CA (US)

(73) Assignee: ASCENDIS PHARMA BONE DISEASES A/S, Hellerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/337,713

(22) PCT Filed: Sep. 28, 2017

(86) PCT No.: PCT/EP2017/074592
§ 371 (c)(1),
(2) Date: Mar. 28, 2019

(87) PCT Pub. No.: WO2018/060310
PCT Pub. Date: Apr. 5, 2018

(65) Prior Publication Data
US 2020/0023041 A1  Jan. 23, 2020

(30) Foreign Application Priority Data

Sep. 29, 2016 (EP) .................... 16191451
Feb. 13, 2017 (EP) .................... 17155843

(51) Int. Cl.
| | | |
|---|---|---|
| A61K 38/29 | (2006.01) | |
| A61K 47/60 | (2017.01) | |
| A61K 9/00 | (2006.01) | |
| A61K 9/16 | (2006.01) | |
| A61K 47/34 | (2017.01) | |

(52) U.S. Cl.
CPC ........... *A61K 38/29* (2013.01); *A61K 9/0019* (2013.01); *A61K 9/1647* (2013.01); *A61K 47/60* (2017.08); *A61K 47/34* (2013.01)

(58) Field of Classification Search
CPC ........ A61K 38/29; A61K 47/30; A61K 47/34; A61K 47/50; A61K 47/56; A61K 47/60; C07K 14/635; C07K 17/00; C07K 17/08
See application file for complete search history.

(56) References Cited

U.S. PATENT DOCUMENTS

| | | | |
|---|---|---|---|
| 5,567,439 A * | 10/1996 | Myers | A23G 3/10 424/439 |
| 5,744,444 A | 4/1998 | Forssmann et al. | |
| 7,585,837 B2 | 9/2009 | Shechter et al. | |
| 7,820,179 B2 * | 10/2010 | Brown-Augsburger | C07K 14/635 424/198.1 |
| 8,101,729 B2 * | 1/2012 | Niemczyk | C07D 207/404 530/323 |
| 8,618,124 B2 | 12/2013 | Greenwald et al. | |
| 8,754,190 B2 | 6/2014 | Ashley et al. | |
| 8,865,220 B2 * | 10/2014 | Ho | A61K 9/1647 424/497 |
| 8,906,847 B2 | 12/2014 | Cleemann et al. | |
| 8,946,405 B2 | 2/2015 | Ashley et al. | |
| 10,980,860 B2 | 4/2021 | Vetter et al. | |
| 2003/0166581 A1 * | 9/2003 | Almarsson | C07H 5/04 514/23 |
| 2005/0124537 A1 * | 6/2005 | Kostenuik | C07K 14/635 530/300 |

(Continued)

FOREIGN PATENT DOCUMENTS

| | | |
|---|---|---|
| CN | 1597697 A | 3/2005 |
| CN | 1739795 | 3/2006 |

(Continued)

OTHER PUBLICATIONS

Winer et al. Long-Term Treatment of Hypoparathyroidism: A Random Controlled Study Comparing Parathyroid Hormone-(1-34) Versus Calcitrol and Calcium. The Journal of Clinical Endocrinology & Metabolism. Sep. 2003, vol. 88, No. 9, pp. 4214-4220. (Year: 2003).*
Arrighi I. et al. "Bone Healing Induced by Local Delivery of an Engineered Parathyroid Hormone Prodrug" Biomaterials, Jan. 4, 2009, 1763-1771, 30.
Bowie et al., "Deciphering the Message in Protein Sequences: Tolerance to Amino Acid Substitutions", Science, (1990), 1306-1310, 247.
Products list of JenKem Technology, USA (accessed by download from http://www.jenkemusa.com/Pages/PEGProducts.aspx on Dec. 18, 2014).

(Continued)

*Primary Examiner* — Jeffrey E. Russel
(74) *Attorney, Agent, or Firm* — Alston & Bird LLP

(57) ABSTRACT

The present invention relates to a pharmaceutical composition comprising at least one controlled-release PTH compound or a pharmaceutically acceptable salt, hydrate or solvate thereof, for use in the treatment, control, delay or prevention of a condition that can be treated, controlled, delayed or prevented with PTH, pharmaceutical composition comprising at least one controlled-release PTH compound or a pharmaceutically acceptable salt, hydrate or solvate thereof, for use in the treatment, control, delay or prevention of a condition that can be treated, controlled, delayed or prevented with PTH, wherein said pharmaceutical composition is administered no more frequently than once every 24 hours with a dosage of the controlled-release PTH compound that corresponds to no more than 70% of the molar equivalent dose of PTH 1-84 administered every 24 hours required to maintain serum calcium within normal levels over said 24 hour period in humans.

5 Claims, No Drawings

Specification includes a Sequence Listing.

(56) References Cited

U.S. PATENT DOCUMENTS

| | | | |
|---|---|---|---|
| 2005/0148763 A1* | 7/2005 | Sekimori | A61K 38/29 530/399 |
| 2006/0045912 A1* | 3/2006 | Truog | A61P 7/06 424/468 |
| 2006/0069021 A1 | 3/2006 | Costantino et al. | |
| 2010/0129341 A1 | 5/2010 | Sakon et al. | |
| 2011/0112021 A1 | 5/2011 | Rau et al. | |
| 2011/0195900 A1 | 8/2011 | Schteingart et al. | |
| 2011/0229580 A1* | 9/2011 | Srivastava | A61K 9/1652 424/493 |
| 2011/0305766 A1 | 12/2011 | Ho et al. | |
| 2012/0035101 A1 | 2/2012 | Fares et al. | |
| 2012/0040320 A1* | 2/2012 | Nadeau | G09B 23/285 434/262 |
| 2013/0116180 A1* | 5/2013 | Gardella | A61K 38/29 514/11.8 |
| 2013/0183349 A1 | 7/2013 | Ho et al. | |
| 2014/0011739 A1* | 1/2014 | Klatzmann | A61K 47/42 514/5.9 |
| 2014/0248365 A1* | 9/2014 | Rademacher | A61K 9/146 424/491 |
| 2015/0065423 A1* | 3/2015 | Laulicht | A61K 45/06 514/6.3 |
| 2015/0290337 A1 | 10/2015 | Vetter et al. | |
| 2016/0264636 A1* | 9/2016 | Rebollo Garcia | C07K 14/4703 |
| 2019/0224329 A1 | 7/2019 | Sprogøe et al. | |
| 2019/0282668 A1* | 9/2019 | Sprogoe | A61P 5/18 |
| 2020/0046725 A1 | 2/2020 | Cleeman et al. | |
| 2020/0276270 A1 | 9/2020 | Holten-Anderson et al. | |
| 2020/0276276 A1 | 9/2020 | Sprogøe et al. | |
| 2020/0360487 A1 | 11/2020 | Sprogøe et al. | |
| 2020/0360488 A1* | 11/2020 | Sprogoe | A61K 9/00 |
| 2020/0376089 A1 | 12/2020 | Sprogøe et al. | |
| 2021/0196801 A1 | 7/2021 | Sprogøe et al. | |
| 2022/0008516 A1 | 1/2022 | Cleemann et al. | |
| 2022/0088149 A1 | 3/2022 | Skands et al. | |

FOREIGN PATENT DOCUMENTS

| | | | |
|---|---|---|---|
| EP | 1 477 496 A1 | 11/2001 | |
| EP | 1 536 334 | 6/2005 | |
| EP | 1534334 B1 | 6/2014 | |
| WF | 0920873 A2 | 6/1999 | |
| WO | WO 02/089789 | 11/2002 | |
| WO | WO 2003/064462 A1 | 8/2003 | |
| WO | WO 2005/027978 | 3/2005 | |
| WO | WO 2005/099768 | 10/2005 | |
| WO | WO 2005/099768 A2 | 10/2005 | |
| WO | WO 2005/115441 A2 | 12/2005 | |
| WO | WO 2006/003014 | 1/2006 | |
| WO | WO 2006/136536 A2 | 12/2006 | |
| WO | WO 2006/136586 | 12/2006 | |
| WO | WO 2007/106597 A3 | 9/2007 | |
| WO | WO 2008/034122 | 3/2008 | |
| WO | WO 2008/048784 A1 | 4/2008 | |
| WO | WO 2008/155134 | 12/2008 | |
| WO | WO 2009/009712 | 1/2009 | |
| WO | WO 2009/009712 A1 | 1/2009 | |
| WO | WO 2009/053106 A1 | 4/2009 | |
| WO | WO 2009/095479 | 8/2009 | |
| WO | WO 2009/095479 A1 | 8/2009 | |
| WO | WO 2009/143412 | 11/2009 | |
| WO | WO 2009/156481 A1 | 12/2009 | |
| WO | WO 2010/091122 | 8/2010 | |
| WO | WO 2011/012715 | 2/2011 | |
| WO | WO 2011/012715 A1 | 2/2011 | |
| WO | WO 2011/012718 A1 | 2/2011 | |
| WO | WO 2011/012719 | 2/2011 | |
| WO | WO 2011/012719 A1 | 2/2011 | |
| WO | WO 2011/012721 | 2/2011 | |
| WO | WO 2011/012722 | 2/2011 | |
| WO | WO 2011/012722 A1 | 2/2011 | |
| WO | WO 2011/012723 | 2/2011 | |
| WO | WO 2011/042450 | 4/2011 | |
| WO | WO 2011/039215 A1 | 7/2011 | |
| WO | WO 2011/039216 A1 | 7/2011 | |
| WO | WO 2011/082368 | 7/2011 | |
| WO | WO 2011/082368 A2 | 7/2011 | |
| WO | WO 2011/089214 | 7/2011 | |
| WO | WO 2011/089215 | 7/2011 | |
| WO | WO 2011/089216 | 7/2011 | |
| WO | WO 2011/123813 | 10/2011 | |
| WO | WO 2011/144756 | 11/2011 | |
| WO | WO 2012/002047 | 1/2012 | |
| WO | WO 2012/035139 A1 | 3/2012 | |
| WO | WO 2013/024048 | 2/2013 | |
| WO | WO 2013/024049 | 2/2013 | |
| WO | WO 2013/024051 | 2/2013 | |
| WO | WO 2013/024052 | 2/2013 | |
| WO | WO 2013/024053 | 2/2013 | |
| WO | WO 2013/024053 A1 | 2/2013 | |
| WO | WO 2013/036857 | 3/2013 | |
| WO | WO 2013/053856 | 4/2013 | |
| WO | WO 2013/160340 | 10/2013 | |
| WO | WO 2014/033540 | 3/2014 | |
| WO | WO 2014/056915 | 4/2014 | |
| WO | WO 2014/056923 | 4/2014 | |
| WO | WO 2014/056926 | 4/2014 | |
| WO | WO 2014/060512 | 4/2014 | |
| WO | WO 2014/086961 | 6/2014 | |
| WO | WO 2014/173759 | 10/2014 | |
| WO | WO 2015/052155 | 4/2015 | |
| WO | WO 2016/020373 | 2/2016 | |
| WO | WO 2016/020373 A1 | 2/2016 | |
| WO | WO 2016/065042 A1 | 4/2016 | |
| WO | WO 2016/110577 | 7/2016 | |
| WO | WO 2017/148883 | 9/2017 | |
| WO | WO-2017148883 A1 * | 9/2017 | A61K 47/60 |
| WO | WO 2013/060310 A1 | 4/2018 | |
| WO | WO 2013/060311 A1 | 4/2018 | |
| WO | WO 2018/060312 A1 | 4/2018 | |
| WO | WO-2018060312 A1 * | 4/2018 | A61K 47/34 |
| WO | WO 2018/100174 A1 | 6/2018 | |
| WO | WO 2019/219896 A1 | 11/2019 | |
| WO | WO 2020/165087 A1 | 8/2020 | |

OTHER PUBLICATIONS

Elsie Watchorn, "CCLV. The Normal Serum-Calcium and Magnesium of the Rat: Their Relation to Sex and Age", Biochemical Laboratory, Cambridge, Nov. 1, 1933, 1875-1787.

Wei et al., "The release profiles and bioactivity of parathyroid hormone from poly(lactic-co-glycolic acid) microspheres", Biomaterials, Elsevier Science Publishers BV., Barking, GB, Jan. 1, 2004, 345-352, 25(2) XP004469625.

U.S. Appl. No. 17/428,608, filed Aug. 4, 2021, Skands et al.

U.S. Appl. No. 17/488,137, filed Sep. 28, 2021, Sprogøe et al.

Abate, et al., "Review of Hypoparathyroidism," Frontiers Endocrimolgy, vol. 7, (Jan. 2017).

Aouchiche, et al., "Teriparatide administration by the Omnipod pump: preliminary experience from two cases with refractory hypoparathyroidism," Endocrine, 76:179-188, (2022).

Beauchamp, et al., "A New Procedure for the Synthesis of Polyethylene Glycol-Protein Aducts; Effects on Functin Receptor Recognition, and clearance of Superoxide Dismutase, Lactoferrin, and α2-Macroglobulin," Analytical Biochemistry, 131, 25-33, (1983).

Bilezikean, et al., "Management of Hypoparathyroidism: Present and Future," J Clin Endocrinol Metab, 101(6):2313-2324, (Jun. 2016).

Chamow, et al., "Modification of CD4 Immunoadhesin with Monomethoxypoly(ethylene glycol) Aldehyde via Reductive Alkylation," Bioconjugate Chem. 5, 133-140, (1994).

Dyson, et al., "May's Chemistry of Synthetic Drugs," Longmans, Greens and Co., Ltd., 5th edition, May 1959, 1-20.

Filpula, et al., "Releasable PEGylation of proteins with customized linkers", Nov. 30, 2007, 29-49, 60(1), Advanced drug delivery reviews, Elsevier, Amsterdam, NL.

Finkelstein, et al., "Effects of Teriparatide Retreatment in Osteoporotic Men and Women," J. Clin Endocrinol Metab, 94(7), 2495-2501, (Jul. 2009).

(56) References Cited

OTHER PUBLICATIONS

Florence, et al., Attwood D. Physicochemical principles of pharmacy. 3rd ed.—1998—Easton, Bristol: Aarontype Limited, pp. 18-21, paragraph 1.4.1.
Gafni, et al., "Daily Parathyroid Hormone 1-34 Replacement Therapy for Hypoparathyroidism Induces Marked Changes in Bone Turnover and Structure," Journal of Bone and Mineral Research, vol. 27, No. 8, pp. 1811-1820, (Aug. 2012).
Hohenstein, et al., "Development and validation of a novel cell-based assay for potency determination of human parathyroid honnone (PM)", Journal of Pharmaceutical and Biomedical Analysis, Sep. 2014, 345¬350, 98.
Holten-Anderson, et al., "Design and Preclinical Development of TransCon PTH, an Investigational Sustained-Release PTH Replacement Therapy for Hypoparathyroidism," J Bone Miner Res, doi: 10.1002/jbmr.3824, (2019).
Jakubke, et al., "Amioacids, peptides and proteins," M. Mir Publishers, p. 456 (partial English translation of D6) (1985).
Karpf, et al., "A Randomized Double-Blind Placebo-Controled First-In-Human Phase 1 Trial of TransCon PTH in Healthy Adults," Journal of Bone and Mineral Research, Vo. 35, No. 8, pp. 1430-1440, (Aug. 2020).
Khan, et al., "Path Forward: A Randomized, Double-Blind Placebo-Controlled Phase 2 Trial of TransCon PTH in Adult Hypoparathyroidism," The Journal of Clinical Endocrinology & Metabolism, vol. XX, No. XX, 1014, (2021).
Kostenuik, et al., "Infrequent Delivery of a Long-Acting PTH-Fc Fusion Protein Has Potent Anabolic Effects on Cortical and Cancellous Bone", Journal of Bone and Mineral Research, 2007, 1534-1547, 22(10).
Levine, et al., "Intrinsic bioconjugation for site-specific protein PEGylation at N-terminal serine", Chemical Communications—Chemcom, Jan. 1, 2014, 6909-6912, 50 (52), XP055305086.
Liu, et al., "PEGylation Site-Dependent Structural Heterogeneity Study of MonoPEGylated Human Parathyroid Hormone Fragment hPTH(1-34)" Langmuir, Sep. 30, 2014, 11421-11427, 30(38), XP05505083.
Mannstadt, et al., "Efficacy and safety of recombinant human parthyroid hormone (1-84) in hypoparathyroidism (REPLACE): a double-blind, placebo-controlled, randomised, phase 3 study," Lancet Diabetes Endocrinol, 1: 275-283, (2013).
Mannstadt, et al., "Safety and Efficacy of 5 Years of Treatment with Recombinant Human Parathyroid Hormone in Adults with Hypoparathyroidism," J Clin Endocrinol Metab, 104(11):5136-5147, (2019).
Maschkowskij, et al., "Maschkowskij M.D. Drugs," M. New Wave Publishers, The Sixteenth Edition, 2012-2016,, (Partial English Translation of D5).
Mitchell, et al., "Long-Term Follow-Up of Patients with Hypoparathyroidism," J Clin Endocrinol Metab, 97: 4507-4514, (2012).
Na, et al., "Capillary electrophoretic characterization of PEGylated human parathyroid hormone with matrix-assisted laser desorption/ionization time-of-flight mass spectrometry", Analytical Biochemistry, Aug. 15, 2004, 322-328, 331(2), Elsevier, Amsterdam, NL.
NOF Corporation Catalog, NOF Corporation, Drug Delivery Systems Catalogue, Ver. 8, 60 pages, (Apr. 2006).
Pekkolay, et al., "Alternative treatment of resistant hypoparathyroidism by intermittent infusion of teriparatide using an insulin pump: A case report," Turk J Phys Med Rehab, 65(2):198-201, (2019).
Ponnapakkam, et al., "Treating osteoporosis by targeting parathyroid hormone to bone" Drug Discov Today, Mar. 2014, 204-208, 19(3).
Rejnmark, et al., "PTH replacement therapy of hypoparathyroidism", Bone, Dept. of Endocrinology and Internal Medicine, Aarhus University Hospital, Aarhus, Denmark, May 1, 2012, 50, XP028922570.
Sikjaer, et al., "Effects of PTH(1-84) therapy on muscle function and quality of life in hypoparathyroidism: results from a randomized controlled trial," Osteoporos Int, 25:1717-1726, (2014).
Sikjaer, et al., "The Effect of Adding PTH(1-84) to onventional Treatment of Hypoparathyroidism: A Randomized, Placebo-Controlled Study," Journal of Bone and Mineral Research, vol. 26, No. 10, pp. 2358-2370, (Oct. 2011).
Smith, et al., "Relevance of Half-Life in Drug Design," J. Med. Chem., 61, 4273-4282, (2018).
Thiruchelvam, et al., "Teriparatide Induced Delayed Persistent Hypecalcemia," Case Reports in Endocrinology, vol. 2014, Article IDS 802473, (2014).
Vilardaga, "Molecular basis of parathyroid hormone receptor signaling and trafficking: a family B GPCR paradigm," Cell Mol. Life, Sci., 68(1): 1-13, (2011).
Vokes, et al., "Reombinant Human Parathyroid Hormone Effect on Health-Related Quality of Life in Adults With Chronic Hypoparathyroidism," J Clin Endocrinol Metab, 103: 722-731, (2018).
Winer, et al., "Effects of Pump versus Twice-Daily Injection Delivery of Synthetic Parathyroid Hormone 1-34 in Children with Severe congenital Hypoparathyroidism", J Pediatr., 2014, 556-563, 165(3), NIH, Bethesda, Maryland.
Winer, et al., "Synthetic Human Parathyroid Hormone 1-34 Replacement Therapy: A Randomized Crossover Trial Comparing Pumb Versus Injections in the Treatment of Chronic Hypoparathyroidism," J Clin Endocrinol Metab, 97(2):391-399, (2012).
Winer, et al., Synthetic Human Parathyroid Hormone 1-34 vs Calcitriol and Calcium in the Treatment of Hypoparathyroidism, JAMA, 276:631-636, (1996).
Wu, et al., "Disruption of YPSI and PEP4 genes reduces proteolytic degration of secreted HSA/PTH in Pichia pastoris GS115," J. Ind Microbiol Biotechnol., 40:589-599, (2013).
Zhang, et al., "Molecular-Target-Bsed Anticancer Photosensitizer: Synthesis and in vitro Photodynamic Activity of Erlotinib-Zinc(II) Phthalocyanine Conjugates," ChemMedChem, 10. 312-320, (2015).
U.S. Appl. No. 16/118,155, Non-Final Office Action dated Feb. 11, 2021.
U.S. Appl. No. 16/118,155, Requirement for Restriction/Election dated Oct. 7, 2020.
U.S. Appl. No. 16/337,803, Final Office Action dated May 3, 2021.
U.S. Appl. No. 16/337,803, Non-Final Office Action dated Jan. 12, 2021.
U.S. Appl. No. 16/337,803, Non-Final Office Action dated Mar. 7, 2022.
U.S. Appl. No. 16/337,803, Requirement for Restriction/Election dated Jun. 10, 2020.
U.S. Appl. No. 16/337,955, Final Office Action dated Jan. 7, 2022.
U.S. Appl. No. 16/337,955, Final Office Action dated Apr. 15, 2022.
U.S. Appl. No. 16/337,955, Non-Final Office Action dated Jul. 16, 2020.
U.S. Appl. No. 16/337,955, Non-Final Office Action dated Sep. 7, 2021.
U.S. Appl. No. 16/988,302, Requirement for Restriction/Election dated Jan. 14, 2022.
U.S. Appl. No. 16/989,225, Non-Final Office Action dated Sep. 7, 2021.
U.S. Appl. No. 16/989,225, Requirement for Restriction/Election dated May 14, 2021.
U.S. Appl. No. 17/488,137, Non-Final Office Action dated Feb. 4, 2022.
U.S. Appl. No. 17/488,137, Requirement for Restriction/Election dated Nov. 9, 2021.
U.S. Appl. No. 16/118,155, Final Office Action dated Sep. 28, 2018.
U.S. Appl. No. 16/337,955 Advisory Action dated Feb. 16, 2021.
U.S. Appl. No. 16/337,955 Final Office Action dated Dec. 3, 2020.
WIPO Application No. PCT/EP2017/054550, PCT International Preliminary Report on Patentability dated Sep. 4, 2018.
WIPO Application No. PCT/EP2017/054550, PCT International Search Report and Written Opinion of the International Searching Authority dated Sep. 8, 2017.
WIPO Application No. PCT/EP2017/074592, PCT International Preliminary Report on Patentability dated Apr. 2, 2019.
WIPO Application No. PCT/EP2017/074592, PCT International Search Report and Written Opinion of the International Searching Authority dated Apr. 5, 2018.

(56) References Cited

OTHER PUBLICATIONS

WIPO Application No. PCT/EP2017/074594, PCT International Preliminary Report on Patentability dated Apr. 2, 2019.
WIPO Application No. PCT/EP2017/074594, PCT International Search Report and Written Opinion of the International Searching Authority dated Apr. 5, 2018.
WIPO Application No. PCT/EP2019/062773, PCT International Preliminary Report on Patentability dated Nov. 24, 2020.
WIPO Application No. PCT/EP2019/062773, PCT International Search Report and Written Opinion of the International Searching Authority dated Nov. 21, 2019.
WIPO Application No. PCT/EP2020/053316, PCT International Search Report and Written Opinion of the International Searching Authority dated Sep. 4, 2020.
Cuchert, et al., "Summary Report: Indirect comparisons Mehtods and validity," HAS Department of Medecines Assessment, 66 pages, (Jul. 2009).
Horwitz, et al., "A 7-Day Continuous Infusion of PTH or PTHrP Suppresses Bone Fromation and Uncouples Bone Turnover," Journal of Bone and Mineral Research, vol. 26, No. 9, pp. 2287-2297, (Sep. 2011).
Lui, et al., "PEGylation Site-Dependent Structura Heterogeneity Study of MonoPEGylated Human Parathyroid hormone Fragment hPTH(1-34)," Langmuir, 30, 11421-11427, (2014).
Mills, et al., "Estimating the power of indirect Comparisons: A Simulation Study," PLoS ONE, vol. 6, Issue 1, e16237, (Jan. 2011).
Mirza, et al., "Secondary Osteoporosis: Pathophysilolgy and Management," Eur J. Endocrinol. 173(3): R131-R151, doi: 10/.1530/EJE-15-0118, (Sep. 2015). Part 1.
Mirza, et al., "Secondary Osteoporosis: Pathophysilolgy and Management," Eur J. Endocrinol. 173(3): R131-R151, doi: 10/.1530/EJE-15-0118, (Sep. 2015). Part 2.
Pan, et al., "Research progress in hormone replacement therapy for hypoparathyroidism after thyroid surgery," Chinese Journal of General Surgery, vol. 24, No. 5, pp. 728-732, (2015).
Smith, et al., "The pH-Rate Profile for the Hydrosysis of a Peptide Bond," J. Am. Chem. Soc., 120, 8910-8913, (1998).
Song, et al., "Validity of indirect comparison for estimating efficancy of competing interventions: empirical evidence from published meta-analyses," BMJ, vol. 326, (Mar. 2003).
U.S. Appl. No. 16/337,955, Final Office Action dated Jul. 14, 2022.
U.S. Appl. No. 16/988,386, Requirement for Restriction/Election dated Jul. 6, 2022.
U.S. Appl. No. 17/055,695, Requirement for Restriction/Election dated Jul. 21, 2022.
U.S. Appl. No. 17/488,137, Final Office Action dated May 13, 2022.
U.S. Appl. No. 16/337,803, Final Office Action dated Sep. 21, 2022.
U.S. Appl. No. 16/337,955, Notice of Allowance dated Sep. 6, 2022.
Cheng, et al., "Teriparatide—Indications beyond osteoporosis," Indian Journal of Endocrinology and Metabolism, vol. 16, Issue 3, pp. 343-348, (May-Jun. 2012).
Shah, et al., "Teriparatide Therapy and Reduced Postoperative Hospitalization for Postsurgical Hypoparathyroidism," JAMA Otoaryngol Head Neck Surg., 141(9):822-827, (2015).
U.S. Appl. No. 16/988,386, Non-Final Office Action dated Oct. 6, 2022.
U.S. Appl. No. 16/988,302, Non-Final Office Action dated Oct. 3, 2022.

* cited by examiner

SEQUENCE LISTING

<160> NUMBER OF SEQ ID NOS: 122

<210> SEQ ID NO 1
<211> LENGTH: 84
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 2
<211> LENGTH: 83
<212> TYPE: PRT
<213> ORGANISM: Artificial Sequence
<220> FEATURE:
<223> OTHER INFORMATION: Human PTH 1-83

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

```
Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
 50                  55                  60

Lys Ser Leu Gly Glu Ala Asp Lys Ala Asp Val Asn Val Leu Thr Lys
 65                  70                  75                  80

Ala Lys Ser

<210> SEQ ID NO 3
<211> LENGTH: 82
<212> TYPE: PRT
<213> ORGANISM: Artificial Sequence
<220> FEATURE:
<223> OTHER INFORMATION: human PTH 1-82

<400> SEQUENCE: 3

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
 50                  55                  60

Lys Ser Leu Gly Glu Ala Asp Lys Ala Asp Val Asn Val Leu Thr Lys
 65                  70                  75                  80

Ala Lys

<210> SEQ ID NO 4
<211> LENGTH: 81
<212> TYPE: PRT
<213> ORGANISM: Artificial Sequence
<220> FEATURE:
<223> OTHER INFORMATION: human PTH 1-81

<400> SEQUENCE: 4

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
 50                  55                  60

Lys Ser Leu Gly Glu Ala Asp Lys Ala Asp Val Asn Val Leu Thr Lys
 65                  70                  75                  80

Ala

<210> SEQ ID NO 5
<211> LENGTH: 80
<212> TYPE: PRT
<213> ORGANISM: Artificial Sequence
<220> FEATURE:
<223> OTHER INFORMATION: human PTH 1-80

<400> SEQUENCE: 5

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
```

```
                20                  25                  30
Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

<210> SEQ ID NO 6
<211> LENGTH: 79
<212> TYPE: PRT
<213> ORGANISM: Artificial Sequence
<220> FEATURE:
<223> OTHER INFORMATION: human PTH 1-79

<400> SEQUENCE: 6

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr
65                  70                  75

<210> SEQ ID NO 7
<211> LENGTH: 78
<212> TYPE: PRT
<213> ORGANISM: Artificial Sequence
<220> FEATURE:
<223> OTHER INFORMATION: human PTH 1-78

<400> SEQUENCE: 7

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu
65                  70                  75

<210> SEQ ID NO 8
<211> LENGTH: 77
<212> TYPE: PRT
<213> ORGANISM: Artificial Sequence
<220> FEATURE:
<223> OTHER INFORMATION: human PTH 1-77

<400> SEQUENCE: 8

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45
```

```
Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val
65                  70                  75

<210> SEQ ID NO 9
<211> LENGTH: 76
<212> TYPE: PRT
<213> ORGANISM: Artificial Sequence
<220> FEATURE:
<223> OTHER INFORMATION: human PTH 1-76

<400> SEQUENCE: 9

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn
65                  70                  75

<210> SEQ ID NO 10
<211> LENGTH: 75
<212> TYPE: PRT
<213> ORGANISM: Artificial Sequence
<220> FEATURE:
<223> OTHER INFORMATION: human PTH 1-75

<400> SEQUENCE: 10

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val
65                  70                  75

<210> SEQ ID NO 11
<211> LENGTH: 74
<212> TYPE: PRT
<213> ORGANISM: Artificial Sequence
<220> FEATURE:
<223> OTHER INFORMATION: human PTH 1-74

<400> SEQUENCE: 11

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
    50                  55                  60
```

```
Lys Ser Leu Gly Glu Ala Asp Lys Ala Asp
65                  70

<210> SEQ ID NO 12
<211> LENGTH: 73
<212> TYPE: PRT
<213> ORGANISM: Artificial Sequence
<220> FEATURE:
<223> OTHER INFORMATION: human PTH 1-73

<400> SEQUENCE: 12

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala
65                  70

<210> SEQ ID NO 13
<211> LENGTH: 72
<212> TYPE: PRT
<213> ORGANISM: Artificial Sequence
<220> FEATURE:
<223> OTHER INFORMATION: human PTH 1-72

<400> SEQUENCE: 13

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys
65                  70

<210> SEQ ID NO 14
<211> LENGTH: 71
<212> TYPE: PRT
<213> ORGANISM: Artificial Sequence
<220> FEATURE:
<223> OTHER INFORMATION: human PTH 1-71

<400> SEQUENCE: 14

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp
65                  70
```

```
<210> SEQ ID NO 15
<211> LENGTH: 70
<212> TYPE: PRT
<213> ORGANISM: Artificial Sequence
<220> FEATURE:
<223> OTHER INFORMATION: human PTH 1-70

<400> SEQUENCE: 15

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala
65                  70

<210> SEQ ID NO 16
<211> LENGTH: 69
<212> TYPE: PRT
<213> ORGANISM: Artificial Sequence
<220> FEATURE:
<223> OTHER INFORMATION: human PTH 1-69

<400> SEQUENCE: 16

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu
65

<210> SEQ ID NO 17
<211> LENGTH: 68
<212> TYPE: PRT
<213> ORGANISM: Artificial Sequence
<220> FEATURE:
<223> OTHER INFORMATION: human PTH 1-68

<400> SEQUENCE: 17

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly
65

<210> SEQ ID NO 18
<211> LENGTH: 67
<212> TYPE: PRT
<213> ORGANISM: Artificial Sequence
```

<220> FEATURE:
<223> OTHER INFORMATION: human PTH 1-67

<400> SEQUENCE: 18

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu
65

<210> SEQ ID NO 19
<211> LENGTH: 66
<212> TYPE: PRT
<213> ORGANISM: Artificial Sequence
<220> FEATURE:
<223> OTHER INFORMATION: human PTH 1-66

<400> SEQUENCE: 19

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser
65

<210> SEQ ID NO 20
<211> LENGTH: 65
<212> TYPE: PRT
<213> ORGANISM: Artificial Sequence
<220> FEATURE:
<223> OTHER INFORMATION: human PTH 1-65

<400> SEQUENCE: 20

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys
65

<210> SEQ ID NO 21
<211> LENGTH: 64
<212> TYPE: PRT
<213> ORGANISM: Artificial Sequence
<220> FEATURE:
<223> OTHER INFORMATION: human PTH 1-64

<400> SEQUENCE: 21

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

<210> SEQ ID NO 22
<211> LENGTH: 63
<212> TYPE: PRT
<213> ORGANISM: Artificial Sequence
<220> FEATURE:
<223> OTHER INFORMATION: human PTH 1-63

<400> SEQUENCE: 22

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His
        50                  55                  60

<210> SEQ ID NO 23
<211> LENGTH: 62
<212> TYPE: PRT
<213> ORGANISM: Artificial Sequence
<220> FEATURE:
<223> OTHER INFORMATION: human PTH 1-62

<400> SEQUENCE: 23

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser
        50                  55                  60

<210> SEQ ID NO 24
<211> LENGTH: 61
<212> TYPE: PRT
<213> ORGANISM: Artificial Sequence
<220> FEATURE:
<223> OTHER INFORMATION: human PTH 1-61

<400> SEQUENCE: 24

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu
        50                  55                  60

```
<210> SEQ ID NO 25
<211> LENGTH: 60
<212> TYPE: PRT
<213> ORGANISM: Artificial Sequence
<220> FEATURE:
<223> OTHER INFORMATION: human PTH 1-60

<400> SEQUENCE: 25

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val
        50                  55                  60

<210> SEQ ID NO 26
<211> LENGTH: 59
<212> TYPE: PRT
<213> ORGANISM: Artificial Sequence
<220> FEATURE:
<223> OTHER INFORMATION: human PTH 1-59

<400> SEQUENCE: 26

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu
        50                  55

<210> SEQ ID NO 27
<211> LENGTH: 58
<212> TYPE: PRT
<213> ORGANISM: Artificial Sequence
<220> FEATURE:
<223> OTHER INFORMATION: human PTH 1-58

<400> SEQUENCE: 27

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val
        50                  55

<210> SEQ ID NO 28
<211> LENGTH: 57
<212> TYPE: PRT
<213> ORGANISM: Artificial Sequence
<220> FEATURE:
<223> OTHER INFORMATION: human PTH 1-57

<400> SEQUENCE: 28

Ser Val Ser Glu Ile Gln Leu Met His Asn Leu Gly Lys His Leu Asn
1               5                   10                  15
```

```
Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn
        50                  55

<210> SEQ ID NO 29
<211> LENGTH: 56
<212> TYPE: PRT
<213> ORGANISM: Artificial Sequence
<220> FEATURE:
<223> OTHER INFORMATION: human PTH 1-56

<400> SEQUENCE: 29

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro Arg Lys Lys Glu Asp
        50                  55

<210> SEQ ID NO 30
<211> LENGTH: 55
<212> TYPE: PRT
<213> ORGANISM: Artificial Sequence
<220> FEATURE:
<223> OTHER INFORMATION: human PTH 1-55

<400> SEQUENCE: 30

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro Arg Lys Lys Glu
        50                  55

<210> SEQ ID NO 31
<211> LENGTH: 54
<212> TYPE: PRT
<213> ORGANISM: Artificial Sequence
<220> FEATURE:
<223> OTHER INFORMATION: human PTH 1-54

<400> SEQUENCE: 31

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro Arg Lys Lys
        50

<210> SEQ ID NO 32
<211> LENGTH: 53
<212> TYPE: PRT
```

```
<213> ORGANISM: Artificial Sequence
<220> FEATURE:
<223> OTHER INFORMATION: human PTH 1-53

<400> SEQUENCE: 32

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys
    50

<210> SEQ ID NO 33
<211> LENGTH: 52
<212> TYPE: PRT
<213> ORGANISM: Artificial Sequence
<220> FEATURE:
<223> OTHER INFORMATION: human PTH 1-52

<400> SEQUENCE: 33

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg
    50

<210> SEQ ID NO 34
<211> LENGTH: 51
<212> TYPE: PRT
<213> ORGANISM: Artificial Sequence
<220> FEATURE:
<223> OTHER INFORMATION: human PTH 1-51

<400> SEQUENCE: 34

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro
    50

<210> SEQ ID NO 35
<211> LENGTH: 50
<212> TYPE: PRT
<213> ORGANISM: Artificial Sequence
<220> FEATURE:
<223> OTHER INFORMATION: human PTH 1-50

<400> SEQUENCE: 35

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
```

```
                35                  40                  45

Gln Arg
    50

<210> SEQ ID NO 36
<211> LENGTH: 49
<212> TYPE: PRT
<213> ORGANISM: Artificial Sequence
<220> FEATURE:
<223> OTHER INFORMATION: human PTH 1-49

<400> SEQUENCE: 36

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln

<210> SEQ ID NO 37
<211> LENGTH: 48
<212> TYPE: PRT
<213> ORGANISM: Artificial Sequence
<220> FEATURE:
<223> OTHER INFORMATION: human PTH 1-48

<400> SEQUENCE: 37

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

<210> SEQ ID NO 38
<211> LENGTH: 47
<212> TYPE: PRT
<213> ORGANISM: Artificial Sequence
<220> FEATURE:
<223> OTHER INFORMATION: human PTH 1-47

<400> SEQUENCE: 38

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly
        35                  40                  45

<210> SEQ ID NO 39
<211> LENGTH: 46
<212> TYPE: PRT
<213> ORGANISM: Artificial Sequence
<220> FEATURE:
<223> OTHER INFORMATION: human PTH 1-46

<400> SEQUENCE: 39

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30
```

Asn Phe Val Ala Leu Gly Ala Pro Leu Ala Pro Arg Asp Ala
        35                  40                  45

<210> SEQ ID NO 40
<211> LENGTH: 45
<212> TYPE: PRT
<213> ORGANISM: Artificial Sequence
<220> FEATURE:
<223> OTHER INFORMATION: human PTH 1-45

<400> SEQUENCE: 40

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp
        35                  40                  45

<210> SEQ ID NO 41
<211> LENGTH: 44
<212> TYPE: PRT
<213> ORGANISM: Artificial Sequence
<220> FEATURE:
<223> OTHER INFORMATION: human PTH 1-44

<400> SEQUENCE: 41

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg
        35                  40

<210> SEQ ID NO 42
<211> LENGTH: 43
<212> TYPE: PRT
<213> ORGANISM: Artificial Sequence
<220> FEATURE:
<223> OTHER INFORMATION: human PTH 1-43

<400> SEQUENCE: 42

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro
        35                  40

<210> SEQ ID NO 43
<211> LENGTH: 42
<212> TYPE: PRT
<213> ORGANISM: Artificial Sequence
<220> FEATURE:
<223> OTHER INFORMATION: human PTH 1-42

<400> SEQUENCE: 43

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala
        35                  40

```
<210> SEQ ID NO 44
<211> LENGTH: 41
<212> TYPE: PRT
<213> ORGANISM: Artificial Sequence
<220> FEATURE:
<223> OTHER INFORMATION: human PTH-41

<400> SEQUENCE: 44

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu
        35                  40

<210> SEQ ID NO 45
<211> LENGTH: 40
<212> TYPE: PRT
<213> ORGANISM: Artificial Sequence
<220> FEATURE:
<223> OTHER INFORMATION: human PTH 1-40

<400> SEQUENCE: 45

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro
        35                  40

<210> SEQ ID NO 46
<211> LENGTH: 39
<212> TYPE: PRT
<213> ORGANISM: Artificial Sequence
<220> FEATURE:
<223> OTHER INFORMATION: human PTH 1-39

<400> SEQUENCE: 46

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala
        35

<210> SEQ ID NO 47
<211> LENGTH: 38
<212> TYPE: PRT
<213> ORGANISM: Artificial Sequence
<220> FEATURE:
<223> OTHER INFORMATION: human PTH 1-38

<400> SEQUENCE: 47

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly
        35

<210> SEQ ID NO 48
```

```
<211> LENGTH: 37
<212> TYPE: PRT
<213> ORGANISM: Artificial Sequence
<220> FEATURE:
<223> OTHER INFORMATION: human PTH 1-37

<400> SEQUENCE: 48

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu
            35

<210> SEQ ID NO 49
<211> LENGTH: 36
<212> TYPE: PRT
<213> ORGANISM: Artificial Sequence
<220> FEATURE:
<223> OTHER INFORMATION: human PTH 1-36

<400> SEQUENCE: 49

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala
            35

<210> SEQ ID NO 50
<211> LENGTH: 35
<212> TYPE: PRT
<213> ORGANISM: Artificial Sequence
<220> FEATURE:
<223> OTHER INFORMATION: human PTH 1-35

<400> SEQUENCE: 50

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val
        35

<210> SEQ ID NO 51
<211> LENGTH: 34
<212> TYPE: PRT
<213> ORGANISM: Artificial Sequence
<220> FEATURE:
<223> OTHER INFORMATION: human PTH 1-34

<400> SEQUENCE: 51

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 52
<211> LENGTH: 33
<212> TYPE: PRT
<213> ORGANISM: Artificial Sequence
<220> FEATURE:
```

<223> OTHER INFORMATION: human PTH 1-33

<400> SEQUENCE: 52

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn

<210> SEQ ID NO 53
<211> LENGTH: 32
<212> TYPE: PRT
<213> ORGANISM: Artificial Sequence
<220> FEATURE:
<223> OTHER INFORMATION: human PTH 1-32

<400> SEQUENCE: 53

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: human PTH 1-31

<400> SEQUENCE: 54

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: human PTH 1-30

<400> SEQUENCE: 55

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp
            20                  25                  30

<210> SEQ ID NO 56
<211> LENGTH: 29
<212> TYPE: PRT
<213> ORGANISM: Artificial Sequence
<220> FEATURE:
<223> OTHER INFORMATION: human PTH 1-29

<400> SEQUENCE: 56

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln
            20                  25

<210> SEQ ID NO 57
<211> LENGTH: 28

```
<212> TYPE: PRT
<213> ORGANISM: Artificial Sequence
<220> FEATURE:
<223> OTHER INFORMATION: human PTH 1-28

<400> SEQUENCE: 57

Ser Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 58
<211> LENGTH: 27
<212> TYPE: PRT
<213> ORGANISM: Artificial Sequence
<220> FEATURE:
<223> OTHER INFORMATION: human PTH 1-27

<400> SEQUENCE: 58

Ser Val Ser Glu Ile Gln Leu Met His Asn Leu Gly Lys His Leu Asn
1               5                   10                  15

Ser Met Glu Arg Val Glu Trp Leu Arg Lys Lys
            20                  25

<210> SEQ ID NO 59
<211> LENGTH: 26
<212> TYPE: PRT
<213> ORGANISM: Artificial Sequence
<220> FEATURE:
<223> OTHER INFORMATION: human PTH 1-26

<400> SEQUENCE: 59

Ser Val Ser Glu Ile Gln Leu Met His Asn Leu Gly Lys His Leu Asn
1               5                   10                  15

Ser Met Glu Arg Val Glu Trp Leu Arg Lys
            20                  25

<210> SEQ ID NO 60
<211> LENGTH: 25
<212> TYPE: PRT
<213> ORGANISM: Artificial Sequence
<220> FEATURE:
<223> OTHER INFORMATION: human PTH 1-25

<400> SEQUENCE: 60

Ser Val Ser Glu Ile Gln Leu Met His Asn Leu Gly Lys His Leu Asn
1               5                   10                  15

Ser Met Glu Arg Val Glu Trp Leu Arg
            20                  25

<210> SEQ ID NO 61
<211> LENGTH: 84
<212> TYPE: PRT
<213> ORGANISM: Artificial Sequence
<220> FEATURE:
<223> OTHER INFORMATION: amidated human PTH 1-84
<220> FEATURE:
<221> NAME/KEY: MOD_RES
<222> LOCATION: (84)..(84)
<223> OTHER INFORMATION: AMIDATION

<400> SEQUENCE: 61

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
```

```
                    20                  25                  30

Asn Phe Val Ala Leu Gly Ala Pro Leu Ala Pro Arg Asp Ala Gly Ser
                35                  40                  45

Gln Arg Pro Arg Lys Lys Glu Asp Asn Val Leu Val Glu Ser His Glu
            50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 62
<211> LENGTH: 83
<212> TYPE: PRT
<213> ORGANISM: Artificial Sequence
<220> FEATURE:
<223> OTHER INFORMATION: amidated human PTH 1-83
<220> FEATURE:
<221> NAME/KEY: MOD_RES
<222> LOCATION: (83)..(83)
<223> OTHER INFORMATION: AMIDATION

<400> SEQUENCE: 62

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
                35                  40                  45

Gln Arg Pro Arg Lys Lys Glu Asp Asn Val Leu Val Glu Ser His Glu
            50                  55                  60

Lys Ser Leu Gly Glu Ala Asp Lys Ala Asp Val Asn Val Leu Thr Lys
65                  70                  75                  80

Ala Lys Ser

<210> SEQ ID NO 63
<211> LENGTH: 82
<212> TYPE: PRT
<213> ORGANISM: Artificial Sequence
<220> FEATURE:
<223> OTHER INFORMATION: amidated human PTH 1-82
<220> FEATURE:
<221> NAME/KEY: MOD_RES
<222> LOCATION: (82)..(82)
<223> OTHER INFORMATION: AMIDATION

<400> SEQUENCE: 63

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
                35                  40                  45

Gln Arg Pro Arg Lys Lys Glu Asp Asn Val Leu Val Glu Ser His Glu
            50                  55                  60

Lys Ser Leu Gly Glu Ala Asp Lys Ala Asp Val Asn Val Leu Thr Lys
65                  70                  75                  80

Ala Lys

<210> SEQ ID NO 64
<211> LENGTH: 81
<212> TYPE: PRT
```

<213> ORGANISM: Artificial Sequence
<220> FEATURE:
<223> OTHER INFORMATION: amidated human PTH 1-81
<220> FEATURE:
<221> NAME/KEY: MOD_RES
<222> LOCATION: (81)..(81)
<223> OTHER INFORMATION: AMIDATION

<400> SEQUENCE: 64

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala

<210> SEQ ID NO 65
<211> LENGTH: 80
<212> TYPE: PRT
<213> ORGANISM: Artificial Sequence
<220> FEATURE:
<223> OTHER INFORMATION: amidated human PTH 1-80
<220> FEATURE:
<221> NAME/KEY: MOD_RES
<222> LOCATION: (80)..(80)
<223> OTHER INFORMATION: AMIDATION

<400> SEQUENCE: 65

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

<210> SEQ ID NO 66
<211> LENGTH: 79
<212> TYPE: PRT
<213> ORGANISM: Artificial Sequence
<220> FEATURE:
<223> OTHER INFORMATION: amidated human PTH 1-79
<220> FEATURE:
<221> NAME/KEY: MOD_RES
<222> LOCATION: (79)..(79)
<223> OTHER INFORMATION: AMIDATION

<400> SEQUENCE: 66

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

```
Gln Arg Pro Arg Lys Lys Glu Asp Asn Val Leu Val Glu Ser His Glu
     50                  55                  60

Lys Ser Leu Gly Glu Ala Asp Lys Ala Asp Val Asn Val Leu Thr
 65                  70                  75
```

<210> SEQ ID NO 67
<211> LENGTH: 78
<212> TYPE: PRT
<213> ORGANISM: Artificial Sequence
<220> FEATURE:
<223> OTHER INFORMATION: amidated human PTH 1-78
<220> FEATURE:
<221> NAME/KEY: MOD_RES
<222> LOCATION: (78)..(78)
<223> OTHER INFORMATION: AMIDATION

<400> SEQUENCE: 67

```
Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                 20                  25                  30

Asn Phe Val Ala Leu Gly Ala Pro Leu Ala Pro Arg Asp Ala Gly Ser
             35                  40                  45

Gln Arg Pro Arg Lys Lys Glu Asp Asn Val Leu Val Glu Ser His Glu
     50                  55                  60

Lys Ser Leu Gly Glu Ala Asp Lys Ala Asp Val Asn Val Leu
 65                  70                  75
```

<210> SEQ ID NO 68
<211> LENGTH: 77
<212> TYPE: PRT
<213> ORGANISM: Artificial Sequence
<220> FEATURE:
<223> OTHER INFORMATION: amidated human PTH 1-77
<220> FEATURE:
<221> NAME/KEY: MOD_RES
<222> LOCATION: (77)..(77)
<223> OTHER INFORMATION: AMIDATION

<400> SEQUENCE: 68

```
Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
                 20                  25                  30

Asn Phe Val Ala Leu Gly Ala Pro Leu Ala Pro Arg Asp Ala Gly Ser
             35                  40                  45

Gln Arg Pro Arg Lys Lys Glu Asp Asn Val Leu Val Glu Ser His Glu
     50                  55                  60

Lys Ser Leu Gly Glu Ala Asp Lys Ala Asp Val Asn Val
 65                  70                  75
```

<210> SEQ ID NO 69
<211> LENGTH: 76
<212> TYPE: PRT
<213> ORGANISM: Artificial Sequence
<220> FEATURE:
<223> OTHER INFORMATION: amidated human PTH 1-76
<220> FEATURE:
<221> NAME/KEY: MOD_RES
<222> LOCATION: (76)..(76)
<223> OTHER INFORMATION: AMIDATION

<400> SEQUENCE: 69

```
Ser Val Ser Glu Ile Gln Leu Met His Asn Leu Gly Lys His Leu Asn
```

```
                1               5                   10                  15
Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn
65                  70                  75

<210> SEQ ID NO 70
<211> LENGTH: 75
<212> TYPE: PRT
<213> ORGANISM: Artificial Sequence
<220> FEATURE:
<223> OTHER INFORMATION: amidated human PTH 1-75
<220> FEATURE:
<221> NAME/KEY: MOD_RES
<222> LOCATION: (75)..(75)
<223> OTHER INFORMATION: AMIDATION

<400> SEQUENCE: 70

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val
65                  70                  75

<210> SEQ ID NO 71
<211> LENGTH: 74
<212> TYPE: PRT
<213> ORGANISM: Artificial Sequence
<220> FEATURE:
<223> OTHER INFORMATION: amidated human PTH 1-74
<220> FEATURE:
<221> NAME/KEY: MOD_RES
<222> LOCATION: (74)..(74)
<223> OTHER INFORMATION: AMIDATION

<400> SEQUENCE: 71

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp
65                  70

<210> SEQ ID NO 72
<211> LENGTH: 73
<212> TYPE: PRT
<213> ORGANISM: Artificial Sequence
<220> FEATURE:
<223> OTHER INFORMATION: amidated human PTH 1-73
```

```
<220> FEATURE:
<221> NAME/KEY: MOD_RES
<222> LOCATION: (73)..(73)
<223> OTHER INFORMATION: AMIDATION

<400> SEQUENCE: 72

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala
65                  70

<210> SEQ ID NO 73
<211> LENGTH: 72
<212> TYPE: PRT
<213> ORGANISM: Artificial Sequence
<220> FEATURE:
<223> OTHER INFORMATION: amidated human PTH 1-72
<220> FEATURE:
<221> NAME/KEY: MOD_RES
<222> LOCATION: (72)..(72)
<223> OTHER INFORMATION: AMIDATION

<400> SEQUENCE: 73

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys
65                  70

<210> SEQ ID NO 74
<211> LENGTH: 71
<212> TYPE: PRT
<213> ORGANISM: Artificial Sequence
<220> FEATURE:
<223> OTHER INFORMATION: amidated human PTH 1-71
<220> FEATURE:
<221> NAME/KEY: MOD_RES
<222> LOCATION: (71)..(71)
<223> OTHER INFORMATION: AMIDATION

<400> SEQUENCE: 74

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp
65                  70
```

<210> SEQ ID NO 75
<211> LENGTH: 70
<212> TYPE: PRT
<213> ORGANISM: Artificial Sequence
<220> FEATURE:
<223> OTHER INFORMATION: amidated human PTH 1-70
<220> FEATURE:
<221> NAME/KEY: MOD_RES
<222> LOCATION: (70)..(70)
<223> OTHER INFORMATION: AMIDATION

<400> SEQUENCE: 75

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala
65                  70

<210> SEQ ID NO 76
<211> LENGTH: 69
<212> TYPE: PRT
<213> ORGANISM: Artificial Sequence
<220> FEATURE:
<223> OTHER INFORMATION: amidated human PTH 1-69
<220> FEATURE:
<221> NAME/KEY: MOD_RES
<222> LOCATION: (69)..(69)
<223> OTHER INFORMATION: AMIDATION

<400> SEQUENCE: 76

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu
65

<210> SEQ ID NO 77
<211> LENGTH: 68
<212> TYPE: PRT
<213> ORGANISM: Artificial Sequence
<220> FEATURE:
<223> OTHER INFORMATION: amidated human PTH 1-68
<220> FEATURE:
<221> NAME/KEY: MOD_RES
<222> LOCATION: (68)..(68)
<223> OTHER INFORMATION: AMIDATION

<400> SEQUENCE: 77

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
 50                  55                  60

Lys Ser Leu Gly
 65

<210> SEQ ID NO 78
<211> LENGTH: 67
<212> TYPE: PRT
<213> ORGANISM: Artificial Sequence
<220> FEATURE:
<223> OTHER INFORMATION: amidated human PTH 1-67
<220> FEATURE:
<221> NAME/KEY: MOD_RES
<222> LOCATION: (67)..(67)
<223> OTHER INFORMATION: AMIDATION

<400> SEQUENCE: 78

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
 50                  55                  60

Lys Ser Leu
 65

<210> SEQ ID NO 79
<211> LENGTH: 66
<212> TYPE: PRT
<213> ORGANISM: Artificial Sequence
<220> FEATURE:
<223> OTHER INFORMATION: amidated human PTH 1-66
<220> FEATURE:
<221> NAME/KEY: MOD_RES
<222> LOCATION: (66)..(66)
<223> OTHER INFORMATION: AMIDATION

<400> SEQUENCE: 79

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
 50                  55                  60

Lys Ser
 65

<210> SEQ ID NO 80
<211> LENGTH: 65
<212> TYPE: PRT
<213> ORGANISM: Artificial Sequence
<220> FEATURE:
<223> OTHER INFORMATION: amidated human PTH 1-65
<220> FEATURE:
<221> NAME/KEY: MOD_RES
<222> LOCATION: (65)..(65)
<223> OTHER INFORMATION: AMIDATION

```
<400> SEQUENCE: 80

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys
65

<210> SEQ ID NO 81
<211> LENGTH: 64
<212> TYPE: PRT
<213> ORGANISM: Artificial Sequence
<220> FEATURE:
<223> OTHER INFORMATION: amidated human PTH 1-64
<220> FEATURE:
<221> NAME/KEY: MOD_RES
<222> LOCATION: (64)..(64)
<223> OTHER INFORMATION: AMIDATION

<400> SEQUENCE: 81

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

<210> SEQ ID NO 82
<211> LENGTH: 63
<212> TYPE: PRT
<213> ORGANISM: Artificial Sequence
<220> FEATURE:
<223> OTHER INFORMATION: amidated human PTH 1-63
<220> FEATURE:
<221> NAME/KEY: MOD_RES
<222> LOCATION: (63)..(63)
<223> OTHER INFORMATION: AMIDATION

<400> SEQUENCE: 82

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His
    50                  55                  60

<210> SEQ ID NO 83
<211> LENGTH: 62
<212> TYPE: PRT
<213> ORGANISM: Artificial Sequence
<220> FEATURE:
<223> OTHER INFORMATION: amidated human PTH 1-62
<220> FEATURE:
<221> NAME/KEY: MOD_RES
<222> LOCATION: (62)..(62)
```

<223> OTHER INFORMATION: AMIDATION

<400> SEQUENCE: 83

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser
    50                  55                  60

<210> SEQ ID NO 84
<211> LENGTH: 61
<212> TYPE: PRT
<213> ORGANISM: Artificial Sequence
<220> FEATURE:
<223> OTHER INFORMATION: amidated human PTH 1-61
<220> FEATURE:
<221> NAME/KEY: MOD_RES
<222> LOCATION: (61)..(61)
<223> OTHER INFORMATION: AMIDATION

<400> SEQUENCE: 84

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu
    50                  55                  60

<210> SEQ ID NO 85
<211> LENGTH: 60
<212> TYPE: PRT
<213> ORGANISM: Artificial Sequence
<220> FEATURE:
<223> OTHER INFORMATION: amidated human PTH 1-60
<220> FEATURE:
<221> NAME/KEY: MOD_RES
<222> LOCATION: (60)..(60)
<223> OTHER INFORMATION: ACETYLATION

<400> SEQUENCE: 85

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val
    50                  55                  60

<210> SEQ ID NO 86
<211> LENGTH: 59
<212> TYPE: PRT
<213> ORGANISM: Artificial Sequence
<220> FEATURE:
<223> OTHER INFORMATION: amidated human PTH 1-59
<220> FEATURE:
<221> NAME/KEY: MOD_RES
<222> LOCATION: (59)..(59)
<223> OTHER INFORMATION: AMIDATION -continued

<400> SEQUENCE: 86

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu
    50                  55

<210> SEQ ID NO 87
<211> LENGTH: 58
<212> TYPE: PRT
<213> ORGANISM: Artificial Sequence
<220> FEATURE:
<223> OTHER INFORMATION: amidated human PTH 1-58
<220> FEATURE:
<221> NAME/KEY: MOD_RES
<222> LOCATION: (58)..(58)
<223> OTHER INFORMATION: AMIDATION

<400> SEQUENCE: 87

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val
    50                  55

<210> SEQ ID NO 88
<211> LENGTH: 57
<212> TYPE: PRT
<213> ORGANISM: Artificial Sequence
<220> FEATURE:
<223> OTHER INFORMATION: amidated human PTH 1-57
<220> FEATURE:
<221> NAME/KEY: MOD_RES
<222> LOCATION: (57)..(57)
<223> OTHER INFORMATION: AMIDATION

<400> SEQUENCE: 88

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn
    50                  55

<210> SEQ ID NO 89
<211> LENGTH: 56
<212> TYPE: PRT
<213> ORGANISM: Artificial Sequence
<220> FEATURE:
<223> OTHER INFORMATION: amidated human PTH 1-56
<220> FEATURE:
<221> NAME/KEY: MOD_RES
<222> LOCATION: (56)..(56)
<223> OTHER INFORMATION: AMIDATION

```
<400> SEQUENCE: 89

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp
    50                  55

<210> SEQ ID NO 90
<211> LENGTH: 55
<212> TYPE: PRT
<213> ORGANISM: Artificial Sequence
<220> FEATURE:
<223> OTHER INFORMATION: amidated human PTH 1-55
<220> FEATURE:
<221> NAME/KEY: MOD_RES
<222> LOCATION: (55)..(55)
<223> OTHER INFORMATION: AMIDATION

<400> SEQUENCE: 90

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu
    50                  55

<210> SEQ ID NO 91
<211> LENGTH: 54
<212> TYPE: PRT
<213> ORGANISM: Artificial Sequence
<220> FEATURE:
<223> OTHER INFORMATION: amidated human PTH 1-54
<220> FEATURE:
<221> NAME/KEY: MOD_RES
<222> LOCATION: (54)..(54)
<223> OTHER INFORMATION: AMIDATION

<400> SEQUENCE: 91

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys
    50

<210> SEQ ID NO 92
<211> LENGTH: 53
<212> TYPE: PRT
<213> ORGANISM: Artificial Sequence
<220> FEATURE:
<223> OTHER INFORMATION: amidated human PTH 1-53
<220> FEATURE:
<221> NAME/KEY: MOD_RES
<222> LOCATION: (53)..(53)
<223> OTHER INFORMATION: AMIDATION

<400> SEQUENCE: 92
```

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
                35                  40                  45

Gln Arg Pro Arg Lys
        50
```

<210> SEQ ID NO 93
<211> LENGTH: 52
<212> TYPE: PRT
<213> ORGANISM: Artificial Sequence
<220> FEATURE:
<223> OTHER INFORMATION: amidated human PTH 1-52
<220> FEATURE:
<221> NAME/KEY: MOD_RES
<222> LOCATION: (52)..(52)
<223> OTHER INFORMATION: AMIDATION

<400> SEQUENCE: 93

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
                35                  40                  45

Gln Arg Pro Arg
        50
```

<210> SEQ ID NO 94
<211> LENGTH: 51
<212> TYPE: PRT
<213> ORGANISM: Artificial Sequence
<220> FEATURE:
<223> OTHER INFORMATION: amidated human PTH 1-51
<220> FEATURE:
<221> NAME/KEY: MOD_RES
<222> LOCATION: (51)..(51)
<223> OTHER INFORMATION: AMIDATION

<400> SEQUENCE: 94

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
                35                  40                  45

Gln Arg Pro
        50
```

<210> SEQ ID NO 95
<211> LENGTH: 50
<212> TYPE: PRT
<213> ORGANISM: Artificial Sequence
<220> FEATURE:
<223> OTHER INFORMATION: amidated human PTH 1-50
<220> FEATURE:
<221> NAME/KEY: MOD_RES
<222> LOCATION: (50)..(50)
<223> OTHER INFORMATION: AMIDATION

<400> SEQUENCE: 95

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg
    50

<210> SEQ ID NO 96
<211> LENGTH: 49
<212> TYPE: PRT
<213> ORGANISM: Artificial Sequence
<220> FEATURE:
<223> OTHER INFORMATION: amidated human PTH 1-49
<220> FEATURE:
<221> NAME/KEY: MOD_RES
<222> LOCATION: (49)..(49)
<223> OTHER INFORMATION: AMIDATION

<400> SEQUENCE: 96

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln

<210> SEQ ID NO 97
<211> LENGTH: 48
<212> TYPE: PRT
<213> ORGANISM: Artificial Sequence
<220> FEATURE:
<223> OTHER INFORMATION: amidated human PTH 1-48
<220> FEATURE:
<221> NAME/KEY: MOD_RES
<222> LOCATION: (48)..(48)
<223> OTHER INFORMATION: AMIDATION

<400> SEQUENCE: 97

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

<210> SEQ ID NO 98
<211> LENGTH: 47
<212> TYPE: PRT
<213> ORGANISM: Artificial Sequence
<220> FEATURE:
<223> OTHER INFORMATION: amidated human PTH 1-47
<220> FEATURE:
<221> NAME/KEY: MOD_RES
<222> LOCATION: (47)..(47)
<223> OTHER INFORMATION: AMIDATION

<400> SEQUENCE: 98

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30
```

Asn Phe Val Ala Leu Gly Ala Pro Leu Ala Pro Arg Asp Ala Gly
            35                  40                  45

<210> SEQ ID NO 99
<211> LENGTH: 46
<212> TYPE: PRT
<213> ORGANISM: Artificial Sequence
<220> FEATURE:
<223> OTHER INFORMATION: amidated human PTH 1-46
<220> FEATURE:
<221> NAME/KEY: MOD_RES
<222> LOCATION: (46)..(46)
<223> OTHER INFORMATION: AMIDATION

<400> SEQUENCE: 99

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala
            35                  40                  45

<210> SEQ ID NO 100
<211> LENGTH: 45
<212> TYPE: PRT
<213> ORGANISM: Artificial Sequence
<220> FEATURE:
<223> OTHER INFORMATION: amidated human PTH 1-45
<220> FEATURE:
<221> NAME/KEY: MOD_RES
<222> LOCATION: (45)..(45)
<223> OTHER INFORMATION: AMIDATION

<400> SEQUENCE: 100

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp
            35                  40                  45

<210> SEQ ID NO 101
<211> LENGTH: 44
<212> TYPE: PRT
<213> ORGANISM: Artificial Sequence
<220> FEATURE:
<223> OTHER INFORMATION: amidated human PTH 1-44
<220> FEATURE:
<221> NAME/KEY: MOD_RES
<222> LOCATION: (44)..(44)
<223> OTHER INFORMATION: AMIDATION

<400> SEQUENCE: 101

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg
            35                  40

<210> SEQ ID NO 102
<211> LENGTH: 43
<212> TYPE: PRT
<213> ORGANISM: Artificial Sequence
<220> FEATURE:

<223> OTHER INFORMATION: amidated human PTH 1-43
<220> FEATURE:
<221> NAME/KEY: MOD_RES
<222> LOCATION: (43)..(43)
<223> OTHER INFORMATION: AMIDATION

<400> SEQUENCE: 102

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro
        35                  40

<210> SEQ ID NO 103
<211> LENGTH: 42
<212> TYPE: PRT
<213> ORGANISM: Artificial Sequence
<220> FEATURE:
<223> OTHER INFORMATION: amidated human PTH 1-42
<220> FEATURE:
<221> NAME/KEY: MOD_RES
<222> LOCATION: (42)..(42)
<223> OTHER INFORMATION: AMIDATION

<400> SEQUENCE: 103

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala
        35                  40

<210> SEQ ID NO 104
<211> LENGTH: 41
<212> TYPE: PRT
<213> ORGANISM: Artificial Sequence
<220> FEATURE:
<223> OTHER INFORMATION: amidated human PTH 1-41
<220> FEATURE:
<221> NAME/KEY: MOD_RES
<222> LOCATION: (41)..(41)
<223> OTHER INFORMATION: AMIDATION

<400> SEQUENCE: 104

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu
        35                  40

<210> SEQ ID NO 105
<211> LENGTH: 40
<212> TYPE: PRT
<213> ORGANISM: Artificial Sequence
<220> FEATURE:
<223> OTHER INFORMATION: amidated human PTH 1-40
<220> FEATURE:
<221> NAME/KEY: MOD_RES
<222> LOCATION: (40)..(40)
<223> OTHER INFORMATION: AMIDATION

<400> SEQUENCE: 105

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro
        35                  40

<210> SEQ ID NO 106
<211> LENGTH: 39
<212> TYPE: PRT
<213> ORGANISM: Artificial Sequence
<220> FEATURE:
<223> OTHER INFORMATION: amidated human PTH 1-39
<220> FEATURE:
<221> NAME/KEY: MOD_RES
<222> LOCATION: (39)..(39)
<223> OTHER INFORMATION: AMIDATION

<400> SEQUENCE: 106

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala
        35

<210> SEQ ID NO 107
<211> LENGTH: 38
<212> TYPE: PRT
<213> ORGANISM: Artificial Sequence
<220> FEATURE:
<223> OTHER INFORMATION: amidated human PTH 1-38
<220> FEATURE:
<221> NAME/KEY: MOD_RES
<222> LOCATION: (38)..(38)
<223> OTHER INFORMATION: AMIDATION

<400> SEQUENCE: 107

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly
        35

<210> SEQ ID NO 108
<211> LENGTH: 37
<212> TYPE: PRT
<213> ORGANISM: Artificial Sequence
<220> FEATURE:
<223> OTHER INFORMATION: amidated human PTH 1-37
<220> FEATURE:
<221> NAME/KEY: MOD_RES
<222> LOCATION: (37)..(37)
<223> OTHER INFORMATION: AMIDATION

<400> SEQUENCE: 108

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu
        35

<210> SEQ ID NO 109
<211> LENGTH: 36

```
<212> TYPE: PRT
<213> ORGANISM: Artificial Sequence
<220> FEATURE:
<223> OTHER INFORMATION: amidated human PTH 1-36
<220> FEATURE:
<221> NAME/KEY: MOD_RES
<222> LOCATION: (36)..(36)
<223> OTHER INFORMATION: AMIDATION

<400> SEQUENCE: 109

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala
        35

<210> SEQ ID NO 110
<211> LENGTH: 35
<212> TYPE: PRT
<213> ORGANISM: Artificial Sequence
<220> FEATURE:
<223> OTHER INFORMATION: amidated human PTH 1-35
<220> FEATURE:
<221> NAME/KEY: MOD_RES
<222> LOCATION: (35)..(35)
<223> OTHER INFORMATION: AMIDATION

<400> SEQUENCE: 110

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val
        35

<210> SEQ ID NO 111
<211> LENGTH: 34
<212> TYPE: PRT
<213> ORGANISM: Artificial Sequence
<220> FEATURE:
<223> OTHER INFORMATION: amidated human PTH 1-34
<220> FEATURE:
<221> NAME/KEY: MOD_RES
<222> LOCATION: (34)..(34)
<223> OTHER INFORMATION: AMIDATION

<400> SEQUENCE: 111

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 112
<211> LENGTH: 33
<212> TYPE: PRT
<213> ORGANISM: Artificial Sequence
<220> FEATURE:
<223> OTHER INFORMATION: amidated human PTH 1-33
<220> FEATURE:
<221> NAME/KEY: MOD_RES
<222> LOCATION: (33)..(33)
<223> OTHER INFORMATION: AMIDATION

<400> SEQUENCE: 112
```

-continued

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn

<210> SEQ ID NO 113
<211> LENGTH: 32
<212> TYPE: PRT
<213> ORGANISM: Artificial Sequence
<220> FEATURE:
<223> OTHER INFORMATION: amidated human PTH 1-32
<220> FEATURE:
<221> NAME/KEY: MOD_RES
<222> LOCATION: (32)..(32)
<223> OTHER INFORMATION: AMIDATION

<400> SEQUENCE: 113

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

<210> SEQ ID NO 114
<211> LENGTH: 31
<212> TYPE: PRT
<213> ORGANISM: Artificial Sequence
<220> FEATURE:
<223> OTHER INFORMATION: amidated human PTH 1-31
<220> FEATURE:
<221> NAME/KEY: MOD_RES
<222> LOCATION: (31)..(31)
<223> OTHER INFORMATION: AMIDATION

<400> SEQUENCE: 114

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30

<210> SEQ ID NO 115
<211> LENGTH: 30
<212> TYPE: PRT
<213> ORGANISM: Artificial Sequence
<220> FEATURE:
<223> OTHER INFORMATION: amidated human PTH 1-30
<220> FEATURE:
<221> NAME/KEY: MOD_RES
<222> LOCATION: (30)..(30)
<223> OTHER INFORMATION: AMIDATION

<400> SEQUENCE: 115

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp
            20                  25                  30

<210> SEQ ID NO 116
<211> LENGTH: 29
<212> TYPE: PRT
<213> ORGANISM: Artificial Sequence
<220> FEATURE:
<223> OTHER INFORMATION: amidated human PTH 1-29
<220> FEATURE:
<221> NAME/KEY: MOD_RES
<222> LOCATION: (29)..(29)
<223> OTHER INFORMATION: AMIDATION
```

<400> SEQUENCE: 116

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln
            20                  25

<210> SEQ ID NO 117
<211> LENGTH: 28
<212> TYPE: PRT
<213> ORGANISM: Artificial Sequence
<220> FEATURE:
<223> OTHER INFORMATION: amidated human PTH 1-28
<220> FEATURE:
<221> NAME/KEY: MOD_RES
<222> LOCATION: (28)..(28)
<223> OTHER INFORMATION: AMIDATION

<400> SEQUENCE: 117

Ser Val Ser Glu Ile Gln Leu Met His Asn Leu Gly Lys His Leu Asn
1               5                   10                  15

Ser Met Glu Arg Val Glu Trp Leu Arg Lys Lys Leu
            20                  25

<210> SEQ ID NO 118
<211> LENGTH: 27
<212> TYPE: PRT
<213> ORGANISM: Artificial Sequence
<220> FEATURE:
<223> OTHER INFORMATION: amidated human PTH 1-27
<220> FEATURE:
<221> NAME/KEY: MOD_RES
<222> LOCATION: (27)..(27)
<223> OTHER INFORMATION: AMIDATION

<400> SEQUENCE: 118

Ser Val Ser Glu Ile Gln Leu Met His Asn Leu Gly Lys His Leu Asn
1               5                   10                  15

Ser Met Glu Arg Val Glu Trp Leu Arg Lys Lys
            20                  25

<210> SEQ ID NO 119
<211> LENGTH: 26
<212> TYPE: PRT
<213> ORGANISM: Artificial Sequence
<220> FEATURE:
<223> OTHER INFORMATION: amidated human PTH 1-26
<220> FEATURE:
<221> NAME/KEY: MOD_RES
<222> LOCATION: (26)..(26)
<223> OTHER INFORMATION: AMIDATION

<400> SEQUENCE: 119

Ser Val Ser Glu Ile Gln Leu Met His Asn Leu Gly Lys His Leu Asn
1               5                   10                  15

Ser Met Glu Arg Val Glu Trp Leu Arg Lys
            20                  25

<210> SEQ ID NO 120
<211> LENGTH: 25
<212> TYPE: PRT
<213> ORGANISM: Artificial Sequence
<220> FEATURE:
<223> OTHER INFORMATION: amidated human PTH 1-25
<220> FEATURE:
<221> NAME/KEY: MOD_RES
<222> LOCATION: (25)..(25)

```
<223> OTHER INFORMATION: AMIDATION

<400> SEQUENCE: 120

Ser Val Ser Glu Ile Gln Leu Met His Asn Leu Gly Lys His Leu Asn
1               5                   10                  15

Ser Met Glu Arg Val Glu Trp Leu Arg
            20                  25

<210> SEQ ID NO 121
<211> LENGTH: 141
<212> TYPE: PRT
<213> ORGANISM: Homo sapiens

<400> SEQUENCE: 121

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile Arg Ala Thr Ser Glu Val Ser Pro Asn Ser Lys Pro
        35                  40                  45

Ser Pro Asn Thr Lys Asn His Pro Val Arg Phe Gly Ser Asp Asp Glu
    50                  55                  60

Gly Arg Tyr Leu Thr Gln Glu Thr Asn Lys Val Glu Thr Tyr Lys Glu
65                  70                  75                  80

Gln Pro Leu Lys Thr Pro Gly Lys Lys Lys Lys Gly Lys Pro Gly Lys
                85                  90                  95

Arg Lys Glu Gln Glu Lys Lys Lys Arg Arg Thr Arg Ser Ala Trp Leu
            100                 105                 110

Asp Ser Gly Val Thr Gly Ser Gly Leu Glu Gly Asp His Leu Ser Asp
        115                 120                 125

Thr Ser Thr Thr Ser Leu Glu Leu Asp Ser Arg Arg His
    130                 135                 140

<210> SEQ ID NO 122
<211> LENGTH: 20
<212> TYPE: PRT
<213> ORGANISM: Artificial Sequence
<220> FEATURE:
<223> OTHER INFORMATION: Artificial random coil

<400> SEQUENCE: 122

Gly Gly Pro Gly Gly Pro Gly Pro Gly Pro Gly Gly Pro Gly Gly Pro
1               5                   10                  15

Gly Gly Pro Gly
            20
```

DOSAGE REGIMEN FOR A CONTROLLED-RELEASE PTH COMPOUND

The present invention relates to a pharmaceutical composition comprising at least one controlled-release PTH compound or a pharmaceutically acceptable salt, hydrate or solvate thereof, for use in the treatment, control, delay or prevention of a condition that can be treated, controlled, delayed or prevented with PTH, wherein said pharmaceutical composition is administered no more frequent than once every 24 hours with a dosage of the controlled-release PTH compound that corresponds to no more than 70% of the molar equivalent dose of PTH 1-84 administered every 24 hours required to maintain serum calcium within normal levels over said 24 hour period in humans and to methods of treating, controlling, delaying or preventing said conditions.

Hypoparathyroidism is a rare endocrine disorder of calcium and phosphate metabolism that most often arises as a result of parathyroid gland damage or removal during surgery of the thyroid gland. Hypoparathyroidism is unusual among endocrine disorders in that it has not been treated, until recently, by replacement with the missing hormone, parathyroid hormone, or PTH. Conventional therapy for hypoparathyroidism involves large doses of vitamin D and oral calcium supplementation, which, although often effective, is associated with marked swings in blood $Ca^{2+}$ resulting in hypercalcemia and hypocalcemia, excess urinary calcium excretion, nephrocalcinosis and ectopic calcifications, including vascular, basal ganglia, and lens of eye.

Calcium is the most abundant mineral in the human body, and its tight regulation is required for many critical biological functions, such as bone mineralization, muscle contraction, nerve conduction, hormone release, and blood coagulation. It is particularly important to maintain calcium concentration as stable as possible, because of the high sensitivity of a variety of cell systems or organs, including the central nervous system, muscle, and exo/endocrine glands, to small variations in $Ca^{2+}$. PTH is a major regulator of calcium homeostasis.

The inappropriately low PTH level in relation to serum $Ca^{2+}$ concentration, characteristic of hypoparathyroidism, leads to decreased renal tubular reabsorption of $Ca^{2+}$ and simultaneously, to increased renal tubular reabsorption of phosphate. Thus, the main biochemical abnormalities of hypoparathyroidism are hypocalcemia and hyperphosphatemia. Clinical features of the disease include symptoms of hypocalcemia, such as perioral numbness, paresthesias, and carpal/pedal muscle spasms. Laryngeal spasm, tetany, and seizures are serious and potentially life-threatening complications. Hyperphosphatemia and an elevated calcium x phosphate product contributes to ectopic deposition of insoluble calcium phosphate complexes in soft tissues, including vasculature, brain, kidneys, and other organs.

Standard therapy of hypoparathyroidism is oral calcium and vitamin D supplementation. The goals of therapy are to a) ameliorate symptoms of hypocalcemia; b) maintain fasting serum calcium within or slightly below to the low-normal range; c) maintain fasting serum phosphorus within the high normal range or only slightly elevated; d) avoid or minimize hypercalciuria; e) maintain a calcium-phosphate product at levels well below the upper limit of normal and f) avoid ectopic calcification of the kidney (stones and nephrocalcinosis) and other soft tissues.

Several concerns arise with prolonged use of calcium and active vitamin D in large doses, particularly with regard to hypercalciuria, kidney stones, nephrocalcinosis and ectopic soft tissue calcification. In addition, conventional therapy with calcium and active vitamin D does not alleviate quality of life complaints nor does it reverse abnormalities in bone remodeling characteristic of the disease. In short, there is a high need for improved therapies for hypoparathyroidism.

In 2015, Natpara, PTH(1-84), was approved for once-daily subcutaneous injection as an adjunct to vitamin D and calcium in patients with hypoparathyroidism. Natpara, PTH (1-84), was approved to control hypocalcemia based on a pivotal trial demonstrating that 42 percent of PTH(1-84) treated participants achieved normal blood calcium levels on reduced doses of calcium supplements and active forms of vitamin D, compared to 3 percent of placebo-treated participants. Following a time course in which serum calcium was monitored after injection, 71 percent of patients treated with PTH(1-84) developed hypercalcemia at one or more measurements during a 24-hour period. PTH(1-84) reduced urinary calcium excretion 2-8 hours after injection but over the 24-hour period, urinary calcium excretion did not change. Similarly, urinary phosphate excretion increased only during the first 8 hours after PTH(1-84) injection.

While this represents an important advance in the treatment of the disease, Natpara has not demonstrated an ability to reduce incidences of hypercalcemia (elevated serum calcium levels), hypocalcemia (low serum calcium), or hypercalciuria (elevated urinary calcium) relative to conventional therapy in treated patients.

As such, there is a high need for improved PTH based therapies for hypoparathyroidism.

PTH(1-34), or teriparatide, was approved by the FDA in 2002 for the treatment of osteoporosis. Despite not being approved for this indication, PTH(1-34) has historically been used for treatment of hypoparathyroidism with patients receiving twice- or thrice-daily injections. To facilitate more physiological PTH levels, clinical studies have been conducted with PTH(1-34) administered by pump delivery in comparison with twice-daily injections. Over 6-months, pump delivery produced normal, steady state calcium levels with minimal fluctuation and avoided the rise in serum and urine calcium levels that are evident soon after PTH injection. The marked reduction in urinary calcium excretion when PTH(1-34) is administered by pump may indicate that PTH must be continuously exposed to the renal tubule for the renal calcium-conserving effects to be realized. Pump delivery of PTH(1-34) achieved simultaneous normalization of markers of bone turnover, serum calcium, and urine calcium excretion. These results were achieved with a 65 percent lower daily PTH(1-34) dose and a reduced need for magnesium supplementation compared with the twice daily PTH(1-34) injection regimen.

However, continuous pump therapy is inconvenient and challenging for patients, and it is an object of the current invention to provide for a more convenient therapeutic option of providing continuous exposure to PTH.

Long-term daily administration of PTH is associated with a progressive cortical bone loss due to increased bone metabolism. In a 6-year follow-up of patients treated with PTH(1-84) (Rubin, JCEM 2016) bone turnover markers remained greater than pretreatment values, peaking at the early years after PTH(1-84) initiation and declining thereafter but remaining significantly higher than baseline values by year 6. Bone mineral density (BMD) by dual X-ray absorptometry (DXA) was consistent with known site-specific effects of PTH, namely increases in lumbar spine and declines in the distal ⅓ radius. The decrease observed at the distal ⅓ radius is consistent with the known effects of intermittent PTH to increase cortical porosity and endosteal resorption.

It is an object of this invention to provide for a method of intermittently administering PTH, with improved control of serum and urine calcium, serum phosphorus, and lower elevation of bone turnover markers than currently applied PTH therapies. Preferably intermittent means with daily intervals, or more preferred with weekly intervals.

In the preclinical development program of both Forteo, PTH(1-34) and Natpara, PTH(1-84) a dose dependent increase in osteosarcoma rate was observed in rats treated with daily injections of the PTH compound. In the Natpara study, dosing of the high dose rats were discontinued due to excessive deaths in this group, primarily from metastatic osteosarcoma. This is felt to be due to the sensitivity of rats to the anabolic effects of intermittent PTH. In contrast, continuous exposure to PTH is known to lack significant bone anabolic activity. As such is an object of this invention to provide for an intermittent PTH replacement therapy that provides for an infusion-like profile of PTH, resulting in improved symptom control with a lower administered dose. Preferably intermittent means with daily intervals, or more preferred or alternatively with weekly intervals.

In summary, there is a need for a more convenient and safer treatment of hypoparathyroidism with reduced side-effects.

It is therefore an object of the present invention to at least partially overcome the shortcomings described above.

This object is achieved with a pharmaceutical composition comprising at least one controlled-release PTH compound or a pharmaceutically acceptable salt, hydrate or solvate thereof, for use in the treatment, control, delay or prevention of a condition that can be treated, controlled, delayed or prevented with PTH, wherein said pharmaceutical composition is administered no more frequent than once every 24 hours with a dosage of the controlled-release PTH compound that corresponds to no more than 70% of the molar equivalent dose of PTH 1-84 administered every 24 hours required to maintain serum calcium within normal levels over said 24 hour period in humans.

It was surprisingly found that such controlled-release PTH compound has a higher potency than PTH 1-84, so fewer molar equivalents need to be administered in a single administration to a patient to achieve beneficial serum calcium levels for at least 24 hours which improves efficacy and reduces the risks of side-effects.

It is understood that PTH 1-84 is the polypeptide with the sequence of SEQ ID NO:1.

Within the present invention the terms are used having the meaning as follows.

As used herein the terms "no more frequent than once every 24 hours" and "at least once every 24 hours" are used synonymously and mean that the time between two consecutive administrations is 24 hours or longer, meaning that there may for example be 24 hours, 48 hours, 72 hours, 96 hours, 120 hours, 144 hours or one week between two consecutive administrations.

As used herein the terms "within normal level" and "within the normal range" with regard to serum calcium levels refer to the calcium level ordinarily found in a subject of a given species, sex and age, provided as the range given by the lower limit of normal and the upper limit of normal. In humans, the normal level preferably corresponds to a serum calcium level of above 8.5 mg/dL (albumin-adjusted). In humans the upper limit of normal is below 10.5 mg/dL As used herein the term "serum calcium above 8.5 mg/dL" refers to albumin-adjusted calcium concentrations.

As used herein the term "albumin-adjusted" with regard to calcium levels means that the measured serum calcium level is corrected for calcium bound to albumin according to the following formula:

albumin-adjusted serum calcium (mg/dL)=measured total Ca (mg/dL)+0.8(4.0−serum albumin[g/dL])

As used herein the term "non-adjusted" with regard to calcium levels means that the measured total calcium concentration (mg/dL) is not adjusted for albumin-binding of calcium.

The term "molar equivalent dose" refers to the dose in which the controlled-release PTH compound comprises the same number of PTH molecules or PTH molecules as a particular dose of PTH 1-84 comprises PTH 1-84 molecules. For example, if a controlled-release PTH compound comprises one PTH molecule or PTH moiety per controlled-release PTH compound the molar equivalent dose is 1 controlled-release PTH compound for every 1 molecule of PTH 1-84. If a controlled-release PTH compound comprises two PTH molecules or PTH moieties per controlled-release PTH compound the molar equivalent dose is 1 controlled-release PTH compound for every 2 molecules of PTH 1-84.

As used herein the term "controlled-release PTH compound" refers to any compound, conjugate, crystal or admixture that comprises at least one PTH molecule or PTH moiety and from which the at least one PTH molecule or PTH moiety is released with a release half-life of at least 12 hours.

As used herein the terms "release half-life" and "half-life" refer to the time required under physiological conditions (i.e. aqueous buffer, pH 7.4, 37° C.) until half of all PTH or PTH moieties, respectively, comprised in a controlled-release PTH compound are released from said controlled-release PTH compound.

As used herein the term "PTH" refers all PTH polypeptides, preferably from mammalian species, more preferably from human and mammalian species, more preferably from human and murine species, as well as their variants, analogs, orthologs, homologs, and derivatives and fragments thereof, that are characterized by raising serum calcium and renal phosphorus excretion, and lowering serum phosphorus and renal calcium excretion. The term "PTH" also refers to all PTH-related polypeptides (PTHrP), such as the polypeptide of SEQ ID NO:121, that bind to and activate the common PTH/PTHrP1 receptor. Preferably, the term "PTH" refers to the PTH polypeptide of SEQ ID NO:51 as well as its variants, homologs and derivatives exhibiting essentially the same biological activity, i.e. raising serum calcium and renal phosphorus excretion, and lowering serum phosphorus and renal calcium excretion.

Preferably, the term "PTH" refers to the following polypeptide sequences:

(PTH 1-84)
SEQ ID NO: 1
SVSEIQLMHNLGKHLNSMERVEWLRKKLQDVHNFVALGAPLAPRDAGSQRPRKKED
NVLVESHEKSLGEADKADVNVLTKAKSQ (PTH 1-83)
SEQ ID NO: 2
SVSEIQLMHNLGKHLNSMERVEWLRKKLQDVHNFVALGAPLAPRDAGSQRPRKKED
NVLVESHEKSLGEADKADVNVLTKAKS

-continued (PTH 1-82)
                                               SEQ ID NO: 3
SVSEIQLMHNLGKHLNSMERVEWLRKKLQDVHNFVALGAPLAPRDAGSQRPRKKED
NVLVESHEKSLGEADKADVNVLTKAK (PTH 1-81)
                                               SEQ ID NO: 4
SVSEIQLMHNLGKHLNSMERVEWLRKKLQDVHNFVALGAPLAPRDAGSQRPRKKED
NVLVESHEKSLGEADKADVNVLTKA (PTH 1-80)
                                               SEQ ID NO: 5
SVSEIQLMHNLGKHLNSMERVEWLRKKLQDVHNFVALGAPLAPRDAGSQRPRKKED
NVLVESHEKSLGEADKADVNVLTK (PTH 1-79)
                                               SEQ ID NO: 6
SVSEIQLMHNLGKHLNSMERVEWLRKKLQDVHNFVALGAPLAPRDAGSQRPRKKED
NVLVESHEKSLGEADKADVNVLT (PTH 1-78)
                                               SEQ ID NO: 7
SVSEIQLMHNLGKHLNSMERVEWLRKKLQDVHNFVALGAPLAPRDAGSQRPRKKED
NVLVESHEKSLGEADKADVNVL (PTH 1-77)
                                               SEQ ID NO: 8
SVSEIQLMHNLGKHLNSMERVEWLRKKLQDVHNFVALGAPLAPRDAGSQRPRKKED
NVLVESHEKSLGEADKADVNV (PTH 1-76)
                                               SEQ ID NO: 9
SVSEIQLMHNLGKHLNSMERVEWLRKKLQDVHNFVALGAPLAPRDAGSQRPRKKED
NVLVESHEKSLGEADKADVN (PTH 1-75)
                                               SEQ ID NO: 10
SVSEIQLMHNLGKHLNSMERVEWLRKKLQDVHNFVALGAPLAPRDAGSQRPRKKED
NVLVESHEKSLGEADKADV (PTH 1-74)
                                               SEQ ID NO: 11
SVSEIQLMHNLGKHLNSMERVEWLRKKLQDVHNFVALGAPLAPRDAGSQRPRKKED
NVLVESHEKSLGEADKAD (PTH 1-73)
                                               SEQ ID NO: 12
SVSEIQLMHNLGKHLNSMERVEWLRKKLQDVHNFVALGAPLAPRDAGSQRPRKKED
NVLVESHEKSLGEADKA (PTH 1-72)
                                               SEQ ID NO: 13
SVSEIQLMHNLGKHLNSMERVEWLRKKLQDVHNFVALGAPLAPRDAGSQRPRKKED
NVLVESHEKSLGEADK (PTH 1-71)
                                               SEQ ID NO: 14
SVSEIQLMHNLGKHLNSMERVEWLRKKLQDVHNFVALGAPLAPRDAGSQRPRKKED
NVLVESHEKSLGEAD (PTH 1-70)
                                               SEQ ID NO: 15
SVSEIQLMHNLGKHLNSMERVEWLRKKLQDVHNFVALGAPLAPRDAGSQRPRKKED
NVLVESHEKSLGEA (PTH 1-69)
                                               SEQ ID NO: 16
SVSEIQLMHNLGKHLNSMERVEWLRKKLQDVHNFVALGAPLAPRDAGSQRPRKKED
NVLVESHEKSLGE (PTH 1-68)
                                               SEQ ID NO: 17
SVSEIQLMHNLGKHLNSMERVEWLRKKLQDVHNFVALGAPLAPRDAGSQRPRKKED
NVLVESHEKSLG (PTH 1-67)
                                               SEQ ID NO: 18
SVSEIQLMHNLGKHLNSMERVEWLRKKLQDVHNFVALGAPLAPRDAGSQRPRKKED
NVLVESHEKSL -continued (PTH 1-66)
SEQ ID NO: 19
SVSEIQLMHNLGKHLNSMERVEWLRKKLQDVHNFVALGAPLAPRDAGSQRPRKKED
NVLVESHEKS (PTH 1-65)
SEQ ID NO: 20
SVSEIQLMHNLGKHLNSMERVEWLRKKLQDVHNFVALGAPLAPRDAGSQRPRKKED
NVLVESHEK (PTH 1-64)
SEQ ID NO: 21
SVSEIQLMHNLGKHLNSMERVEWLRKKLQDVHNFVALGAPLAPRDAGSQRPRKKED
NVLVESHE (PTH 1-63)
SEQ ID NO: 22
SVSEIQLMHNLGKHLNSMERVEWLRKKLQDVHNFVALGAPLAPRDAGSQRPRKKED
NVLVESH (PTH 1-62)
SEQ ID NO: 23
SVSEIQLMHNLGKHLNSMERVEWLRKKLQDVHNFVALGAPLAPRDAGSQRPRKKED
NVLVES (PTH 1-61)
SEQ ID NO: 24
SVSEIQLMHNLGKHLNSMERVEWLRKKLQDVHNFVALGAPLAPRDAGSQRPRKKED
NVLVE (PTH 1-60)
SEQ ID NO: 25
SVSEIQLMHNLGKHLNSMERVEWLRKKLQDVHNFVALGAPLAPRDAGSQRPRKKED
NVLV (PTH 1-59)
SEQ ID NO: 26
SVSEIQLMHNLGKHLNSMERVEWLRKKLQDVHNFVALGAPLAPRDAGSQRPRKKED
NVL (PTH 1-58)
SEQ ID NO: 27
SVSEIQLMHNLGKHLNSMERVEWLRKKLQDVHNFVALGAPLAPRDAGSQRPRKKED
NV (PTH 1-57)
SEQ ID NO: 28
SVSEIQLMHNLGKHLNSMERVEWLRKKLQDVHNFVALGAPLAPRDAGSQRPRKKED
N (PTH 1-56)
SEQ ID NO: 29
SVSEIQLMHNLGKHLNSMERVEWLRKKLQDVHNFVALGAPLAPRDAGSQRPRKKED (PTH 1-55)
SEQ ID NO: 30
SVSEIQLMHNLGKHLNSMERVEWLRKKLQDVHNFVALGAPLAPRDAGSQRPRKKE (PTH 1-54)
SEQ ID NO: 31
SVSEIQLMHNLGKHLNSMERVEWLRKKLQDVHNFVALGAPLAPRDAGSQRPRKK (PTH 1-53)
SEQ ID NO: 32
SVSEIQLMHNLGKHLNSMERVEWLRKKLQDVHNFVALGAPLAPRDAGSQRPRK (PTH 1-52)
SEQ ID NO: 33
SVSEIQLMHNLGKHLNSMERVEWLRKKLQDVHNFVALGAPLAPRDAGSQRPR (PTH 1-51)
SEQ ID NO: 34
SVSEIQLMHNLGKHLNSMERVEWLRKKLQDVHNFVALGAPLAPRDAGSQRP (PTH 1-50)
SEQ ID NO: 35
SVSEIQLMHNLGKHLNSMERVEWLRKKLQDVHNFVALGAPLAPRDAGSQR -continued (PTH 1-49)  
SVSEIQLMHNLGKHLNSMERVEWLRKKLQDVHNFVALGAPLAPRDAGSQ  SEQ ID NO: 36

(PTH 1-48)  
SVSEIQLMHNLGKHLNSMERVEWLRKKLQDVHNFVALGAPLAPRDAGS  SEQ ID NO: 37

(PTH 1-47)  
SVSEIQLMHNLGKHLNSMERVEWLRKKLQDVHNFVALGAPLAPRDAG  SEQ ID NO: 38

(PTH 1-46)  
SVSEIQLMHNLGKHLNSMERVEWLRKKLQDVHNFVALGAPLAPRDA  SEQ ID NO: 39

(PTH 1-45)  
SVSEIQLMHNLGKHLNSMERVEWLRKKLQDVHNFVALGAPLAPRD  SEQ ID NO: 40

(PTH 1-44)  
SVSEIQLMHNLGKHLNSMERVEWLRKKLQDVHNFVALGAPLAPR  SEQ ID NO: 41

(PTH 1-43)  
SVSEIQLMHNLGKHLNSMERVEWLRKKLQDVHNFVALGAPLAP  SEQ ID NO: 42

(PTH 1-42)  
SVSEIQLMHNLGKHLNSMERVEWLRKKLQDVHNFVALGAPLA  SEQ ID NO: 43

(PTH 1-41)  
SVSEIQLMHNLGKHLNSMERVEWLRKKLQDVHNFVALGAPL  SEQ ID NO: 44

(PTH 1-40)  
SVSEIQLMHNLGKHLNSMERVEWLRKKLQDVHNFVALGAP  SEQ ID NO: 45

(PTH 1-39)  
SVSEIQLMHNLGKHLNSMERVEWLRKKLQDVHNFVALGA  SEQ ID NO: 46

(PTH 1-38)  
SVSEIQLMHNLGKHLNSMERVEWLRKKLQDVHNFVALG  SEQ ID NO: 47

(PTH 1-37)  
SVSEIQLMHNLGKHLNSMERVEWLRKKLQDVHNFVAL  SEQ ID NO: 48

(PTH 1-36)  
SVSEIQLMHNLGKHLNSMERVEWLRKKLQDVHNFVA  SEQ ID NO: 49

(PTH 1-35)  
SVSEIQLMHNLGKHLNSMERVEWLRKKLQDVHNFV  SEQ ID NO: 50

(PTH 1-34)  
SVSEIQLMHNLGKHLNSMERVEWLRKKLQDVHNF  SEQ ID NO: 51

(PTH 1-33)  
SVSEIQLMHNLGKHLNSMERVEWLRKKLQDVHN  SEQ ID NO: 52

(PTH 1-32)  
SVSEIQLMHNLGKHLNSMERVEWLRKKLQDVH  SEQ ID NO: 53

(PTH 1-31)  
SVSEIQLMHNLGKHLNSMERVEWLRKKLQDV  SEQ ID NO: 54

(PTH 1-30)  
SVSEIQLMHNLGKHLNSMERVEWLRKKLQD  SEQ ID NO: 55

-continued (PTH 1-29)
SEQ ID NO: 56
SVSEIQLMHNLGKHLNSMERVEWLRKKLQ (PTH 1-28)
SEQ ID NO: 57
SVSEIQLMHNLGKHLNSMERVEWLRKKL (PTH 1-27)
SEQ ID NO: 58
SVSEIQLMHNLGKHLNSMERVEWLRKK (PTH 1-26)
SEQ ID NO: 59
SVSEIQLMHNLGKHLNSMERVEWLRK (PTH 1-25)
SEQ ID NO: 60
SVSEIQLMHNLGKHLNSMERVEWLR (amidated PTH 1-84)
SEQ ID NO: 61
SVSEIQLMHNLGKHLNSMERVEWLRKKLQDVHNFVALGAPLAPRDAGSQRPRKKED
NVLVESHEKSLGEADKADVNVLTKAKSQ; wherein the C-terminus is amidated (amidated PTH 1-83)
SEQ ID NO: 62
SVSEIQLMHNLGKHLNSMERVEWLRKKLQDVHNFVALGAPLAPRDAGSQRPRKKED
NVLVESHEKSLGEADKADVNVLTKAKS; wherein the C-terminus is amidated (amidated PTH 1-82)
SEQ ID NO: 63
SVSEIQLMHNLGKHLNSMERVEWLRKKLQDVHNFVALGAPLAPRDAGSQRPRKKED
NVLVESHEKSLGEADKADVNVLTKAK; wherein the C-terminus is amidated (amidated PTH 1-81)
SEQ ID NO: 64
SVSEIQLMHNLGKHLNSMERVEWLRKKLQDVHNFVALGAPLAPRDAGSQRPRKKED
NVLVESHEKSLGEADKADVNVLTKA; wherein the C-terminus is amidated (amidated PTH 1-80)
SEQ ID NO: 65
SVSEIQLMHNLGKHLNSMERVEWLRKKLQDVHNFVALGAPLAPRDAGSQRPRKKED
NVLVESHEKSLGEADKADVNVLTK; wherein the C-terminus is amidated (amidated PTH 1-79)
SEQ ID NO: 66
SVSEIQLMHNLGKHLNSMERVEWLRKKLQDVHNFVALGAPLAPRDAGSQRPRKKED
NVLVESHEKSLGEADKADVNVLT; wherein the C-terminus is amidated (amidated PTH 1-78)
SEQ ID NO: 67
SVSEIQLMHNLGKHLNSMERVEWLRKKLQDVHNFVALGAPLAPRDAGSQRPRKKED
NVLVESHEKSLGEADKADVNVL; wherein the C-terminus is amidated (amidated PTH 1-77)
SEQ ID NO: 68
SVSEIQLMHNLGKHLNSMERVEWLRKKLQDVHNFVALGAPLAPRDAGSQRPRKKED
NVLVESHEKSLGEADKADVNV; wherein the C-terminus is amidated (amidated PTH 1-76)
SEQ ID NO: 69
SVSEIQLMHNLGKHLNSMERVEWLRKKLQDVHNFVALGAPLAPRDAGSQRPRKKED
NVLVESHEKSLGEADKADVN; wherein the C-terminus is amidated (amidated PTH 1-75)
SEQ ID NO: 70
SVSEIQLMHNLGKHLNSMERVEWLRKKLQDVHNFVALGAPLAPRDAGSQRPRKKED
NVLVESHEKSLGEADKADV; wherein the C-terminus is amidated (amidated PTH 1-74)
SEQ ID NO: 71
SVSEIQLMHNLGKHLNSMERVEWLRKKLQDVHNFVALGAPLAPRDAGSQRPRKKED
NVLVESHEKSLGEADKAD; wherein the C-terminus is amidated (amidated PTH 1-73)
SEQ ID NO: 72
SVSEIQLMHNLGKHLNSMERVEWLRKKLQDVHNFVALGAPLAPRDAGSQRPRKKED
NVLVESHEKSLGEADKA; wherein the C-terminus is amidated -continued (amidated PTH 1-72)

SEQ ID NO: 73

SVSEIQLMHNLGKHLNSMERVEWLRKKLQDVHNFVALGAPLAPRDAGSQRPRKKED
NVLVESHEKSLGEADK; wherein the C-terminus is amidated (amidated PTH 1-71)

SEQ ID NO: 74

SVSEIQLMHNLGKHLNSMERVEWLRKKLQDVHNFVALGAPLAPRDAGSQRPRKKED
NVLVESHEKSLGEAD; wherein the C-terminus is amidated (amidated PTH 1-70)

SEQ ID NO: 75

SVSEIQLMHNLGKHLNSMERVEWLRKKLQDVHNFVALGAPLAPRDAGSQRPRKKED
NVLVESHEKSLGEA; wherein the C-terminus is amidated (amidated PTH 1-69)

SEQ ID NO: 76

SVSEIQLMHNLGKHLNSMERVEWLRKKLQDVHNFVALGAPLAPRDAGSQRPRKKED
NVLVESHEKSLGE; wherein the C-terminus is amidated (amidated PTH 1-68)

SEQ ID NO: 77

SVSEIQLMHNLGKHLNSMERVEWLRKKLQDVHNFVALGAPLAPRDAGSQRPRKKED
NVLVESHEKSLG; wherein the C-terminus is amidated (amidated PTH 1-67)

SEQ ID NO: 78

SVSEIQLMHNLGKHLNSMERVEWLRKKLQDVHNFVALGAPLAPRDAGSQRPRKKED
NVLVESHEKSL; wherein the C-terminus is amidated (amidated PTH 1-66)

SEQ ID NO: 79

SVSEIQLMHNLGKHLNSMERVEWLRKKLQDVHNFVALGAPLAPRDAGSQRPRKKED
NVLVESHEKS; wherein the C-terminus is amidated (amidated PTH 1-65)

SEQ ID NO: 80

SVSEIQLMHNLGKHLNSMERVEWLRKKLQDVHNFVALGAPLAPRDAGSQRPRKKED
NVLVESHEK; wherein the C-terminus is amidated (amidated PTH 1-64)

SEQ ID NO: 81

SVSEIQLMHNLGKHLNSMERVEWLRKKLQDVHNFVALGAPLAPRDAGSQRPRKKED
NVLVESHE; wherein the C-terminus is amidated (amidated PTH 1-63)

SEQ ID NO: 82

SVSEIQLMHNLGKHLNSMERVEWLRKKLQDVHNFVALGAPLAPRDAGSQRPRKKED
NVLVESH; wherein the C-terminus is amidated (amidated PTH 1-62)

SEQ ID NO: 83

SVSEIQLMHNLGKHLNSMERVEWLRKKLQDVHNFVALGAPLAPRDAGSQRPRKKED
NVLVES; wherein the C-terminus is amidated (amidated PTH 1-61)

SEQ ID NO: 84

SVSEIQLMHNLGKHLNSMERVEWLRKKLQDVHNFVALGAPLAPRDAGSQRPRKKED
NVLVE; wherein the C-terminus is amidated (amidated PTH 1-60)

SEQ ID NO: 85

SVSEIQLMHNLGKHLNSMERVEWLRKKLQDVHNFVALGAPLAPRDAGSQRPRKKED
NVLV; wherein the C-terminus is amidated (amidated PTH 1-59)

SEQ ID NO: 86

SVSEIQLMHNLGKHLNSMERVEWLRKKLQDVHNFVALGAPLAPRDAGSQRPRKKED
NVL; wherein the C-terminus is amidated (amidated PTH 1-58)

SEQ ID NO: 87

SVSEIQLMHNLGKHLNSMERVEWLRKKLQDVHNFVALGAPLAPRDAGSQRPRKKED
NV; wherein the C-terminus is amidated (amidated PTH 1-57)

SEQ ID NO: 88

SVSEIQLMHNLGKHLNSMERVEWLRKKLQDVHNFVALGAPLAPRDAGSQRPRKKED
N; wherein the C-terminus is amidated

```
(amidated PTH 1-56)
                                              SEQ ID NO: 89
SVSEIQLMHNLGKHLNSMERVEWLRKKLQDVHNFVALGAPLAPRDAGSQRPRKKED;
wherein the C-terminus is amidated (amidated PTH 1-55)
                                              SEQ ID NO: 90
SVSEIQLMHNLGKHLNSMERVEWLRKKLQDVHNFVALGAPLAPRDAGSQRPRKKE;
wherein the C-terminus is amidated (amidated PTH 1-54)
                                              SEQ ID NO: 91
SVSEIQLMHNLGKHLNSMERVEWLRKKLQDVHNFVALGAPLAPRDAGSQRPRKK;
wherein the C-terminus is amidated (amidated PTH 1-53)
                                              SEQ ID NO: 92
SVSEIQLMHNLGKHLNSMERVEWLRKKLQDVHNFVALGAPLAPRDAGSQRPRK;
wherein the C-terminus is amidated (amidated PTH 1-52)
                                              SEQ ID NO: 93
SVSEIQLMHNLGKHLNSMERVEWLRKKLQDVHNFVALGAPLAPRDAGSQRPR;
wherein the C-terminus is amidated (amidated PTH 1-51)
                                              SEQ ID NO: 94
SVSEIQLMHNLGKHLNSMERVEWLRKKLQDVHNFVALGAPLAPRDAGSQRP;
wherein the C-terminus is amidated (amidated PTH 1-50)
                                              SEQ ID NO: 95
SVSEIQLMHNLGKHLNSMERVEWLRKKLQDVHNFVALGAPLAPRDAGSQR; wherein
the C-terminus is amidated (amidated PTH 1-49)
                                              SEQ ID NO: 96
SVSEIQLMHNLGKHLNSMERVEWLRKKLQDVHNFVALGAPLAPRDAGSQ; wherein
the C-terminus is amidated (amidated PTH 1-48)
                                              SEQ ID NO: 97
SVSEIQLMHNLGKHLNSMERVEWLRKKLQDVHNFVALGAPLAPRDAGS; wherein the
C-terminus is amidated (amidated PTH 1-47)
                                              SEQ ID NO: 98
SVSEIQLMHNLGKHLNSMERVEWLRKKLQDVHNFVALGAPLAPRDAG; wherein the
C-terminus is amidated (amidated PTH 1-46)
                                              SEQ ID NO: 99
SVSEIQLMHNLGKHLNSMERVEWLRKKLQDVHNFVALGAPLAPRDA; wherein the C-
terminus is amidated (amidated PTH 1-45)
                                              SEQ ID NO: 100
SVSEIQLMHNLGKHLNSMERVEWLRKKLQDVHNFVALGAPLAPRD; wherein the C-
terminus is amidated (amidated PTH 1-44)
                                              SEQ ID NO: 101
SVSEIQLMHNLGKHLNSMERVEWLRKKLQDVHNFVALGAPLAPR; wherein the C-
terminus is amidated (amidated PTH 1-43)
                                              SEQ ID NO: 102
SVSEIQLMHNLGKHLNSMERVEWLRKKLQDVHNFVALGAPLAP; wherein the C-
terminus is amidated (amidated PTH 1-42)
                                              SEQ ID NO: 103
SVSEIQLMHNLGKHLNSMERVEWLRKKLQDVHNFVALGAPLA; wherein the C-
terminus is amidated (amidated PTH 1-41)
                                              SEQ ID NO: 104
SVSEIQLMHNLGKHLNSMERVEWLRKKLQDVHNFVALGAPL; wherein the C-terminus
is amidated
```

-continued (amidated PTH 1-40)
SEQ ID NO: 105
SVSEIQLMHNLGKHLNSMERVEWLRKKLQDVHNFVALGAP; wherein the C-terminus
is amidated (amidated PTH 1-39)
SEQ ID NO: 106
SVSEIQLMHNLGKHLNSMERVEWLRKKLQDVHNFVALGA; wherein the C-terminus is
amidated (amidated PTH 1-38)
SEQ ID NO: 107
SVSEIQLMHNLGKHLNSMERVEWLRKKLQDVHNFVALG; wherein the C-terminus is
amidated (amidated PTH 1-37)
SEQ ID NO: 108
SVSEIQLMHNLGKHLNSMERVEWLRKKLQDVHNFVAL; wherein the C-terminus is
amidated (amidated PTH 1-36)
SEQ ID NO: 109
SVSEIQLMHNLGKHLNSMERVEWLRKKLQDVHNFVA; wherein the C-terminus is
amidated (amidated PTH 1-35)
SEQ ID NO: 110
SVSEIQLMHNLGKHLNSMERVEWLRKKLQDVHNFV; wherein the C-terminus is
amidated (amidated PTH 1-34)
SEQ ID NO: 111
SVSEIQLMHNLGKHLNSMERVEWLRKKLQDVHNF; wherein the C-terminus is
amidated (amidated PTH 1-33)
SEQ ID NO: 112
SVSEIQLMHNLGKHLNSMERVEWLRKKLQDVHN; wherein the C-terminus is
amidated (amidated PTH 1-32)
SEQ ID NO: 113
SVSEIQLMHNLGKHLNSMERVEWLRKKLQDVH; wherein the C-terminus is
amidated (amidated PTH 1-31)
SEQ ID NO: 114
SVSEIQLMHNLGKHLNSMERVEWLRKKLQDV; wherein the C-terminus is
amidated (amidated PTH 1-30)
SEQ ID NO: 115
SVSEIQLMHNLGKHLNSMERVEWLRKKLQD; wherein the C-terminus is amidated (amidated PTH 1-29)
SEQ ID NO: 116
SVSEIQLMHNLGKHLNSMERVEWLRKKLQ; wherein the C-terminus is amidated (amidated PTH 1-28)
SEQ ID NO: 117
SVSEIQLMHNLGKHLNSMERVEWLRKKL; wherein the C-terminus is amidated (amidated PTH 1-27)
SEQ ID NO: 118
SVSEIQLMHNLGKHLNSMERVEWLRKK; wherein the C-terminus is amidated (amidated PTH 1-26)
SEQ ID NO: 119
SVSEIQLMHNLGKHLNSMERVEWLRK; wherein the C-terminus is amidated (amidated PTH 1-25)
SEQ ID NO: 120
SVSEIQLMHNLGKHLNSMERVEWLR; wherein the C-terminus is amidated (PTHrP)
SEQ ID NO: 121
AVSEHQLLHDKGKSIQDLRRRFFLHHLIAEIHTAEIRATSEVSPNSKPSPNTKNHPVRF
GSDDEGRYLTQETNKVETYKEQPLKTPGKKKKGKPGKRKEQEKKKRRTRSAWLDS
GVTGSGLEGDHLSDTSTTSLELDSRRH More preferably, the term "PTH" refers to the sequence of SEQ ID:NOs 47, 48, 49, 50, 51, 52, 53, 54, 55, 107, 108, 109, 110, 111, 112, 113, 114 and 115. Even more preferably, the term "PTH" refers to the sequence of SEQ ID:NOs 50, 51, 52, 110, 111 and 112. In a particularly preferred embodiment the term "PTH" refers to the sequence of SEQ ID NO:51.

As used herein, the term "PTH polypeptide variant" refers to a polypeptide from the same species that differs from a reference PTH or PTHrP polypeptide. Preferably, such reference is a PTH polypeptide sequence and has the sequence of SEQ ID NO:51. Generally, differences are limited so that the amino acid sequence of the reference and the variant are closely similar overall and, in many regions, identical. Preferably, PTH polypeptide variants are at least 70%, 80%, 90%, or 95% identical to a reference PTH or PTHrP polypeptide, preferably to the PTH polypeptide of SEQ ID NO:51. By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. These alterations of the reference sequence may occur at the amino (N-terminal) or carboxy terminal (C-terminal) positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein. Preferably, the query sequence is the sequence of SEQ ID NO:51.

Such PTH polypeptide variants may be naturally occurring variants, such as naturally occurring allelic variants encoded by one of several alternate forms of a PTH or PTHrP occupying a given locus on a chromosome or an organism, or isoforms encoded by naturally occurring splice variants originating from a single primary transcript. Alternatively, a PTH polypeptide variant may be a variant that is not known to occur naturally and that can be made by mutagenesis techniques known in the art.

It is known in the art that one or more amino acids may be deleted from the N-terminus or C-terminus of a bioactive polypeptide without substantial loss of biological function. Such N- and/or C-terminal deletions are also encompassed by the term PTH polypeptide variant.

It is also recognized by one of ordinary skill in the art that some amino acid sequences of PTH or PTHrP polypeptides can be varied without significant effect of the structure or function of the polypeptide. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, which is hereby incorporated by reference in its entirety, wherein the authors indicate that there are two main approaches for studying the tolerance of the amino acid sequence to change.

The term PTH polypeptide also encompasses all PTH and PTHrP polypeptides encoded by PTH and PTHrP analogs, orthologs, and/or species homologs. It is also recognized by one of ordinary skill in the art that PTHrP and PTHrP analogs bind to activate the common PTH/PTHrP1 receptor, so the term PTH polypeptide also encompasses all PTHrP analogs. As used herein, the term "PTH analog" refers to PTH and PTHrP of different and unrelated organisms which perform the same functions in each organism but which did not originate from an ancestral structure that the organisms' ancestors had in common. Instead, analogous PTH and PTHrP arose separately and then later evolved to perform the same or similar functions. In other words, analogous PTH and PTHrP polypeptides are polypeptides with quite different amino acid sequences but that perform the same biological activity, namely raising serum calcium and renal phosphorus excretion, and lowering serum phosphorus and renal calcium excretion.

As used herein the term "PTH ortholog" refers to PTH and PTHrP within two different species which sequences are related to each other via a common homologous PTH or PTHrP in an ancestral species, but which have evolved to become different from each other.

As used herein, the term "PTH homolog" refers to PTH and PTHrP of different organisms which perform the same functions in each organism and which originate from an ancestral structure that the organisms' ancestors had in common. In other words, homologous PTH polypeptides are polypeptides with quite similar amino acid sequences that perform the same biological activity, namely raising serum calcium and renal phosphorus excretion, and lowering serum phosphorus and renal calcium excretion. Preferably, PTH polypeptide homologs may be defined as polypeptides exhibiting at least 40%, 50%, 60%, 70%, 80%, 90% or 95% identity to a reference PTH or PTHrP polypeptide, preferably the PTH polypeptide of SEQ ID NO:51.

Thus, a PTH polypeptide according to the invention may be, for example: (i) one in which at least one of the amino acids residues is substituted with a conserved or non-conserved amino acid residue, preferably a conserved amino acid residue, and such substituted amino acid residue may or may not be one encoded by the genetic code; and/or (ii) one in which at least one of the amino acid residues includes a substituent group; and/or (iii) one in which the PTH polypeptide is fused with another compound, such as a compound to increase the half-life of the polypeptide (for example, polyethylene glycol); and/or (iv) one in which additional amino acids are fused to the PTH polypeptide, such as an IgG Fc fusion region polypeptide or leader or secretory sequence or a sequence which is employed for purification of the above form of the polypeptide or a pre-protein sequence.

As used herein, the term "PTH polypeptide fragment" refers to any polypeptide comprising a contiguous span of a part of the amino acid sequence of a PTH or PTHrP polypeptide, preferably the polypeptide of SEQ ID NO:51.

More specifically, a PTH polypeptide fragment comprises at least 6, such as at least 8, at least 10 or at least 17 consecutive amino acids of a PTH or PTHrP polypeptide, more preferably of the polypeptide of SEQ ID NO:51. A PTH polypeptide fragment may additionally be described as sub-genuses of PTH or PTHrP polypeptides comprising at least 6 amino acids, wherein "at least 6" is defined as any integer between 6 and the integer representing the C-terminal amino acid of a PTH or PTHrP polypeptide, preferably of the polypeptide of SEQ ID No:51. Further included are species of PTH or PTHrP polypeptide fragments at least 6 amino acids in length, as described above, that are further specified in terms of their N-terminal and C-terminal positions. Also encompassed by the term "PTH polypeptide fragment" as individual species are all PTH or PTHrP polypeptide fragments, at least 6 amino acids in length, as described above, that may be particularly specified by a N-terminal and C-terminal position. That is, every combination of a N-terminal and C-terminal position that a fragment at least 6 contiguous amino acid residues in length could occupy, on any given amino acid sequence of a PTH or PTHrP polypeptide, preferably the PTH polypeptide of SEQ ID:N051, is included in the present invention.

The term "PTH" also includes poly(amino acid) conjugates which have a sequence as described above, but having a backbone that comprises both amide and non-amide linkages, such as ester linkages, like for example depsipeptides. Depsipeptides are chains of amino acid residues in which the backbone comprises both amide (peptide) and ester bonds. Accordingly, the term "side chain" as used herein refers either to the moiety attached to the alpha-carbon of an amino acid moiety, if the amino acid moiety is connected through amine bonds such as in polypeptides, or to any carbon atom-comprising moiety attached to the backbone of a poly(amino acid) conjugate, such as for example in the case of depsipeptides. Preferably, the term "PTH" refers to polypeptides having a backbone formed through amide (peptide) bonds.

As the term PTH includes the above-described variants, analogs, orthologs, homologs, derivatives and fragments of PTH and PTHrP, all references to specific positions within a reference sequence also include the equivalent positions in variants, analogs, orthologs, homologs, derivatives and fragments of a PTH or PTHrP moiety, even if not specifically mentioned.

As used herein the term "micelle" means an aggregate of amphiphilic molecules dispersed in a liquid colloid. In aqueous solution a typical micelle forms an aggregate with the hydrophilic moiety of the surfactant molecules facing the surrounding solvent and the hydrophobic moiety of the surfactant molecule facing inwards, also called "normal-phase micelle". "Invers micelles" have the hydrophilic moiety facing inwards and the hydrophobic moiety facing the surrounding solvent.

As used herein the term "liposome" refers to a vesicle, preferably a spherical vesicle, having at least one lipid bilayer. Preferably, liposomes comprise phospholipids, even more preferably phosphatidylcholine. The term "liposome" refers to various structures and sizes, such as, for example, to multilamellar liposome vesicles (MLV) having more than one concentric lipid bilayer with an average diameter of 100 to 1000 nm, small unilamellar liposome vesicles (SUV) having one lipid bilayer and an average diameter of 25 to 100 nm, large unilamellar liposome vesicles (LUV) having one lipid bilayer and an average diameter of about 1000 μm and giant unilamellar vesicles (GUV) having one lipid bilayer and an average diameter of 1 to 100 μm. The term "liposome" also includes elastic vesicles such as transferosomes and ethosomes, for example.

As used herein the term "aquasome" refers to spherical nanoparticles having a diameter of 60 to 300 nm that comprise at least three layers of self-assembled structure, namely a solid phase nanocrystalline core coated with an oligomeric film to which drug molecules are adsorbed with or without modification of the drug.

As used herein the term "ethosome" refers to lipid vesicles comprising phospholipids and ethanol and/or isopropanol in relatively high concentration and water, having a size ranging from tens of nanometers to micrometers.

As used herein the term "LeciPlex" refers to positively charged phospholipid-based vesicular system which comprises soy PC, a cationic agent, and a bio-compatible solvent like PEG 300, PEG 400, diethylene glycol monoethyl ether, tetrahydrofurfuryl alcohol polyethylene glycol ether or 2-pyrrolidoneor N-methyl-2-pyrrolidone.

As used herein the term "niosome" refers to unilamellar or multilamellar vesicles comprising non-ionic surfactants.

As used herein the term "pharmacosome" refers to ultrafine vesicular, micellar or hexagonal aggregates from lipids covalently bound to biologically active moieties.

As used herein the term "proniosome" refers to dry formulations of surfactant-coated carrier which on rehydration and mild agitation gives niosomes.

As used herein the term "polymersome" refers to an artificial spherical vesicle comprising a membrane formed from amphiphilic synthetic block copolymers and may optionally comprise an aqueous solution in its core. A polymersome has a diameter ranging from 50 nm to 5 μm and larger. The term also includes syntosomes, which are polymersomes engineered to comprise channels that allow certain chemicals to pass through the membrane into or out of the vesicle.

As used herein the term "sphingosome" refers to a concentric, bilayered vesicle in which an aqueous volume is entirely enclosed by a membranous lipid bilayer mainly composed of natural or synthetic sphingolipid.

As used herein the term "transferosome" refers to ultraflexible lipid vesicles comprising an aqueous core that are formed from a mixture of common polar and suitable edge-activated lipids which facilitate the formation of highly curved bilayers which render the transferosome highly deformable.

As used herein the term "ufasome" refers to a vesicle comprising unsaturated fatty acids.

As used herein the term "polypeptide" refers to a peptide comprising up to and including 50 amino acid monomers.

As used herein the term "protein" refers to a peptide of more than 50 amino acid residues. Preferably a protein comprises at most 20000 amino acid residues, such as at most 15000 amino acid residues, such as at most 10000 amino acid residues, such as at most 5000 amino acid residues, such as at most 4000 amino acid residues, such as at most 3000 amino acid residues, such as at most 2000 amino acid residues, such as at most 1000 amino acid residues.

As used herein the term "physiological conditions" refers to an aqueous buffer at pH 7.4, 37° C.

As used herein the term "pharmaceutical composition" refers to a composition containing one or more active ingredients, such as for example at least one controlled-release PTH compounds, and one or more excipients, as well as any product which results, directly or indirectly, from combination, complexation or aggregation of any two or more of the ingredients of the composition, or from dissociation of one or more of the ingredients, or from other types of reactions or interactions of one or more of the ingredients. Accordingly, the pharmaceutical compositions for use of the present invention encompass any composition made by admixing one or more controlled-release PTH compound and a pharmaceutically acceptable excipient.

As used herein the term "liquid composition" refers to a mixture comprising water-soluble controlled-release PTH compound and one or more solvents, such as water.

The term "suspension composition" relates to a mixture comprising water-insoluble controlled-release PTH compound and one or more solvents, such as water.

As used herein, the term "dry composition" means that a pharmaceutical composition is provided in a dry form. Suitable methods for drying are spray-drying and lyophilization, i.e. freeze-drying. Such dry composition of prodrug has a residual water content of a maximum of 10%, preferably less than 5% and more preferably less than 2%, determined according to Karl Fischer. Preferably, the pharmaceutical composition for use of the present invention is dried by lyophilization.

The term "drug" as used herein refers to a substance, such as PTH, used in the treatment, cure, prevention, or diagnosis of a disease or used to otherwise enhance physical or mental well-being. If a drug is conjugated to another moiety, the moiety of the resulting product that originated from the drug is referred to as "biologically active moiety".

As used herein the term "prodrug" refers to a conjugate in which a biologically active moiety is reversibly and covalently connected to a specialized protective group through a reversible linker moiety, also referred to as "reversible prodrug linker moiety", which comprises a reversible linkage with the biologically active moiety and wherein the specialized protective group alters or eliminates undesirable properties in the parent molecule. This also includes the enhancement of desirable properties in the drug and the suppression of undesirable properties. The specialized non-toxic protective group is referred to as "carrier". A prodrug releases the reversibly and covalently bound biologically active moiety in the form of its corresponding drug. In other words, a prodrug is a conjugate comprising a biologically active moiety which is covalently and reversibly conjugated to a carrier moiety via a reversible prodrug linker moiety, which covalent and reversible conjugation of the carrier to the reversible prodrug linker moiety is either directly or through a spacer. Such conjugate releases the formerly conjugated biologically active moiety in the form of a free unmodified drug.

A "biodegradable linkage" or a "reversible linkage" is a linkage that is hydrolytically degradable, i.e. cleavable, in the absence of enzymes under physiological conditions (aqueous buffer at pH 7.4, 37° C.) with a half-life ranging from one hour to three months, preferably from one hour to two months, even more preferably from one hour to one month, even more preferably from one hour to three weeks, most preferably from one hour to two weeks. Accordingly, a stable linkage is a linkage having a half-life under physiological conditions (aqueous buffer at pH 7.4, 37° C.) of more than three months.

As used herein, the term "traceless prodrug linker" means a reversible prodrug linker, i.e. a linker moiety reversibly and covalently connecting the biologically active moiety with the carrier, which upon cleavage releases the drug in its free form. As used herein, the term "free form" of a drug means the drug in its unmodified, pharmacologically active form.

As used herein, the term "excipient" refers to a diluent, adjuvant, or vehicle with which the therapeutic, such as a drug or prodrug, is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such compositions will contain a therapeutically effective amount of the drug or biologically active moiety, together with a suitable amount of excipient so as to provide the form for proper administration to the patient. The formulation should suit the mode of administration.

As used herein, the term "reagent" means a chemical compound which comprises at least one functional group for reaction with the functional group of another chemical compound or drug. It is understood that a drug comprising a functional group (such as a primary or secondary amine or hydroxyl functional group) is also a reagent.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety. Accordingly, a biologically active moiety is released from a prodrug as a drug.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N($R^1$)—" can be attached to two moieties or interrupting a moiety either as "—C(O)N($R^1$)—" or as "—N($R^1$)C(O)—". Similarly, a moiety

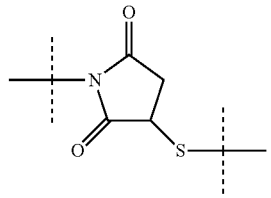

can be attached to two moieties or can interrupt a moiety either as

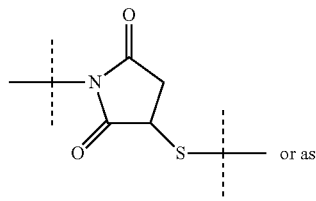

or as

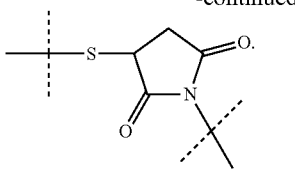

As used herein, the term "functional group" means a group of atoms which can react with other groups of atoms. Functional groups include but are not limited to the following groups: carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxyl (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, sulfonamides, sulfuric acid, vinyl sulfone, vinyl ketone, diazoalkane, oxirane, and aziridine.

In case the controlled-release PTH compound for use of the present invention comprise one or more acidic or basic groups, the invention also comprises their corresponding pharmaceutically or toxicologically acceptable salts, in particular their pharmaceutically utilizable salts. Thus, the controlled-release PTH compound for use of the present invention comprising acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Controlled-release PTH compound for use of the present invention comprising one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the controlled-release PTH compound for use of the present invention simultaneously comprise acidic and basic groups, the invention also includes, in addition to the salt forms mentioned, inner salts or betaines (zwitterions). The respective salts can be obtained by customary methods which are known to the person skilled in the art like, for example by contacting these compounds with an organic or inorganic acid or base in a solvent or dispersant, or by anion exchange or cation exchange with other salts. The present invention also includes all salts of the compounds for use of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means a substance that does cause harm when administered to a patient and preferably means approved by a regulatory agency, such as the EMA (Europe) and/or the FDA (US) and/or any other national regulatory agency for use in animals, preferably for use in humans.

As used herein the term "about" in combination with a numerical value is used to indicate a range ranging from and including the numerical value plus and minus no more than 10% of said numerical value, more preferably no more than 8% of said numerical value, even more preferably no more than 5% of said numerical value and most preferably no more than 2% of said numerical value. For example, the phrase "about 200" is used to mean a range ranging from and including 200+/−10%, i.e. ranging from and including 180 to 220; preferably 200+/−8%, i.e. ranging from and including 184 to 216; even more preferably ranging from and including 200+/−5%, i.e. ranging from and including 190 to 210; and most preferably 200+/−2%, i.e. ranging from and including 196 to 204. It is understood that a percentage given as "about 20%" does not mean "20%+/−10%", i.e. ranging from and including 10 to 30%, but "about 20%" means ranging from and including 18 to 22%, i.e. plus and minus 10% of the numerical value which is 20.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical groups and/or moieties, such as, for example, one or more functional groups. Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferable has a molecular weight of at most 1000 kDa, such as at most 750 kDa, such as at most 500 kDa, such as at most 300 kDa, such as at most 200 kDa, such as at most 100 kDa. It is understood that for insoluble polymers, such as hydrogels, no meaningful molecular weight ranges can be provided. It is understood that also a protein is a polymer in which the amino acids are the repeating structural units, even though the side chains of each amino acid may be different.

As used herein, the term "polymeric" means a reagent or a moiety comprising one or more polymers or polymer moieties. A polymeric reagent or moiety may optionally also comprise one or more other moiety/moieties, which are preferably selected from the group consisting of:

C$_{1-50}$ alkyl, C$_{2-50}$ alkenyl, C$_{2-50}$ alkynyl, C$_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

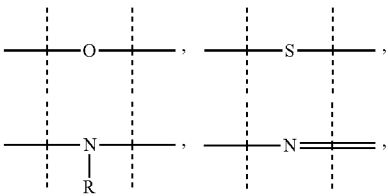

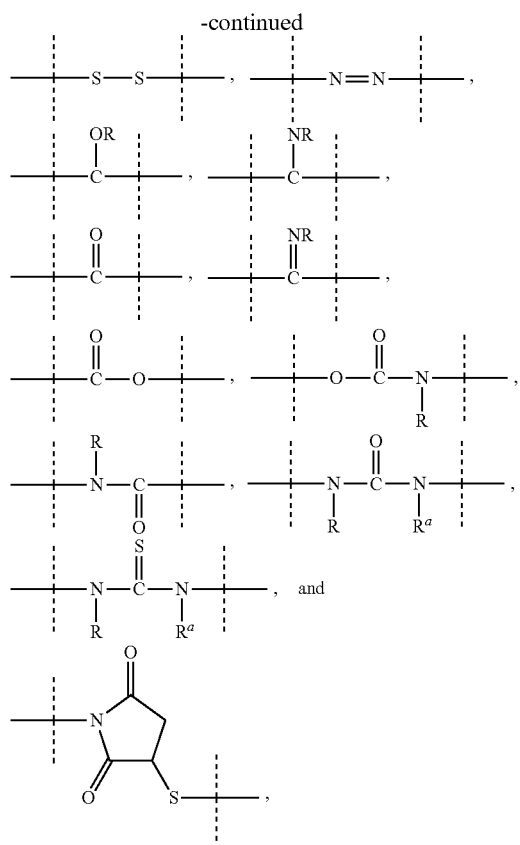

wherein
dashed lines indicate attachment to the remainder of the moiety or reagent, and
—R and —$R^a$ are independently of each other selected from the group consisting of —H, methyl, ethyl, propyl, butyl, pentyl and hexyl.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising "x" monomer units any integer given for "x" therefore corresponds to the arithmetic mean number of monomers. Any range of integers given for "x" provides the range of integers in which the arithmetic mean numbers of monomers lies. An integer for "x" given as "about x" means that the arithmetic mean numbers of monomers lies in a range of integers of x+/−10%, preferably x+/−8%, more preferably x+/−5% and most preferably x+/−2%.

As used herein, the term "number average molecular weight" means the ordinary arithmetic mean of the molecular weights of the individual polymers.

As used herein the term "water-soluble" with reference to a carrier means that when such carrier is part of the controlled-release PTH compound for use of the present invention at least 1 g of the controlled-release PTH compound comprising such water-soluble carrier can be dissolved in one liter of water at 20° C. to form a homogeneous solution. Accordingly, the term "water-insoluble" with reference to a carrier means that when such carrier is part of a controlled-release PTH compound for use of the present invention less than 1 g of the controlled-release PTH compound comprising such water-insoluble carrier can be dissolved in one liter of water at 20° C. to form a homogeneous solution.

As used herein the term "water-soluble" with reference to the controlled-release PTH compound means that at least 1 g of the controlled-release PTH compound can be dissolved in one liter of water at 20° C. to form a homogeneous solution. Accordingly, the term "water-insoluble" with reference to the controlled-release PTH compound means that less than 1 g of the controlled-release PTH compound can be dissolved in one liter of water at 20° C. to form a homogeneous solution.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity.

As used herein the term "thermogelling" means a compound that is a liquid or a low viscosity solution having a viscosity of less than 500 cps at 25° C. at a shear rate of about 0.1/second at a low temperature, which low temperature ranges between about 0° C. to about 10° C., but which is a higher viscosity compound of less than 10000 cps at 25° C. at a shear rate of about 0.1/second at a higher temperature, which higher temperature ranges between about 30° C. to about 40° C., such as at about 37° C.

As used herein, the term "PEG-based" in relation to a moiety or reagent means that said moiety or reagent comprises PEG. Preferably, a PEG-based moiety or reagent comprises at least 10% (w/w) PEG, such as at least 20% (w/w) PEG, such as at least 30% (w/w) PEG, such as at least 40% (w/w) PEG, such as at least 50% (w/w), such as at least 60 (w/w) PEG, such as at least 70% (w/w) PEG, such as at least 80% (w/w) PEG, such as at least 90% (w/w) PEG, such as at least 95%. The remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and
linkages selected from the group comprising

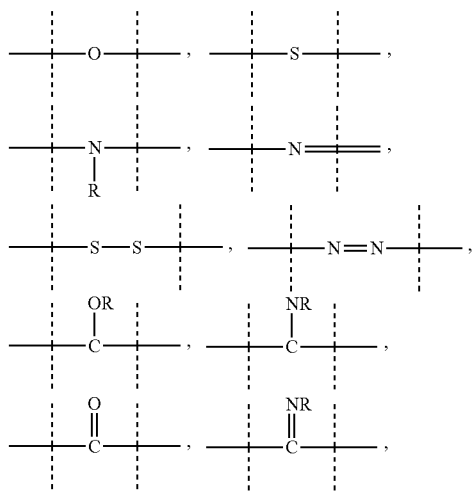

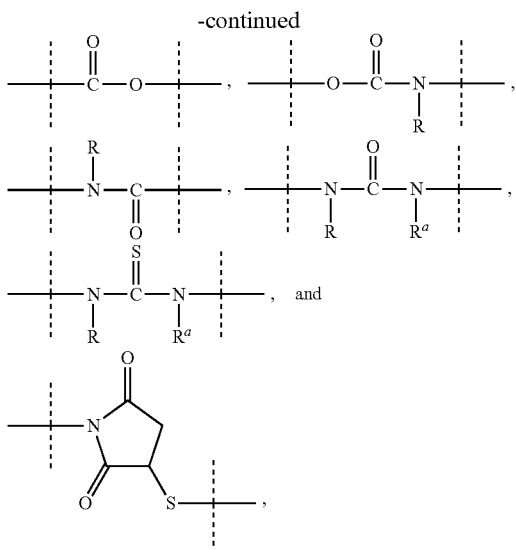

wherein
dashed lines indicate attachment to the remainder of the moiety or reagent, and —R and —R$^a$ are independently of each other selected from the group consisting of —H, methyl, ethyl, propyl, butyl, pentyl and hexyl.

As used herein, the term "PEG-based comprising at least X % PEG" in relation to a moiety or reagent means that said moiety or reagent comprises at least X % (w/w) ethylene glycol units (—CH$_2$CH$_2$O—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

C$_{1-50}$ alkyl, C$_{2-50}$ alkenyl, C$_{2-50}$ alkynyl, C$_{3-10}$ cycloalkyl, 3- to 10-membered heterocyclyl, 8- to 11-membered heterobicyclyl, phenyl, naphthyl, indenyl, indanyl, and tetralinyl; and
linkages selected from the group comprising

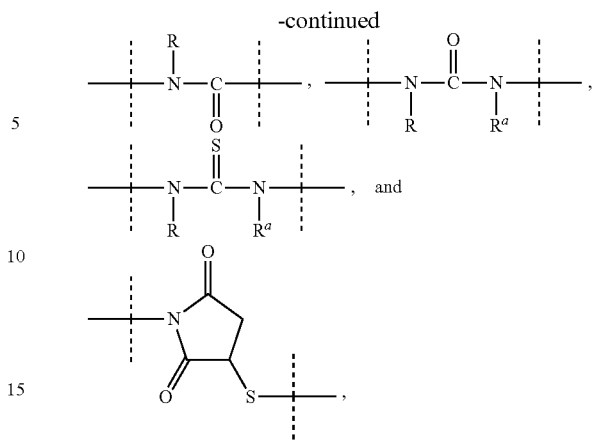

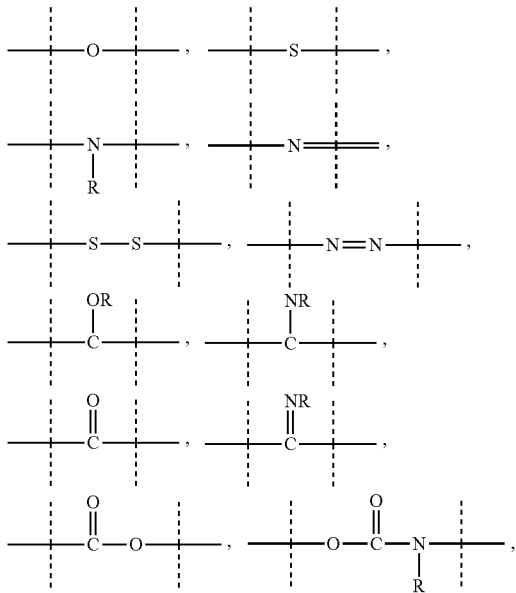

wherein
dashed lines indicate attachment to the remainder of the moiety or reagent, and —R and —R$^a$ are independently of each other selected from the group consisting of —H, methyl, ethyl, propyl, butyl, pentyl and hexyl.

The term "hyaluronic acid-based comprising at least X % hyaluronic acid" is used accordingly.

The term "substituted" as used herein means that one or more —H atom(s) of a molecule or moiety are replaced by a different atom or a group of atoms, which are referred to as "substituent".

Preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)$_2$N(R$^{x3}$)—;

—R$^{x1}$, —R$^{x1a}$, —R$^{x1b}$ are independently of each other selected from the group consisting of —H, -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —$R^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)(S(O)R$^{x4a}$, —N(R$^{x4}$)C(O)OR$^{x4a}$, —N(R$^{x4}$)C(O)R$^{x4a}$R$^{x4b}$), —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$) and C$_{1-6}$ alkyl; wherein C$_{1-6}$ alkyl is optionally substituted with one or more halogen, which are the same or different;

each —$R^{x3}$, —$R^{x3a}$, —$R^{x4}$, —$R^{x4a}$, —$R^{x4b}$ is independently selected from the group consisting of —H and C$_{1-6}$ alkyl; wherein C$_{1-6}$ alkyl is optionally substituted with one or more halogen, which are the same or different.

More preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1}$a), -T$^0$, C$_{1-10}$ alkyl, C$_{2-10}$ alkenyl, and C$_{2-10}$ alkynyl; wherein -T$^0$, C$_{1-10}$ alkyl, C$_{2-10}$ alkenyl, and C$_{2-10}$ alkynyl are optionally substituted with one or more —$R^{x2}$, which are the same or different and wherein C$_{1-10}$ alkyl, C$_{2-10}$ alkenyl, and C$_{2-10}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —$R^{x1}$, —$R^{x1a}$, —$R^{x1b}$, —$R^{x3}$, $R^{x3a}$ is independently selected from the group consisting of —H, halogen, C$_{1-6}$ alkyl, C$_{2-6}$ alkenyl, and C$_{2-6}$ alkynyl;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —$R^{x2}$, which are the same or different;

each —$R^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$C(O)R$^{x4}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different;

each —$R^{x4}$, —$R^{x4a}$, —$R^{x4b}$ is independently selected from the group consisting of —H, halogen, C$_{1-6}$ alkyl, C$_{2-6}$ alkenyl, and C$_{2-6}$ alkynyl;

Even more preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)R$^{x1a}$, —N(R$^{x1}$)C(O)R$^{x1a}$, —N(R$^{x1}$)C(O)N(R$^{x1a}$R$^{x1b}$), —OC(O)N(R$^{x1}$R$^{x1a}$), -T$^0$, C$_{1-6}$ alkyl, C$_{2-6}$ alkenyl, and C$_{2-6}$ alkynyl; wherein -T$^0$, C$_{1-6}$ alkyl, C$_{2-6}$ alkenyl, and C$_{2-6}$ alkynyl are optionally substituted with one or more —$R^{x2}$, which are the same or different and wherein C$_{1-6}$ alkyl, C$_{2-6}$ alkenyl, and C$_{2-6}$ alkynyl are optionally interrupted by one or more groups selected from the group consisting of -T$^0$—, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —$R^{x1}$, —$R^{x1a}$, —$R^{x1b}$, $R^{x2}$, —$R^{x3}$, —$R^{x3a}$ is independently selected from the group consisting of —H, halogen, C$_{1-6}$ alkyl, C$_{2-6}$ alkenyl, and C$_{2-6}$ alkynyl;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —$R^{x2}$, which are the same or different.

Preferably, a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

The term "interrupted" means that a moiety is inserted between two carbon atoms or—if the insertion is at one of the moiety's ends—between a carbon or heteroatom and a hydrogen atom, preferably between a carbon and a hydrogen atom.

As used herein, the term "C$_{1-4}$ alkyl" alone or in combination means a straight-chain or branched alkyl moiety having 1 to 4 carbon atoms. If present at the end of a molecule, examples of straight-chain or branched C$_{1-4}$ alkyl are methyl, ethyl, n-propyl, isopropyl, n-butyl, isobutyl, sec-butyl and tert-butyl. When two moieties of a molecule are linked by the C$_{1-4}$ alkyl, then examples for such C$_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—. Each hydrogen of a C$_{1-4}$ alkyl carbon may optionally be replaced by a substituent as defined above. Optionally, a C$_{1-4}$ alkyl may be interrupted by one or more moieties as defined below.

As used herein, the term "C$_{1-6}$ alkyl" alone or in combination means a straight-chain or branched alkyl moiety having 1 to 6 carbon atoms. If present at the end of a molecule, examples of straight-chain and branched C$_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the C$_{1-6}$ alkyl group, then examples for such C$_{1-6}$ alkyl groups are —CH$_2$—, —CH$_2$—CH$_2$—, —CH(CH$_3$)—, —CH$_2$—CH$_2$—CH$_2$—, —CH(C$_2$H$_5$)— and —C(CH$_3$)$_2$—. Each hydrogen atom of a C$_{1-6}$ carbon may optionally be replaced by a substituent as defined above. Optionally, a C$_{1-6}$ alkyl may be interrupted by one or more moieties as defined below.

Accordingly, "C$_{1-10}$ alkyl", "C$_{1-20}$ alkyl" or "C$_{1-50}$ alkyl" means an alkyl chain having 1 to 10, 1 to 20 or 1 to 50 carbon atoms, respectively, wherein each hydrogen atom of the C$_{1-10}$, C$_{1-20}$ or C$_{1-50}$ carbon may optionally be replaced by a substituent as defined above. Optionally, a C$_{1-10}$ or C$_{1-50}$ alkyl may be interrupted by one or more moieties as defined below.

As used herein, the term "C$_{2-6}$ alkenyl" alone or in combination means a straight-chain or branched hydrocarbon moiety comprising at least one carbon-carbon double bond having 2 to 6 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the C$_{2-6}$ alkenyl group, then an example for such C$_{2-6}$ alkenyl is —CH=CH—. Each hydrogen atom of a C$_{2-6}$ alkenyl moiety may optionally be replaced by a substituent as defined above. Optionally, a C$_{2-6}$ alkenyl may be interrupted by one or more moieties as defined below.

Accordingly, the term "C$_{2-10}$ alkenyl", "C$_{2-20}$ alkenyl" or "C$_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a C$_{2-10}$ alkenyl, C$_{2-20}$ alkenyl or C$_{2-50}$ alkenyl group may optionally be replaced by a substituent as defined above. Optionally, a C$_{2-10}$ alkenyl, C$_{2-20}$ alkenyl or C$_{2-50}$ alkenyl may be interrupted by one or more moieties as defined below.

As used herein, the term "C$_{2-6}$ alkynyl" alone or in combination means straight-chain or branched hydrocarbon moiety comprising at least one carbon-carbon triple bond having 2 to 6 carbon atoms. If present at the end of a molecule, examples are —C≡CH, —CH$_2$—C≡CH, CH$_2$—CH$_2$—C≡CH and CH$_2$—C≡C—CH$_3$. When two moieties of a molecule are linked by the alkynyl group, then an example is —C≡C—. Each hydrogen atom of a C$_{2-6}$ alkynyl group may optionally be replaced by a substituent as defined above. Optionally, one or more double bond(s) may occur. Optionally, a C$_{2-6}$ alkynyl may be interrupted by one or more moieties as defined below.

Accordingly, as used herein, the term "C$_{2-10}$ alkynyl", "C$_{2-20}$ alkynyl" and "C$_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a C$_{2-10}$ alkynyl, C$_{2-20}$ alkynyl or C$_{2-50}$ alkynyl group may optionally be replaced by a substituent as defined above. Optionally, one or more double bond(s) may occur. Optionally, a C$_{2-10}$ alkynyl, C$_{2-20}$ alkynyl or C$_{2-50}$ alkynyl may be interrupted by one or more moieties as defined below.

As mentioned above, a C$_{1-4}$ alkyl, C$_{1-6}$ alkyl, C$_{1-10}$ alkyl, C$_{1-20}$ alkyl, C$_{1-50}$ alkyl, C$_{2-6}$ alkenyl, C$_{2-10}$ alkenyl, C$_{2-20}$ alkenyl, C$_{2-50}$ alkenyl, C$_{2-6}$ alkynyl, C$_{2-10}$ alkynyl, C$_{2-20}$ alkynyl or C$_{2-50}$ alkynyl may optionally be interrupted by one or more moieties which are preferably selected from the group consisting of

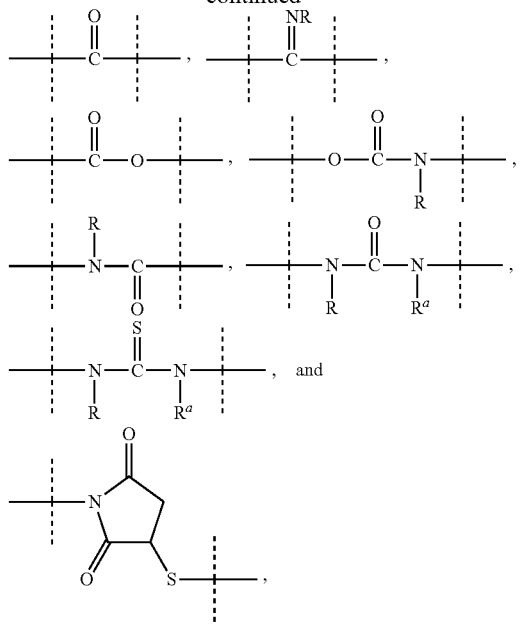

wherein
dashed lines indicate attachment to the remainder of the moiety or reagent; and —R and —R$^a$ are independently of each other selected from the group consisting of —H, methyl, ethyl, propyl, butyl, pentyl and hexyl.

As used herein, the term "C$_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a C$_{3-10}$ cycloalkyl carbon may be replaced by a substituent as defined above. The term "C$_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

It is understood that the phrase "the pair $R^x/R^y$ is joined together with the atom to which they are attached to form a $C_{3-10}$ cycloalkyl or a 3- to 10-membered heterocyclyl" in relation with a moiety of the structure

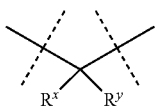

means that $R^x$ and $R^y$ form the following structure:

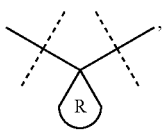

wherein R is $C_{3-10}$ cycloalkyl or 3- to 10-membered heterocyclyl.

It is also understood that the phrase "the pair $R^x/R^y$ is joint together with the atoms to which they are attached to form a ring A" in relation with a moiety of the structure

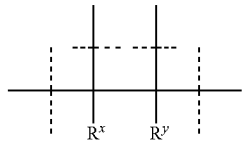

means that $R^x$ and $R^y$ form the following structure:

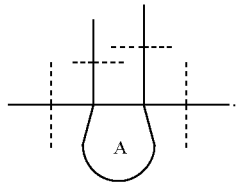

As used herein, "halogen" means fluoro, chloro, bromo or iodo. It is generally preferred that halogen is fluoro or chloro.

In general, the term "comprise" or "comprising" also encompasses "consist of" or "consisting of".

It is understood that experimenting with humans is subject to strict rules. Therefore, a more easily accessible test system in the form of an animal model may be needed to determine the dosage of PTH 1-84 required to maintain serum calcium within normal levels in otherwise hypocalcaemic subjects, which in human preferably refers to a serum albumin-adjusted calcium level of above 8.5 mg/dL and below 10.5 mg/dL with an optimal level of 9.5 mg/dL which corresponds to a range of 2.125 to 2.625 nmol/L with an optimum of 2.375 nmol/L. One such animal model are thyroparathyroidectomized (TPTX) rats. Rats subjected to thyroparathyroidectomy are unable to produce parathyroid hormone, PTH, the major regulator of calcium homeostasis, and consequently will develop hypocalcemia.

However, it is also understood that serum calcium levels may vary between different species, such as between human and rats, so in order to achieve comparable results values have to be adjusted to accommodate these inter-species differences. Therefore, when using such animal models, it is necessary to first determine the species' normal serum calcium levels for a given sex and age. For example, Watchorn (Biochem J. 1933; 27(6): 1875-1878) provides the normal range of serum calcium (not adjusted) of male rats as 10.29 to 13.16 mg/dL and as 9.61 to 14.04 mg/dL for female rats. Preferably, the normal serum calcium range is determined as a serum calcium concentration above the lower range of normal, e.g. as above 9.6 mg/dL (not adjusted) for female rats, even more preferably for female rats aged 13 to 22 weeks. Preferably, the normal serum calcium range is determined as a serum calcium concentration below the upper range of normal, e.g. as below 14 mg/dL (not adjusted) for female rats, even more preferably for female rats aged 13 to 22 weeks.

Accordingly, when subjecting female rats to thyroparathyroidectomy to obtain TPTX rats, the normal range to target with treatment would be above 9.6 mg/dL (not adjusted) and preferably below 14 mg/dL (not adjusted) in such animals aged 13 to 22 weeks.

Preferably, the pharmaceutical composition of the present invention is for use in the treatment of a condition treatable by PTH.

The pharmaceutical composition for use of the present invention is administered no more frequent than once every 24 hours, such as every 24 hours, every 48 hours, every 72 hours, every 96 hours, every 120 hours, every 144 hours, once a week, once every two weeks. Preferably, administration of the pharmaceutical composition of the present invention occurs in multiples of 24 hours, i.e. every N times 24 hours, whereas N is an integer selected from the group consisting of 1, 2, 3, 4, 5, 6, 7, 8, 9, 10, 11, 12, 13 and 14.

In one embodiment the pharmaceutical composition for use of the present invention is administered once every 24 hours.

In another embodiment the pharmaceutical composition for use of the present invention is administered once every 48 hours.

In another embodiment the pharmaceutical composition for use of the present invention is administered once every 72 hours.

In another embodiment the pharmaceutical composition for use of the present invention is administered once every 96 hours.

In another embodiment the pharmaceutical composition for use of the present invention is administered once every 120 hours.

In another embodiment the pharmaceutical composition for use of the present invention is administered once every 144 hours.

In another embodiment the pharmaceutical composition for use of the present invention is administered once every week.

In the present invention PTH 1-84 is administered every 24 hours. This means that if the pharmaceutical composition comprising the controlled-release PTH compound is administered every 24 hours, both the pharmaceutical composition comprising the controlled-release PTH compound and PTH 1-84 are administered with the same frequency. If the pharmaceutical composition comprising the controlled-release PTH compound is administered with intervals longer than 24 hours, PTH 1-84 is administered more than once within the interval between two consecutive administrations of the pharmaceutical composition comprising the controlled-release PTH compound. In such case the total amount of PTH1-84 is calculated from all administrations occurring in said interval between two consecutive administrations of the pharmaceutical composition comprising the controlled-release PTH compound of the present invention to obtain the basis for determining the molar equivalent dose of the controlled-release PTH compound.

The pharmaceutical composition for use of the present invention is administered by injection. In one embodiment administration is by intramuscular injection. In another embodiment administration is by intravenous injection. In another embodiment administration is by subcutaneous injection.

It is understood that the mode of administration of the controlled-release PTH compound and the mode of administration of the PTH 1-84 are identical, i.e. if the PTH 1-84 is administered by subcutaneous injection, also the controlled-release PTH compound is administered by subcutaneous injection. If the PTH 1-84 is administered by intramuscular injection, also the controlled-release PTH compound is administered by intramuscular injection.

In one embodiment the pharmaceutical composition for use of the present invention is performed with a syringe. In another embodiment the pharmaceutical composition for use of the present invention is administered with a pen injector. In another embodiment the pharmaceutical composition for use of the present invention is administered with an auto injector.

In the present invention the pharmaceutical composition for use of the present invention is administered no more frequent than every 24 hours with a dosage of the controlled-release PTH compound that corresponds to no more than 70% of the molar equivalent dose of PTH 1-84 required to maintain serum calcium within a normal range, preferably above 8.5 mg/dL, in humans over a 24 hour period. Preferably, the pharmaceutical composition for use of the present invention is administered with a dosage of the controlled-release PTH compound that corresponds to no more than 65%, more preferably with a dosage of the controlled-release PTH compound that corresponds to no more than 60%, even more preferably with a dosage of the controlled-release PTH compound that corresponds to no more than 55%, even more preferably with a dosage of the controlled-release PTH compound that corresponds to no more than 50%, even more preferably with a dosage of the controlled-release PTH compound that corresponds to no more than 45%, even more preferably with a dosage of the controlled-release PTH compound that corresponds to no more than 40%, even more preferably with a dosage of the controlled-release PTH compound that corresponds to no more than 35% and most preferably with a dosage of the controlled-release PTH compound that corresponds to no more than 30% of the molar equivalent dose of PTH 1-84 required to maintain serum calcium within the normal range, preferably above 8.5 mg/dL, in humans over a 24 hour period.

Preferably, the PTH compound comprises a PTH molecule or PTH moiety having the sequence of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:107, SEQ ID NO:108, SEQ ID NO:109, SEQ ID NO:110, SEQ ID NO:111, SEQ ID NO:112, SEQ ID NO:113, SEQ ID NO:114 or SEQ ID NO:115. More preferably the PTH molecule or PTH moiety has the sequence of SEQ ID NO:50, SEQ ID NO:51, SEQ ID NO:52, SEQ ID NO:110, SEQ ID NO:111 or SEQ ID NO:112.

In one embodiment the PTH molecule or PTH moiety has the sequence of SEQ ID NO:50.

In another embodiment the PTH molecule or PTH moiety has the sequence of SEQ ID NO:52.

In another embodiment the PTH molecule or PTH moiety has the sequence of SEQ ID NO:110.

In another embodiment the PTH molecule or PTH moiety has the sequence of SEQ ID NO:111.

In another embodiment the PTH molecule or PTH moiety has the sequence of SEQ ID NO:112.

Most preferably the PTH molecule or PTH moiety has the sequence of SEQ ID NO:51.

In one embodiment the controlled-release PTH compound is water-insoluble.

Preferably, a water-insoluble controlled-release PTH compound is selected from the group consisting of crystals, nanoparticles, microparticles, nanospheres and microspheres.

In one embodiment the water-insoluble controlled-release PTH compound is a crystal comprising at least one PTH molecule or PTH moiety.

In another embodiment the water-insoluble controlled-release PTH compound is a nanoparticle comprising at least one PTH molecule or PTH moiety.

In another embodiment the water-insoluble controlled-release PTH compound is a microparticle comprising at least one PTH molecule or PTH moiety.

In another embodiment the water-insoluble controlled-release PTH compound is a nanosphere comprising at least one PTH molecule or PTH moiety.

In another embodiment the water-insoluble controlled-release PTH compound is a microsphere comprising at least one PTH molecule or PTH moiety.

In one embodiment the water-insoluble controlled-release PTH compound is a vesicle comprising at least one PTH molecule or PTH moiety. Preferably, such vesicle comprising at least one PTH molecule or PTH moiety is a micelle, liposome or polymersome.

In one embodiment the water-insoluble controlled-release PTH compound is a micelle comprising at least one PTH molecule or PTH moiety.

In another embodiment the water-insoluble controlled-release PTH compound is a liposome comprising at least one PTH molecule or PTH moiety. Preferably, such liposome is selected from the group consisting of aquasomes; non-ionic surfactant vesicles, such as niosomes and proniosomes; cationic liposomes, such as LeciPlex; transfersomes; ethosomes; ufasomes; sphingosomes; and pharmacosomes.

In another embodiment the water-insoluble controlled-release PTH compound is a polymersome comprising at least one PTH molecule or PTH moiety.

In another embodiment the water-insoluble controlled-release PTH compound comprises at least one PTH molecule non-covalently embedded in a water-insoluble polymer. Preferably, such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In a preferred embodiment the water-insoluble controlled-release PTH compound comprises at least one PTH molecule non-covalently embedded in poly(lactic-co-glycolic acid) (PLGA).

In another embodiment the water-insoluble controlled-release PTH compound comprises at least one PTH moiety covalently and reversibly conjugated to a water-insoluble polymer. Preferably such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In one embodiment such water-insoluble controlled-release PTH compound is a compound comprising a conjugate D-L, wherein -D is a PTH moiety; and -L comprises a reversible prodrug linker moiety -L$^1$-, which moiety -L$^1$- is connected to the PTH moiety -D through a functional group of PTH; wherein -L$^1$- is substituted with -L$^2$—Z' and is optionally further substituted; wherein -L$^2$- is a single chemical bond or a spacer moiety; and —Z' is a water-insoluble carrier moiety.

It is understood that a multitude of moieties -L$^2$-L$^1$-D is connected to a water-insoluble carrier —Z' and that such controlled-release PTH compounds are PTH prodrugs, more specifically carrier-linked PTH prodrugs.

Preferred embodiments for -D, -L$^1$-, -L$^2$- and —Z' are as described below.

In a preferred embodiment the controlled-release PTH compound is water-soluble.

In a preferred embodiment such water-soluble controlled-release PTH compound is a compound of formula (Ia) or (Ib) or a pharmaceutically acceptable salt thereof

 (Ia)

 (Ib), wherein

-D is a PTH moiety;

-L$^1$- is a reversible prodrug linker moiety reversibly and covalently connected to the PTH moiety -D through a functional group of PTH;

-L$^2$- is a single chemical bond or a spacer moiety;

—Z is a water-soluble carrier moiety;

x is an integer selected from the group consisting of 1, 2, 3, 4, 5, 6, 7, 8, 9, 10, 11, 12, 13, 14, 15 or 16; and y is an integer selected from the group consisting of 1, 2, 3, 4 and 5.

It is understood that the compounds of formula (Ia) and (Ib) are PTH prodrugs, more specifically water-soluble PTH prodrugs.

Preferably, -D has the sequence of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:107, SEQ ID NO:108, SEQ ID NO:109, SEQ ID NO:110, SEQ ID NO:111, SEQ ID NO:112, SEQ ID NO:113, SEQ ID NO:114 or SEQ ID NO:115. More preferably -D has the sequence of SEQ ID NO:50, SEQ ID NO:51, SEQ ID NO:52, SEQ ID NO:110, SEQ ID NO:111 or SEQ ID NO:112.

In one embodiment -D has the sequence of SEQ ID NO:50.

In another embodiment -D has the sequence of SEQ ID NO:52.

In another embodiment -D has the sequence of SEQ ID NO:110.

In another embodiment -D has the sequence of SEQ ID NO:111.

In another embodiment -D has the sequence of SEQ ID NO:112.

Most preferably -D has the sequence of SEQ ID NO:51.

The moiety -$L^1$- is either conjugated to a functional group of the side chain of an amino acid residue of -D, to the N-terminal amine functional group or to the C-terminal carboxyl functional group of -D or to a nitrogen atom in the backbone polypeptide chain of -D. Attachment to either the N-terminus or C-terminus can either be directly through the corresponding amine or carboxyl functional group, respectively, or indirectly wherein a spacer moiety is first conjugated to the amine or carboxyl functional group to which spacer moiety -$L^1$- is conjugated.

Preferably, the amino acid residue of PTH to which -$L^1$- is conjugated comprises a functional group selected from the group consisting carboxylic acid, primary and secondary amine, maleimide, thiol, sulfonic acid, carbonate, carbamate, hydroxyl, aldehyde, ketone, hydrazine, isocyanate, isothiocyanate, phosphoric acid, phosphonic acid, haloacetyl, alkyl halide, acryloyl, aryl fluoride, hydroxylamine, sulfate, disulfide, vinyl sulfone, vinyl ketone, diazoalkane, oxirane, guanidine and aziridine. Even more preferably the amino acid residue of PTH to which -$L^1$- is conjugated comprises a functional group selected from the group consisting hydroxyl, primary and secondary amine and guanidine. Even more preferably the amino acid residue of PTH to which -$L^1$- is conjugated comprises a primary or secondary amine functional group. Most preferably the amino acid residue of PTH to which -$L^1$- is conjugated comprises a primary amine functional group.

If the moiety -$L^1$- is conjugated to a functional group of the side chain of an amino acid residue of PTH said amino acid residue is selected from the group consisting of proteinogenic amino acid residues and non-proteinogenic amino acid residues.

In one embodiment -$L^1$- is conjugated to a functional group of the side chain of a non-proteinogenic amino acid residue of PTH. It is understood that such non-proteinogenic amino acid is not found in the sequence of native PTH or fragments thereof and that it may only be present in variants and derivatives of PTH.

In another embodiment -$L^1$- is conjugated to a functional group of the side chain of a proteinogenic amino acid residue of PTH. Preferably said amino acid is selected from the group consisting of histidine, lysine, tryptophan, serine, threonine, tyrosine, aspartic acid, glutamic acid and arginine. Even more preferably said amino acid is selected from the group consisting of lysine, aspartic acid, arginine and serine. Even more preferably said amino acid is selected from the group consisting of lysine, arginine and serine.

In one embodiment -$L^1$- is conjugated to a functional group of the side chain of a histidine of PTH.

In another embodiment -$L^1$- is conjugated to a functional group of the side chain of a lysine of PTH.

In another embodiment -$L^1$- is conjugated to a functional group of the side chain of a tryptophan of PTH.

In another embodiment -$L^1$- is conjugated to a functional group of the side chain of a serine of PTH.

In another embodiment -$L^1$- is conjugated to a functional group of the side chain of a threonine of PTH.

In another embodiment -$L^1$- is conjugated to a functional group of the side chain of a tyrosine of PTH.

In another embodiment -$L^1$- is conjugated to a functional group of the side chain of an aspartic acid of PTH.

In another embodiment -$L^1$- is conjugated to a functional group of the side chain of a glutamic acid of PTH.

In another embodiment -$L^1$- is conjugated to a functional group of the side chain of an arginine of PTH.

It is understood that not every PTH moiety may comprise all of these amino acid residues.

In a preferred embodiment -$L^1$- is conjugated to the N-terminal amine functional group of PTH, either directly through the corresponding amine functional group or indirectly wherein a spacer moiety is first conjugated to the amine functional group to which spacer moiety -$L^1$- is conjugated. Even more preferably, -$L^1$- is directly conjugated to the N-terminal amine functional group of PTH.

In an equally preferred embodiment -$L^1$- is conjugated to the C-terminal functional group of PTH, either directly through the corresponding carboxyl functional group or indirectly wherein a spacer moiety is first conjugated to the carboxyl functional group to which spacer moiety -$L^1$- is conjugated.

Most preferably $L^1$- is directly conjugated to the N-terminal amine functional group of PTH.

The moiety -$L^1$- can be connected to -D through any type of linkage, provided that it is reversible. Preferably, -$L^1$- is connected to -D through a linkage selected from the group consisting of amide, ester, carbamate, acetal, aminal, imine, oxime, hydrazone, disulfide and acylguanidine. Even more preferably -$L^1$- is connected to -D through a linkage selected from the group consisting of amide, ester, carbamate and acylguanidin. It is understood that some of these linkages are not reversible per se, but that in the present invention neighboring groups comprised in -$L^1$- render these linkage reversible.

In one embodiment -$L^1$- is connected to -D through an ester linkage.

In another embodiment -$L^1$- is connected to -D through a carbamate linkage.

In another embodiment -$L^1$- is connected to -D through an acylguanidine.

In a preferred embodiment -$L^1$- is connected to -D through an amide linkage.

The moiety -$L^1$- is a reversible prodrug linker from which the drug, i.e. PTH, is released in its free form, i.e. it is a traceless prodrug linker. Suitable prodrug linkers are known in the art, such as for example the reversible prodrug linker moieties disclosed in WO 2005/099768 A2, WO 2006/136586 A2, WO 2011/089216 A1 and WO 2013/024053 A1, which are incorporated by reference herewith.

In another embodiment -$L^1$- is a reversible prodrug linker as described in WO 2011/012722 A1, WO 2011/089214 A1, WO 2011/089215 A1, WO 2013/024052 A1 and WO 2013/160340 A1 which are incorporated by reference herewith.

A particularly preferred moiety -L$^1$- is disclosed in WO 2009/095479 A2. Accordingly, in a preferred embodiment the moiety -L$^1$- is of formula (II):

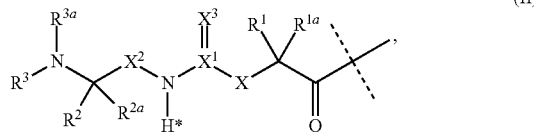

wherein the dashed line indicates the attachment to a nitrogen, hydroxyl or thiol of -D which is a PTH moiety;

—X— is selected from the group consisting of —C(R$^4$R$^{4a}$)—; —N(R$^4$)—; —O—; —C(R$^4$R$^{4a}$)—C(R$^5$R$^{5a}$)—; —C(R$^5$R$^{5a}$)—C(R$^4$R$^{4a}$)—; —C(R$^4$R$^{4a}$)—N(R$^6$)—; —N(R$^6$)—C(R$^4$R$^{4a}$)—; —C(R$^4$R$^{4a}$)—O—; —O—C(R$^4$R$^{4a}$)—; and —C(R$^7$R$^{7a}$)—;

X$^1$ is selected from the group consisting of C; and S(O);

—X$^2$— is selected from the group consisting of —C(R$^8$R$^{8a}$)—; and —C(R$^8$R$^{8a}$)—C(R$^9$R$^{9a}$)—;

=X$^3$ is selected from the group consisting of =O; =S; and =N—CN;

—R$^1$, —R$^{1a}$, —R$^2$, —R$^{2a}$, —R$^4$, —R$^{4a}$, —R$^5$, —R$^{5a}$, —R$^6$, —R$^8$, —R$^{8a}$, —R$^9$ and —R$^{9a}$ are independently selected from the group consisting of —H; and C$_{1-6}$ alkyl;

—R$^3$ and —R$^{3a}$ are independently selected from the group consisting of —H; and C$_{1-6}$ alkyl, provided that in case one of —R$^3$ and —R$^{3a}$ or both are other than —H they are connected to N to which they are attached through an sp$^a$-hybridized carbon atom;

—R$^7$ is selected from the group consisting of —N(R$^{10}$R$^{10a}$); and —NR$^{10}$—(C=O)—R$^{11}$;

—R$^{7a}$, —R$^{10}$, —R$^{10a}$ and —R$^{11}$ are independently of each other selected from the group consisting of —H; and C$_{1-6}$ alkyl;

optionally, one or more of the pairs —R$^{1a}$/—R$^{4a}$, —R$^{1a}$/—R$^{5a}$, —R$^{1a}$/—R$^{7a}$, —R$^{4a}$/—R$^{5a}$ and —R$^{8a}$/—R$^{9a}$ form a chemical bond;

optionally, one or more of the pairs —R$^1$/R$^{1a}$, —R$^2$/—R$^{2a}$, —R$^4$/—R$^{4a}$, —R$^5$/—R$^{5a}$; —R$^8$/—R$^{8a}$ and —R$^9$/—R$^{9a}$ are joined together with the atom to which they are attached to form a C$_{3-10}$ cycloalkyl; or 3- to 10-membered heterocyclyl;

optionally, one or more of the pairs —R$^1$/—R$^4$, —R$^1$/—R$^5$, —R$^1$/—R$^6$, —R$^1$/—R$^{7a}$, —R$^4$/—R$^5$, —R$^4$/—R$^6$, —R$^8$/—R$^9$ and —R$^2$/—R$^3$ are joined together with the atoms to which they are attached to form a ring A;

optionally, R$^3$/R$^{3a}$ are joined together with the nitrogen atom to which they are attached to form a 3- to 10-membered heterocycle;

A is selected from the group consisting of phenyl; naphthyl; indenyl; indanyl;

tetralinyl; C$_{3-10}$ cycloalkyl; 3- to 10-membered heterocyclyl; and 8- to 11-membered heterobicyclyl; and wherein -L$^1$- is substituted with -L$^2$-Z or -L$^2$-Z' and wherein -L$^1$- is optionally further substituted, provided that the hydrogen marked with the asterisk in formula (II) is not replaced by -L$^2$-Z or -L$^2$-Z' or a substituent;

wherein

-L$^2$- is a single chemical bond or a spacer;

—Z is a water-soluble carrier; and

—Z' is a water-insoluble carrier.

Preferably -L$^1$- of formula (II) is substituted with one moiety -L$^2$-Z or -L2-Z'.

In one embodiment -L$^1$- of formula (II) is not further substituted.

It is understood that if —R$^3$/—R$^{3a}$ of formula (II) are joined together with the nitrogen atom to which they are attached to form a 3- to 10-membered heterocycle, only such 3- to 10-membered heterocycles may be formed in which the atoms directly attached to the nitrogen are sp$^a$-hybridized carbon atoms. In other words, such 3- to 10-membered heterocycle formed by —R$^3$/—R$^{3a}$ together with the nitrogen atom to which they are attached has the following structure:

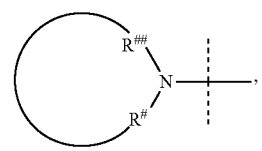

wherein the dashed line indicates attachment to the rest of -L$^1$-;

the ring comprises 3 to 10 atoms comprising at least one nitrogen; and

R$^{\#}$ and R$^{190\ \#}$ represent an sp$^3$-hybridized carbon atom.

It is also understood that the 3- to 10-membered heterocycle may be further substituted.

Exemplary embodiments of suitable 3- to 10-membered heterocycles formed by —R$^3$/—R$^{3a}$ of formula (II) together with the nitrogen atom to which they are attached are the following:

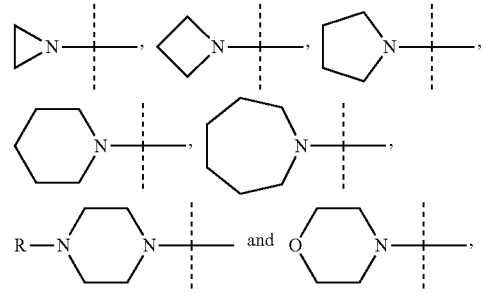

wherein dashed lines indicate attachment to the rest of the molecule; and

—R is selected from the group consisting of —H and C$_{1-6}$ alkyl.

-L$^1$- of formula (II) may optionally be further substituted. In general, any substituent may be used as far as the cleavage principle is not affected, i.e. the hydrogen marked with the asterisk in formula (II) is not replaced and the nitrogen of the moiety

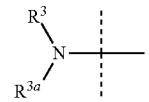

of formula (II) remains part of a primary, secondary or tertiary amine, i.e. —R$^3$ and —R$^{3a}$ are independently of each other —H or are connected to —N< through an sp$^3$-hybridized carbon atom.

In one embodiment —R' or —R$^{1a}$ of formula (II) is substituted with -L$^2$—Z or -L$^2$- Z'. In another embodiment —R$^2$ or —R$^{2a}$ of formula (II) is substituted with -L$^2$-Z or -L$^2$-Z'. In another embodiment —R$^3$ or —R$^{3a}$ of formula (II) is substituted with -L$^2$-Z or -L$^2$-Z'. In another embodiment —R$^4$ of formula (II) is substituted with -L$^2$-Z or -L$^2$-Z'. In another embodiment —R$^5$ or —R$^{5a}$ of formula (II) is substituted with -L$^2$-Z or -L$^2$-Z'. In another embodiment —R$^6$ of formula (II) is substituted with -L$^2$-Z or -L$^2$-Z'. In another embodiment —R$^7$ or —R$^{7a}$ of formula (II) is substituted with -L$^2$-Z or -L$^2$-Z'. In another embodiment —R$^8$ or —R$^{8a}$ of formula (II) is substituted with -L$^2$-Z or -L$^2$-Z'. In another embodiment —R$^9$ or —R$^{9a}$ of formula (II) is substituted with -L$^2$-Z or -L$^2$-Z'. In another embodiment —R$^{10}$ is substituted with -L$^2$-Z or -L$^2$-Z'. In another embodiment —R$^{11}$ is substituted with -L$^2$-Z or -L$^2$-Z'.

Preferably, —X— of formula (II) is selected from the group consisting of —C(R$^4$R$^{4a}$)—, —N(R$^4$)— and —C(R$^7$R$^{7a}$)—.

In one embodiment —X— of formula (II) is —C(R$^4$R$^{4a}$)—.

In one preferred embodiment —X— of formula (II) is —C(R$^7$R$^{7a}$)—.

Preferably, —R$^7$ of formula (II) is —NR$^{10}$—(C=O)—R$^{11}$.

Preferably, —R$^{7a}$ of formula (II) is selected from —H, methyl and ethyl. Most preferably —R$^{7a}$ of formula (II) is —H.

Preferably, —R$^{10}$ is selected from —H, methyl and ethyl. Most preferably —R$^{10}$ is methyl.

Preferably, —R$^{11}$ is selected from —H, methyl and ethyl. Most preferably —R$^{11}$ is —H.

Preferably, —R$^{11}$ is substituted with -L$^2$-Z or -L$^2$-Z'.

In another preferred embodiment —X— of formula (II) is —N(R$^4$)—.

Preferably, —R$^4$ is selected from the group consisting of —H, methyl and ethyl. Preferably, —R$^4$ is —H.

Preferably, X$^1$ of formula (II) is C.

Preferably, =X$^3$ of formula (II) is =O.

Preferably, —X$^2$— of formula (II) is —C(R$^8$R$^{8a}$)—.

Preferably —R$^8$ and —R$^{8a}$ of formula (II) are independently selected from the group consisting of —H, methyl and ethyl. More preferably at least one of —R$^8$ and —R$^{8a}$ of formula (II) is —H. Even more preferably both —R$^8$ and —R$^{8a}$ of formula (II) are —H.

Preferably, —R$^1$ and —R$^1a$ of formula (II) are independently selected from the group consisting of —H, methyl and ethyl.

In one preferred embodiment at least one of —R' and —R$^{1a}$ of formula (II) is —H, more preferably both —R$^1$ and —R$^1a$ of formula (II) are —H.

In another preferred embodiment at least one of —R$^1$ and —R$^{1a}$ of formula (II) is methyl, more preferably both —R' and —R$^{1a}$ of formula (II) are methyl.

Preferably, —R$^2$ and —R$^{2a}$ of formula (II) are independently selected from the group consisting of —H, methyl and ethyl. More preferably, at least one of —R$^2$ and —R$^{2a}$ of formula (II) is —H. Even more preferably both —R$^2$ and —R$^{2a}$ of formula (II) are H.

Preferably, —R$^3$ and —R$^{3a}$ of formula (II) are independently selected from the group consisting of —H, methyl, ethyl, propyl and butyl.

In one preferred embodiment at least one of —R$^3$ and —R$^{3a}$ of formula (II) is methyl, more preferably —R$^3$ of formula (II) is methyl and —R$^{3a}$ of formula (II) is —H.

In another preferred embodiment —R$^3$ and —R$^{3a}$ of formula (II) are both —H.

Preferably, -D is connected to -L$^1$- through a nitrogen by forming an amide bond.

In one preferred embodiment the moiety -L$^1$- is of formula (IIa-i):

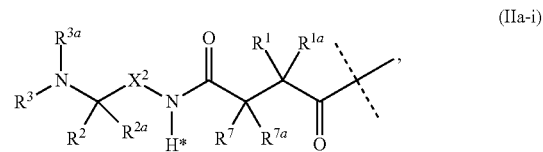

(IIa-i)

wherein
the dashed line indicates the attachment to a nitrogen of -D which is a PTH moiety by forming an amide bond;
—R$^1$, —R$^{1a}$, —R$^2$, —R$^{2a}$, —R$^3$, —R$^{3a}$, —R$^7$, —R$^{7a}$ and —X$^2$— are used as defined in formula (II); and
wherein -L$^1$- is substituted with -L$^2$-Z or -L$^2$-Z' and wherein -L$^1$- is optionally further substituted, provided that the hydrogen marked with the asterisk in formula (IIa-i) is not replaced by -L$^2$-Z or -L$^2$-Z' or a substituent.

It is understood that in case one of —R$^3$, —R$^{3a}$ of formula (IIa-i) or both are other than —H they are connected to N to which they are attached through an sp$^3$-hybridized carbon atom.

Preferably -L$^1$- of formula (IIa-i) is substituted with one moiety -L$^2$-Z or -L$^2$-Z'.

Preferably the moiety -L$^1$- of formula (IIa-i) is not further substituted.

Preferably, —R$^1$ and —R$^{1a}$ of formula (IIa-i) are independently selected from the group consisting of —H, methyl and ethyl. More preferably, at least one of —R$^1$ and —R$^{1a}$ of formula (IIa-i) is —H. Even more preferably both —R$^1$ and —R$^{1a}$ of formula (IIa-i) are —H.

Preferably, —R$^7$ of formula (IIa-i) is —NR$^{10}$—(C=O)—R$^{11}$.

Preferably, —R$^{7a}$ of formula (II-i) is selected from —H, methyl and ethyl. Most preferably —R$^{7a}$ of formula (II-i) is —H.

Preferably, —R$^{10}$ of formula (IIa-i) is selected from —H, methyl and ethyl. Most preferably —R$^{10}$ of formula (IIa-i) is methyl.

Preferably, —R$^{11}$ of formula (IIa-i) is selected from —H, methyl and ethyl. Most preferably —R$^{11}$ of formula (IIa-i) is —H.

Preferably, —R$^{11}$ of formula (IIa-i) is substituted with -L$^2$-Z or -L$^2$-Z'.

Preferably, —X$^2$— of formula (IIa-i) is —C(R$^8$R$^{8a}$)—.

Preferably —R$^8$ and —R$^{8a}$ of formula (IIa-i) are independently selected from the group consisting of —H, methyl and ethyl. More preferably at least one of —R$^8$ and —R$^{8a}$ of formula (IIa-i) is —H. Even more preferably both —R$^8$ and —R$^{8a}$ of formula (IIa-i) are —H.

Preferably, —R$^2$ and —R$^{2a}$ of formula (IIa-i) are independently selected from the group consisting of —H, methyl and ethyl. More preferably, at least one of —R$^2$ and —R$^{2a}$ of formula (IIa-i) is —H. Even more preferably both —R$^2$ and —R$^{2a}$" of formula (IIa-i) are H.

Preferably, —R$^3$ and —R$^{3a}$ of formula (IIa-i) are independently selected from the group consisting of —H, methyl, ethyl, propyl and butyl. Even more preferably at least one of —R$^3$ and —R$^{3a}$ of formula (IIa-i) is methyl.

Preferably, —R$^3$ of formula (IIa-i) is —H and —R$^{3a}$ of formula (IIa-i) is methyl.

More preferably the moiety -L¹- is of formula (IIa-ii):

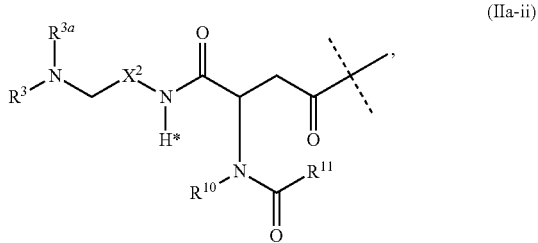

wherein the dashed line indicates the attachment to a nitrogen of -D which is a PTH moiety by forming an amide bond;
—R², —R²ᵃ, —R¹⁰, —R¹¹ and —X²— are used as defined in formula (II); and wherein -L¹- is substituted with -L²-Z or -L²-Z' and wherein -L¹- is optionally further substituted, provided that the hydrogen marked with the asterisk in formula (IIa-ii) is not replaced by -L²-Z or -L²-Z' or a substituent.

It is understood that in case one of —R³, —R³ᵃ of formula (IIa-ii) or both are other than —H they are connected to N to which they are attached through an sp³-hybridized carbon atom.

Preferably -L¹- of formula (IIa-ii) is substituted with one moiety -L²-Z or -L²-Z'.

Preferably the moiety -L¹- of formula (IIa-ii) is not further substituted.

Preferably, —X²— of formula (IIa-ii) is —C(R⁸R⁸ᵃ)—.

Preferably —R⁸ and —R⁸ᵃ of formula (IIa-ii) are independently selected from the group consisting of —H, methyl and ethyl. More preferably at least one of —R⁸ and —R⁸ᵃ of formula (IIa-ii) is —H. Even more preferably both —R⁸ and —R⁸ᵃ of formula (IIa-ii) are —H.

Preferably, —R³ and —R³ᵃ of formula (IIa-ii) are independently selected from the group consisting of —H, methyl, ethyl, propyl and butyl. Even more preferably at least one of —R³ and —R³ᵃ of formula (IIa-ii) is methyl.

Preferably, —R³ of formula (IIa-ii) is —H and —R³ᵃ of formula (IIa-ii) is methyl.

Preferably, —R¹⁰ of formula (IIa-ii) is selected from —H, methyl and ethyl. Most preferably —R¹⁰ of formula (IIa-ii) is methyl.

Preferably, —R¹¹ of formula (IIa-ii) is selected from —H, methyl and ethyl. Most preferably —R¹¹ of formula (IIa-ii) is —H.

Preferably, —R¹¹ of formula (IIa-ii) is substituted with -L²-Z or -L²-Z'.

In an even more preferred embodiment the moiety -L¹- is of formula (IIa-ii'):

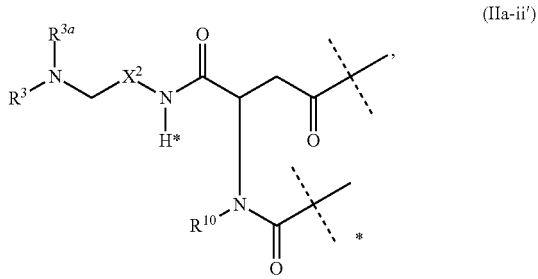

wherein
wherein the dashed line indicates the attachment to a nitrogen of D which is a PTH moiety by forming an amide bond;
the dashed line marked with the asterisk indicates attachment to -L²-;
—R³, —R³ᵃ, —R¹⁰ and —X²— are used as defined in formula (II); and
wherein -L¹- is optionally further substituted, provided that the hydrogen marked with the asterisk in formula (IIa-ii') is not replaced by a substituent.

It is understood that in case one of —R³, —R³ᵃ of formula (IIa-ii') or both are other than —H they are connected to N to which they are attached through a sp³-hybridized carbon atom.

Preferably the moiety -L¹- of formula (IIa-ii') is not further substituted.

Preferably, —X²— of formula (IIa-ii') is —C(R⁸R⁸ᵃ)—.

Preferably —R⁸ and —R⁸ᵃ of formula (IIa-ii') are independently selected from the group consisting of —H, methyl and ethyl. More preferably at least one of —R⁸ and —R⁸ᵃ of formula (IIa-ii') is —H. Even more preferably both —R⁸ and —R⁸ᵃ of formula (IIa-ii') are —H.

Preferably, —R³ and —R³ᵃ of formula (IIa-ii') are independently selected from the group consisting of —H, methyl, ethyl, propyl and butyl. Even more preferably at least one of —R³ and —R³ᵃ of formula (IIa-ii') is methyl.

Preferably, —R³ of formula (IIa-ii') is —H and —R³ᵃ of formula (IIa-ii') is methyl.

Preferably, —R¹⁰ of formula (IIa-ii') is selected from —H, methyl and ethyl. Most preferably —R¹⁰ of formula (IIa-ii') is methyl.

Even more preferably the moiety -L¹- is of formula (IIa-iii):

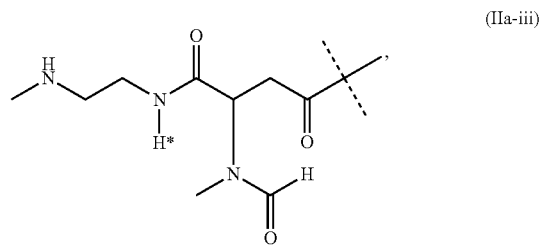

wherein the dashed line indicates the attachment to a nitrogen of -D which is a PTH moiety by forming an amide bond; and
wherein -L¹- is substituted with -L²-Z or -L²-Z' and wherein -L¹- is optionally further substituted, provided that the hydrogen marked with the asterisk in formula (IIa-iii) is not replaced by -L²-Z or -L²-Z' or a substituent.

It is understood that in case one of —R³, —R³ᵃ of formula (IIa-iii) or both are other than —H they are connected to N to which they are attached through an sp³-hybridized carbon atom.

Preferably -L¹- of formula (IIa-iii) is substituted with one moiety -L²-Z or -L²-Z'.

Preferably the moiety -L¹- of formula (IIa-iii) is not further substituted.

Most preferably the moiety -L$^1$- is of formula (IIa-iii'):

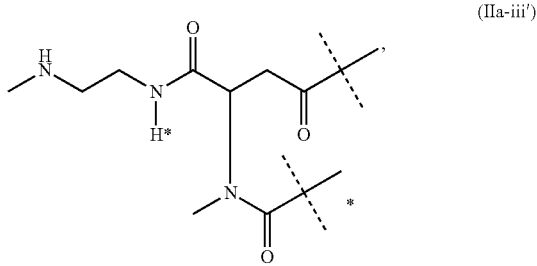

wherein
wherein the dashed line indicates the attachment to a nitrogen of D which is a PTH moiety by forming an amide bond;
the dashed line marked with the asterisk indicates attachment to -L$^2$-;
—R$^2$, —R$^{2a}$, —R$^3$, —R$^{3a}$ and —X$^2$— are used as defined in formula (II); and wherein -L$^1$- is optionally further substituted, provided that the hydrogen marked with the asterisk in formula (IIa-iii') is not replaced by a substituent.

It is understood that in case one of —R$^3$, —R$^{3a}$ of formula (IIa-iii') or both are other than —H they are connected to N to which they are attached through an sp$^3$-hybridized carbon atom.

Preferably the moiety -L$^1$- of formula (IIa-iii') is not further substituted.

In another preferred embodiment the moiety -L$^1$- is of formula (IIb-i)

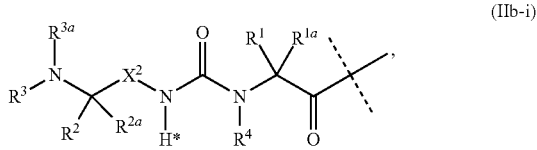

wherein
the dashed line indicates the attachment to a nitrogen of -D which is a PTH moiety by forming an amide bond; —R$^1$, —R$^{1a}$, —R$^2$, —R$^{2a}$, —R$^3$, —R$^{3a}$, —R$^4$ and —X$^2$— are used as defined in formula (II); and wherein -L$^1$- is substituted with -L$^2$-Z or -L$^2$-Z' and wherein -L$^1$- is optionally further substituted, provided that the hydrogen marked with the asterisk in formula (IIb-i) is not replaced by -L$^2$-Z or -L$^2$-Z' or a substituent.

It is understood that in case one of —R$^3$, —R$^{3a}$ of formula (IIb-i) or both are other than —H they are connected to N to which they are attached through an sp$^3$-hybridized carbon atom.

Preferably -L$^1$- of formula (IIb-i) is substituted with one moiety -L$^2$-Z or -L$^2$-Z'.

Preferably the moiety -L$^1$- of formula (IIb-i) is not further substituted.

Preferably, —R$^1$ and —R$^{1a}$ of formula (IIb-i) are independently selected from the group consisting of —H, methyl and ethyl. More preferably, at least one of —R$^1$ and —R$^{1a}$ of formula (IIb-i) is methyl. Even more preferably both —R$^1$ and —R$^{1a}$ of formula (IIb-i) are methyl.

Preferably, —R$^4$ of formula (IIb-i) is selected from the group consisting of —H, methyl and ethyl. More preferably, —R$^4$ of formula (IIb-i) is —H.

Preferably, —X$^2$— of formula (IIb-i) is —C(R$^8$R$^{8a}$)—.

Preferably —R$^8$ and —R$^{8a}$ of formula (IIb-i) are independently selected from the group consisting of —H, methyl and ethyl. More preferably at least one of —R$^8$ and —R$^{8a}$ of formula (IIb-i) is —H. Even more preferably both —R$^8$ and —R$^{8a}$ of formula (IIb-i) are —H.

Preferably, —R$^2$ and —R$^{2a}$ of formula (IIb-i) are independently selected from the group consisting of —H, methyl and ethyl. More preferably, at least one of —R$^2$ and —R$^{2a}$ of formula (IIb-i) is —H. Even more preferably both —R$^2$ and —R$^{2a}$ of formula (IIb-i) are H.

Preferably, —R$^3$ and —R$^{3a}$ of formula (IIb-i) are independently selected from the group consisting of —H, methyl, ethyl, propyl and butyl. Even more preferably at least one of —R$^3$ and —R$^{3a}$ of formula (IIb-i) is —H. Even more preferably both —R$^3$ and —R$^{3a}$ of formula (IIb-i) are —H.

More preferably the moiety -L$^1$- is of formula (IIb-ii):

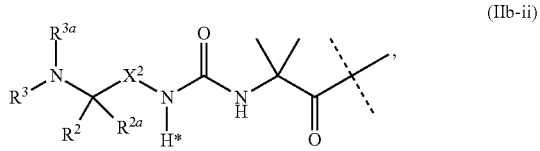

wherein the dashed line indicates the attachment to a nitrogen of -D which is a PTH moiety by forming an amide bond;
—R$^2$, —R$^{2a}$, —R$^3$, —R$^{3a}$ and —X$^2$— are used as defined in formula (II); and wherein -L$^1$- is substituted with -L$^2$-Z or -L$^2$-Z' and wherein -L$^1$- is optionally further substituted, provided that the hydrogen marked with the asterisk in formula (IIb-ii) is not replaced by -L$^2$-Z or -L$^2$-Z' or a substituent.

It is understood that in case one of —R$^3$, —R$^{3a}$ of formula (IIb-ii) or both are other than —H they are connected to N to which they are attached through an sp$^a$-hybridized carbon atom.

Preferably -L$^1$- of formula (IIb-ii) is substituted with one moiety -L$^2$-Z or -L$^2$-Z'.

Preferably the moiety -L$^1$- of formula (IIb-ii) is not further substituted.

Preferably, —X$^2$— of formula (IIb-ii) is —C(R$^8$R$^{8a}$)—.

Preferably —R$^8$ and —R$^{8a}$ of formula (IIb-ii) are independently selected from the group consisting of —H, methyl and ethyl. More preferably at least one of —R$^8$ and —R$^{8a}$ of formula (IIb-ii) is —H. Even more preferably both —R$^8$ and —R$^{8a}$ of formula (IIb-ii) are —H.

Preferably, —R$^2$ and —R$^{2a}$ of formula (IIb-ii) are independently selected from the group consisting of —H, methyl and ethyl. More preferably, at least one of —R$^2$ and —R$^{2a}$ of formula (IIb-ii) is —H. Even more preferably both —R$^2$ and —R$^{2a}$ of formula (IIb-ii) are H.

Preferably, —R$^3$ and —R$^{3a}$ of formula (IIb-ii) are independently selected from the group consisting of —H, methyl, ethyl, propyl and butyl. Even more preferably at least one of —R$^3$ and —R$^{3a}$ of formula (IIb-ii) is —H. Even more preferably both —R$^3$ and —R$^{3a}$ of formula (IIb-ii) are —H.

Even more preferably the moiety -L¹- is of formula (IIb-ii'):

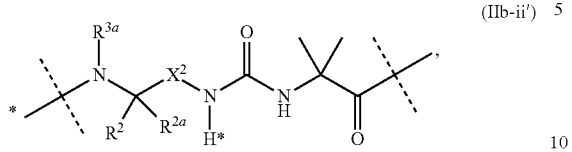

wherein
the dashed line indicates the attachment to a nitrogen of -D which is a PTH moiety by forming an amide bond; —R², —R²ᵃ, —R³ᵃ and —X²— are used as defined in formula (II); and wherein -L¹- is substituted with -L²-Z or -L²-Z' and wherein -L¹- is optionally further substituted, provided that the hydrogen marked with the asterisk in formula (IIb-ii') is not replaced by -L²-Z or -L²-Z' or a substituent.

It is understood that in case —R³ᵃ of formula (IIb-ii') is other than —H it are connected to N to which it is attached through an sp^a-hybridized carbon atom.

Preferably the moiety -L¹- of formula (IIb-ii') is not further substituted.

Preferably, —X²— of formula (IIb-ii') is —C(R⁸R⁸ᵃ)—.

Preferably —R⁸ and —R⁸ᵃ of formula (IIb-ii') are independently selected from the group consisting of —H, methyl and ethyl. More preferably at least one of —R⁸ and —R⁸ᵃ of formula (IIb-ii') is —H. Even more preferably both —R⁸ and —R⁸ᵃ of formula (IIb-ii') are —H.

Preferably, —R² and —R²ᵃ of formula (IIb-ii') are independently selected from the group consisting of —H, methyl and ethyl. More preferably, at least one of —R² and —R²ᵃ of formula (IIb-ii') is —H. Even more preferably both —R² and —R²ᵃ of formula (IIb-ii') are H.

Preferably, —R³ᵃ of formula (IIb-ii') is selected from the group consisting of —H, methyl, ethyl, propyl and butyl. In one embodiment —R³ᵃ of formula (IIb-ii') is —H.

Even more preferably the moiety -L¹- is of formula (IIb-iii):

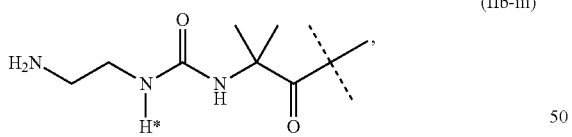

wherein
the dashed line indicates the attachment to a nitrogen of -D which is a PTH moiety by forming an amide bond; and
wherein -L¹- is substituted with -L²-Z or -L²-Z' and wherein -L¹- is optionally further substituted, provided that the hydrogen marked with the asterisk in formula (IIb-iii) is not replaced by -L²-Z or -L²-Z' or a substituent.

It is understood that in case one of —R³, —R³ᵃ of formula (IIb-iii) or both are other than —H they are connected to N to which they are attached through an sp^a-hybridized carbon atom.

Preferably -L¹- of formula (IIb-iii) is substituted with one moiety -L²-Z or -L²-Z'.

Preferably the moiety -L¹- of formula (IIb-iii) is not further substituted.

Most preferably the moiety -L¹- is of formula (IIb-iii'):

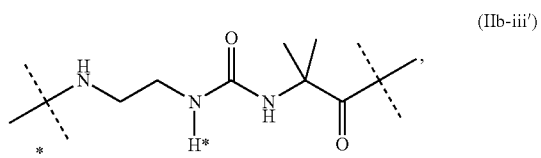

wherein
the dashed line indicates the attachment to a nitrogen of -D which is a PTH moiety by forming an amide bond;
the dashed line marked with the asterisk indicates attachment to -L²-; and
wherein -L¹- is optionally further substituted, provided that the hydrogen marked with the asterisk in formula (IIb-iii') is not replaced by -L²-Z or -L²-Z' or a substituent.

It is understood that the nitrogen adjacent to the dashed line marked with the asterisk in formula (IIb-iii') is attached to -L²- through an sp³-hybridized carbon atom.

Preferably the moiety -L¹- of formula (IIb-iii') is not further substituted.

Another preferred moiety -L¹- is disclosed in WO2016/020373A1. Accordingly, in another preferred embodiment the moiety -L¹- is of formula (III):

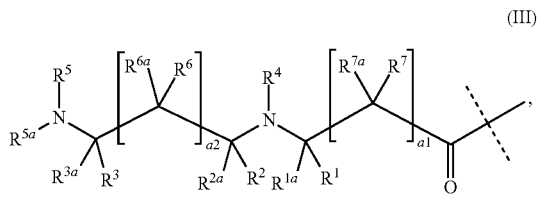

wherein
the dashed line indicates attachment to a primary or secondary amine or hydroxyl of -D which is a PTH moiety by forming an amide or ester linkage, respectively;
—R¹, —R¹ᵃ, —Ru², —R²ᵃ, —R³ and —R³ᵃ are independently of each other selected from the group consisting of —H, —C(R⁸R⁸ᵃR⁸ᵇ) —C(=O)R⁸, —C(=NR⁸) R⁸ᵃ, —CR8(=CR⁸ᵃR⁸ᵇ) C≡CR⁸ and -T;
—R⁴, —R⁵ and —R⁵ᵃ are independently of each other selected from the group consisting of —H, —C(R⁹R⁹ᵃR⁹ᵇ) and -T;
a1 and a2 are independently of each other 0 or 1;
each —R⁶, —R⁶ᵃ, —R⁷, —R⁷ᵃ, —R⁸, —R⁸ᵃ, —R⁹, —R⁹ᵇ are independently of each other selected from the group consisting of —H, halogen, —CN, —COOR¹⁰, —OR¹⁰, —C(O)R¹⁰, —C(O)R¹⁰, —C(O)N(R¹⁰R¹⁰ᵃ), —S(O)₂N(R¹⁰R¹⁰ᵃ), —S(O)N(R¹⁰R¹⁰ᵃ), —S(O)₂R¹⁰, —S(O)R¹⁰, —N(R¹⁰)S(O)₂N(R¹⁰ᵃR¹⁰ᵇ), —SR¹⁰, —N(R¹⁰R¹⁰ᵃ), NO₂, —OC(O)R¹⁰, —N(R¹⁰)C(O) R¹⁰ᵃ, —N(R¹⁰)S(O)₂R¹⁰ᵃ, —N(R¹⁰)S(O)R¹⁰ᵃ, —N(R¹⁰)C(O)OR¹⁰ᵃ, —N(R¹⁰)C(O)_N(R¹⁰ᵃR¹⁰ᵇ), —OC(O)N(R¹⁰R¹⁰ᵃ), -T, C₁₋₂₀ alkyl, C₂₋₂₀ alkenyl, and C₂₋₂₀ alkynyl; wherein -T, C₁₋₂₀ alkyl, C₂₋₂₀ alkenyl, and C₂₋₂₀ alkynyl are optionally substituted with one or more —R¹¹, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —S(O)$_2$N ($R^{12}$)—, —S(O)N($R^{12}$)—, —S(O)$_2$—, —S(O)—, —N($R^{12}$)S(O)$_2$N($R^{12a}$)—, —S—, —N($R^{12}$)—, —OC (O$R^{12}$)($R^{12a}$)—, —N($R^{12}$)C(O)N($R^{12a}$)—, and —OC (O)N($R^{12}$)—;

each —$R^{10}$, —$R^{10a}$, —$R^{10b}$ is independently selected from the group consisting of —H, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —S(O)$_2$N($R^{12}$)—, —S(O)N($R^{12}$)—, —S(O)$_2$—, —S(O)—, —N($R^{12}$)S(O)$_2$N($R^{12a}$)—, —S—, —N($R^{12}$)—, —OC(O$R^{12}$)($R^{12a}$)—, —N($R^{12}$)C(O)N ($R^{12a}$)—, and —OC(O)N($R^{12}$)—;

each T is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T is independently optionally substituted with one or more —$R^{11}$, which are the same or different;

each —$R^{11}$ is independently of each other selected from halogen, —CN, oxo (=O), —COO$R^{13}$, —O$R^{13}$, —C(O)$R^{13}$, —C(O)N($R^{13}R^{13a}$), —S(O)$_2$N($R^{13}R^{13a}$), —S(O)N($R^{13}R^{13a}$), —S(O)$_2R^{13}$, —S(O)$R^{13}$, —N($R^{13}$)S(O)$_2$N($R^{13a}R^{13b}$), —S$R^{13}$, —N($R^{13}R^{13a}$), —NO$_2$, —OC(O)$R^{13}$, —N($R^{13}$)C(O)$R^{13a}$, —N($R^{13}$)S(O)$_2R^{13a}$, —N($R^{13}$)S(O)$R^{13a}$, —N($R^{13}$)C(O)O$R^{13a}$, —N($R^{13}$)C(O)N($R^{13a}R^{13b}$), —OC(O)N($R^{13}R^{13a}$), and $C_{1-6}$ alkyl; wherein $C_{1-6}$ alkyl is optionally substituted with one or more halogen, which are the same or different;

each —$R^{12}$, —$R^{12a}$, —$R^{13}$, —$R^{13a}$, —$R^{13b}$ is independently selected from the group consisting of —H, and $C_{1-6}$ alkyl; wherein $C_{1-6}$ alkyl is optionally substituted with one or more halogen, which are the same or different;

optionally, one or more of the pairs —$R^1$/—$R^{1a}$, —$R^2$/—$R^{2a}$, —$R^3$/—$R^{3a}$, —$R^6$/—$R^{6a}$, —$R^7$/—$R^{7a}$ are joined together with the atom to which they are attached to form a $C_{3-10}$ cycloalkyl or a 3- to 10-membered heterocyclyl;

optionally, one or more of the pairs —$R^1$/—$R^2$, —$R^1$/—$R^3$, —$R^1$/—$R^4$, —$R^1$/—$R^5$, —$R^1$/—$R^6$, —$R^1$/—$R^7$, —$R^2$/—$R^3$, —$R^2$/—$R^4$, —$R^2$/—$R^5$, —$R^2$/—$R^6$, —$R^2$/—$R^7$, —$R^3$/—$R^4$, —$R^3$/—$R^5$, —$R^3$/—$R^6$, —$R^3$/—$R^7$, —$R^4$/—$R^5$, —$R^4$/—$R^6$, —$R^4$/—$R^7$, —$R^5$/—$R^6$, —$R^5$/—$R^7$, —$R^6$/—$R^7$ are joint together with the atoms to which they are attached to form a ring A;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl;

wherein -$L^1$- is substituted with -$L^2$-Z or -$L^2$-Z' and wherein -$L^1$- is optionally further substituted;
wherein
-$L^2$- is a single chemical bond or a spacer;
—Z is a water-soluble carrier; and
—Z' is a water-insoluble carrier.

The optional further substituents of -$L^1$- of formula (III) are preferably as described above.

Preferably -$L^1$- of formula (III) is substituted with one moiety -$L^2$-Z or -$L^2$-Z'.

In one embodiment -$L^1$- of formula (III) is not further substituted.

Additional preferred embodiments for -$L^1$- are disclosed in EP1536334B1, WO2009/009712A1, WO2008/034122A1, WO2009/143412A2, WO2011/082368A2, and U.S. Pat. No. 8,618,124B2, which are herewith incorporated by reference in their entirety.

Additional preferred embodiments for -$L^1$- are disclosed in U.S. Pat. Nos. 8,946,405B2 and 8,754,190B2, which are herewith incorporated by reference in their entirety. Accordingly, a preferred moiety -$L^1$- is of formula (IV):

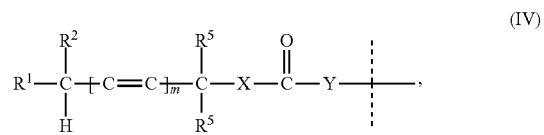

(IV)

wherein
the dashed line indicates attachment to -D which is a PTH moiety and wherein attachment is through a functional group of -D selected from the group consisting of —OH, —SH and —NH$_2$;
m is 0 or 1;
at least one or both of —$R^1$ and —$R^2$ is/are independently of each other selected from the group consisting of —CN, —NO$_2$, optionally substituted aryl, optionally substituted heteroaryl, optionally substituted alkenyl, optionally substituted alkynyl, —C(O)$R^3$, —S(O)$R^3$, —S(O)$_2R^3$, and —S$R^4$,
one and only one of —$R^1$ and —$R^2$ is selected from the group consisting of —H, optionally substituted alkyl, optionally substituted arylalkyl, and optionally substituted heteroarylalkyl;
—$R^3$ is selected from the group consisting of —H, optionally substituted alkyl, optionally substituted aryl, optionally substituted arylalkyl, optionally substituted heteroaryl, optionally substituted heteroarylalkyl, —O$R^9$ and —N($R^9$)$_2$;
—$R^4$ is selected from the group consisting of optionally substituted alkyl, optionally substituted aryl, optionally substituted arylalkyl, optionally substituted heteroaryl, and optionally substituted heteroarylalkyl;
each —$R^5$ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;
—$R^9$ is selected from the group consisting of —H and optionally substituted alkyl;
—Y— is absent and —X— is —O— or —S—; or
—Y— is —N(Q)CH$_2$— and —X— is —O—;
Q is selected from the group consisting of optionally substituted alkyl, optionally substituted aryl, optionally substituted arylalkyl, optionally substituted heteroaryl and optionally substituted heteroarylalkyl; optionally, —$R^1$ and —$R^2$ may be joined to form a 3 to 8-membered ring; and optionally, both —$R^9$ together with the nitrogen to which they are attached form a heterocyclic ring;

wherein -L¹- is substituted with -L²-Z or -L²-Z' and wherein -L¹- is optionally further substituted;
wherein
-L²- is a single chemical bond or a spacer;
—Z is a water-soluble carrier; and
—Z' is a water-insoluble carrier.

Only in the context of formula (IV) the terms used have the following meaning:

The term "alkyl" as used herein includes linear, branched or cyclic saturated hydrocarbon groups of 1 to 8 carbons, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds.

The term "alkynyl" includes non-aromatic unsaturated hydrocarbons with carbon-carbon triple bonds.

The term "aryl" includes aromatic hydrocarbon groups of 6 to 18 carbons, preferably 6 to 10 carbons, including groups such as phenyl, naphthyl, and anthracenyl. The term "heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instance, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4 to 8 membered aromatic or non-aromatic ring comprising 3 to 7 carbon atoms and at least one N, O, or S atom. Examples are piperidinyl, piperazinyl, tetrahydropyranyl, pyrrolidine, and tetrahydrofuranyl, as well as the exemplary groups provided for the term "heteroaryl" above.

When a ring system is optionally substituted, suitable substituents are selected from the group consisting of alkyl, alkenyl, alkynyl, or an additional ring, each optionally further substituted. Optional substituents on any group, including the above, include halo, nitro, cyano, —OR, —SR, —NR₂, —OCOR, —NRCOR, —COOR, —CONR₂, —SOR, —SO₂R, —SONR₂, —SO₂N R₂, wherein each R is independently alkyl, alkenyl, alkynyl, aryl or heteroaryl, or two R groups taken together with the atoms to which they are attached form a ring.

Preferably -L¹- of formula (IV) is substituted with one moiety -L²-Z or -L²-Z'.

An additional preferred embodiment for -L¹- is disclosed in WO2013/036857A1, which is herewith incorporated by reference in its entirety. Accordingly, a preferred moiety -L¹- is of formula (V):

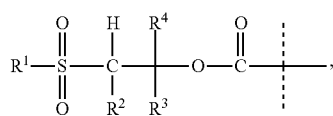

wherein
the dashed line indicates attachment to -D which is a PTH moiety and wherein attachment is through an amine functional group of -D;
—R¹ is selected from the group consisting of optionally substituted C₁-C₆ linear, branched, or cyclic alkyl; optionally substituted aryl; optionally substituted heteroaryl; alkoxy; and —NR⁵₂;
—R² is selected from the group consisting of —H; optionally substituted C₁-C₆ alkyl; optionally substituted aryl; and optionally substituted heteroaryl;
—R³ is selected from the group consisting of —H; optionally substituted C₁-C₆ alkyl; optionally substituted aryl; and optionally substituted heteroaryl;
—R⁴ is selected from the group consisting of —H; optionally substituted C₁-C₆ alkyl; optionally substituted aryl; and optionally substituted heteroaryl;
each —R⁵ is independently of each other selected from the group consisting of —H; optionally substituted C₁-C₆ alkyl; optionally substituted aryl; and optionally substituted heteroaryl; or when taken together two —R⁵ can be cycloalkyl or cycloheteroalkyl;
wherein -L¹- is substituted with -L²-Z or -L²-Z' and wherein -L¹- is optionally further substituted;
wherein
-L²- is a single chemical bond or a spacer;
—Z is a water-soluble carrier; and
—Z' is a water-insoluble carrier.

Only in the context of formula (V) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 C.

"Aryl" includes aromatic hydrocarbon groups of 6-18 carbons, preferably 6-10 carbons, including groups such as phenyl, naphthyl, and anthracene "Heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiszolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms. Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketne; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

Preferably -L¹- of formula (V) is substituted with one moiety -L²-Z or -L²-Z'.

A further preferred embodiment for -L¹- is disclosed in U.S. Pat. No. 7,585,837B2, which is herewith incorporated by reference in its entirety. Accordingly, a preferred moiety -L¹- is of formula (VI):

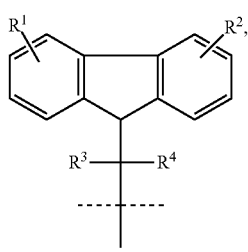

(VI)

wherein
the dashed line indicates attachment to -D which is a PTH moiety and wherein attachment is through an amine functional group of -D;
R¹ and R² are independently selected from the group consisting of hydrogen, alkyl, alkoxy, alkoxyalkyl, aryl, alkaryl, aralkyl, halogen, nitro, —SO₃H, —SO₂NHR⁵, amino, ammonium, carboxyl, PO₃H₂, and OPO₃H₂;
R³, R⁴, and R⁵ are independently selected from the group consisting of hydrogen, alkyl, and aryl;
wherein -L¹- is substituted with -L²-Z or -L²-Z' and wherein -L¹- is optionally further substituted;
wherein
-L²- is a single chemical bond or a spacer;
—Z is a water-soluble carrier; and
—Z' is a water-insoluble carrier.

Suitable substituents for formulas (VI) are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

Only in the context of formula (VI) the terms used have the following meaning:

The terms "alkyl", "alkoxy", "alkoxyalkyl", "aryl", "alkaryl" and "aralkyl" mean alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

Preferably -L¹- of formula (VI) is substituted with one moiety -L²-Z or -L²-Z'.

A further preferred embodiment for -L¹- is disclosed in WO2002/089789A1, which is herewith incorporated by reference in its entirety. Accordingly, a preferred moiety -L¹- is of formula (VII):

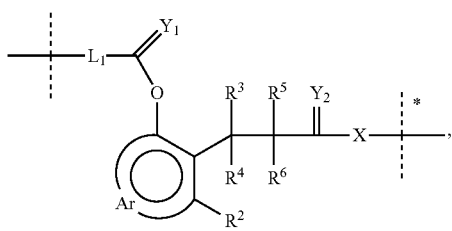

(VII)

wherein
the dashed line indicates attachment to -D which is a PTH moiety and wherein attachment is through an amine functional group of -D;
L₁ is a bifunctional linking group,
Y₁ and Y₂ are independently O, S or NR⁷;
R², R³, R⁴, R⁵, R⁶ and R⁷ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;
Ar is a moiety which when included in formula (VII) forms a multisubstituted aromatic hydrocarbon or a multi-substituted heterocyclic group;
X is a chemical bond or a moiety that is actively transported into a target cell, a hydrophobic moiety, or a combination thereof,
y is 0 or 1;
wherein -L¹- is substituted with -L²-Z or -L²-Z' and wherein -L¹- is optionally further substituted;
wherein
-L²- is a single chemical bond or a spacer;
—Z is a water-soluble carrier; and
—Z' is a water-insoluble carrier.

Only in the context of formula (VII) the terms used have the following meaning:

The term "alkyl" shall be understood to include, e.g. straight, branched, substituted $C_{1-12}$ alkyls, including alkoxy, $C_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxyalkyls, aminoalkyls, dialkylaminos, hydroxyalkyls and mercaptoalkyls; substtued cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophone; alkoxy includes moieieties such as methoxy; and phenoxy includes moieties such as 3-nitrophenoxy. Halo-shall be understood to include fluoro, chloro, iodo and bromo.

Preferably -L¹- of formula (VII) is substituted with one moiety -L²-Z or -L²-Z'.

In another preferred embodiment -L¹- comprises a substructure of formula (VIII)

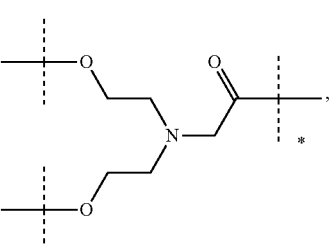

(VIII)

wherein
the dashed line marked with the asterisk indicates attachment to a nitrogen of -D which is a PTH moiety by forming an amide bond;

the unmarked dashed lines indicate attachment to the remainder of -L$^1$-; and wherein -L$^1$- is substituted with -L$^2$-Z or -L$^2$-Z' and wherein -L$^1$- is optionally further substituted;

wherein

-L$^2$- is a single chemical bond or a spacer;

—Z is a water-soluble carrier; and

—Z' is a water-insoluble carrier.

Preferably -L$^1$- of formula (VIII) is substituted with one moiety -L$^2$-Z or -L$^2$-Z'.

In one embodiment -L$^1$- of formula (VIII) is not further substituted.

In another preferred embodiment -L$^1$- comprises a substructure of formula (IX)

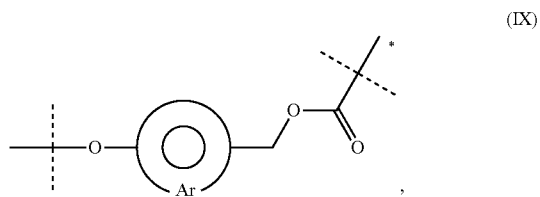

(IX)

wherein the dashed line marked with the asterisk indicates attachment to a nitrogen of -D which is a PTH moiety by forming a carbamate bond;

the unmarked dashed lines indicate attachment to the remainder of -L$^1$-; and wherein -L$^1$- is substituted with -L$^2$-Z or -L$^2$-Z' and wherein -L$^1$- is optionally further substituted;

wherein

-L$^2$- is a single chemical bond or a spacer;

—Z is a water-soluble carrier; and

—Z' is a water-insoluble carrier.

Preferably -L$^1$- of formula (IX) is substituted with one moiety -L$^2$-Z or -L$^2$-Z'.

In one embodiment -L$^1$- of formula (IX) is not further substituted.

In the prodrugs for use of the present invention -L$^2$- is a chemical bond or a spacer moiety.

In one embodiment -L$^2$- is a chemical bond.

In another embodiment -L$^2$- is a spacer moiety.

When -L$^2$- is other than a single chemical bond, -L$^2$- is preferably selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently of each other selected from the group consisting of —H, -T, C$_{1-50}$ alkyl, C$_{2-50}$ alkenyl, and C$_{2-50}$ alkynyl; wherein -T, C$_{1-50}$ alkyl, C$_{2-50}$ alkenyl, and C$_{2-50}$ alkynyl are optionally substituted with one or more —R$^{y2}$, which are the same or different, and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(—R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —R$^{y2}$, which are the same or different;

each —R$^{y2}$ is independently selected from the group consisting of halogen, —CN, oxo (=O), —COOR$^{y5}$, —OR$^{y5}$, —C(O)R$^{y5}$, —C(O)N(R$^{y5}$R$^{y5}$a), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{y3a}$, —R$^{y4}$, —R$^{y4a}$, R$^{y5}$, —R$^{y5a}$ and —R$^{y5b}$ is independently selected from the group consisting of —H, and C$_{1-6}$ alkyl, wherein C$_{1-6}$ alkyl is optionally substituted with one or more halogen, which are the same or different.

When -L$^2$- is other than a single chemical bond, -L$^2$- is even more preferably selected from -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$—, —N(R$^{y1}$)C(O)N(R$^{y1a}$—OC(O)N(R$^{y1}$)—, C$_{1-50}$ alkyl, C$_{2-50}$ alkenyl, and C$_{2-50}$ alkynyl; wherein -T-, C$_{1-20}$ alkyl, C$_{2-20}$ alkenyl, and C$_{2-20}$ alkynyl are optionally substituted with one or more —R$^{y2}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently of each other selected from the group consisting of —H, -T, C$_{1-10}$ alkyl, C$_{2-10}$ alkenyl, and C$_{2-10}$ alkynyl; wherein -T, C$_{1-10}$ alkyl, C$_{2-10}$ alkenyl, and C$_{2-10}$ alkynyl are optionally substituted with one or more —R$^{y2}$, which are the same or different, and wherein C$_{1-10}$ alkyl, C$_{2-10}$ alkenyl, and C$_{2-10}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

wherein each T is independently optionally substituted with one or more —R$^{y2}$, which are the same or different;

—R$^{y2}$ is selected from the group consisting of halogen, —CN, oxo (=O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

When -L$^2$- is other than a single chemical bond, -L$^2$- is even more preferably selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently selected from the group consisting of —H, -T, C$_{1-10}$ alkyl, C$_{2-10}$ alkenyl, and C$_{2-10}$ alkynyl;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —R$^{y2}$ is independently selected from the group consisting of halogen, and C$_{1-6}$ alkyl; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

Even more preferably, -L$^2$- is a C$_{1-20}$ alkyl chain, which is optionally interrupted by one or more groups independently selected from —O—, -T- and —C(O)N(R$^{y1}$)—; and which C$_{1-20}$ alkyl chain is optionally substituted with one or more groups independently selected from —OH, -T and —C(O)N(R$^{y6}$R$^{y6a}$); wherein —R$^{y1}$, —R$^{y6}$, —R$^{y6a}$ are independently selected from the group consisting of H and C$_{1-4}$ alkyl and wherein T is selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

Preferably, -L$^2$- has a molecular weight in the range of from 14 g/mol to 750 g/mol.

Preferably, -L$^2$- comprises a moiety selected from

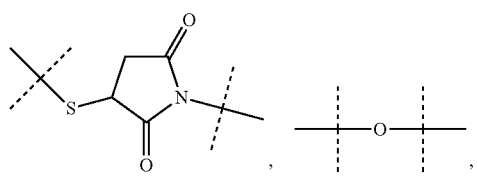

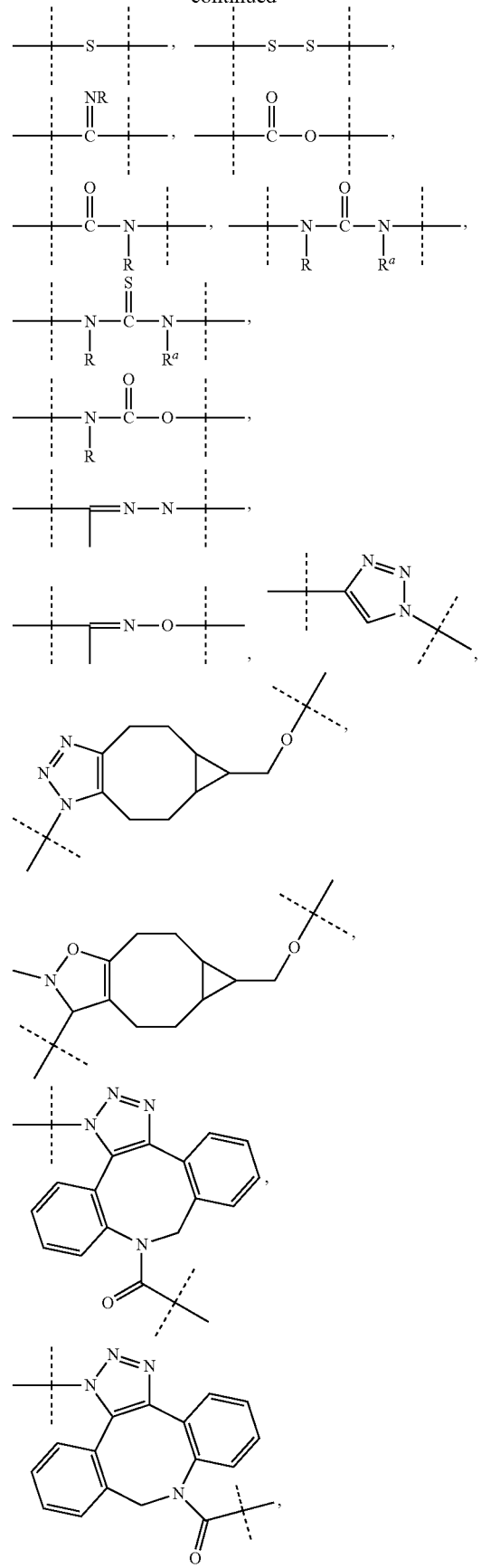

-continued

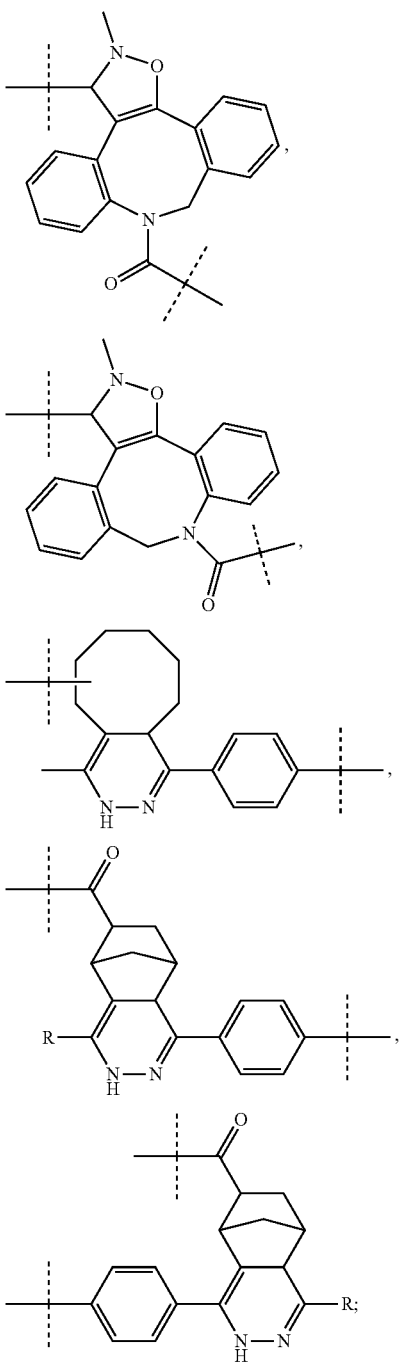

wherein
dashed lines indicate attachment to the rest of -L²-, -L¹-, —Z and/or —Z', respectively; and —R and —R$^a$ are independently of each other selected from the group consisting of —H, methyl, ethyl, propyl, butyl, pentyl and hexyl.

In one preferred embodiment -L²- has a chain lengths of 1 to 20 atoms.

As used herein the term "chain length" with regard to the moiety -L²- refers to the number of atoms of -L²- present in the shortest connection between -L¹- and —Z.

Preferably, -L²- is of formula (i)

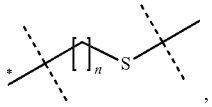

(i)

wherein
the dashed line marked with the asterisk indicates attachment to -L¹-;
the unmarked dashed line indicates attachment to —Z or —Z';
n is selected from the group consisting of 0, 1, 2, 3, 4, 5, 6, 7, 8, 9, 10, 11, 12, 13, 14, 15, 16, 17 and 18; and
wherein the moiety of formula (i) is optionally further substituted.

Preferably, n of formula (i) is selected from the group consisting of 3, 4, 5, 6, 7, 8, and 9. Even more preferably n of formula (i) is 4, 5, 6, or 7. In one embodiment n of formula (i) is 4. In another embodiment n of formula (i) is 5. In another embodiment n of formula (i) is 6.

In another preferred embodiment the moiety -L¹-L²- is selected from the group consisting of

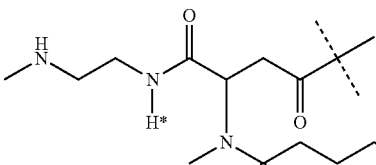

(IIca-i)

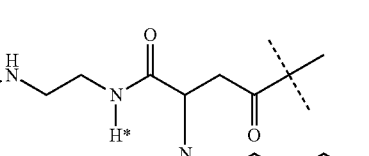

(IIca-ii)

and

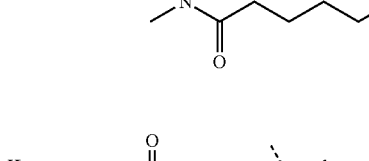

(IIca-iii)

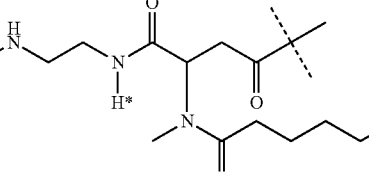

wherein
the unmarked dashed line indicates the attachment to a nitrogen of -D which is a PTH moiety by forming an amide bond; and
the dashed line marked with the asterisk indicates attachment to —Z or —Z'.

In one preferred embodiment the moiety -L$^1$-L$^2$- is selected from the group consisting of

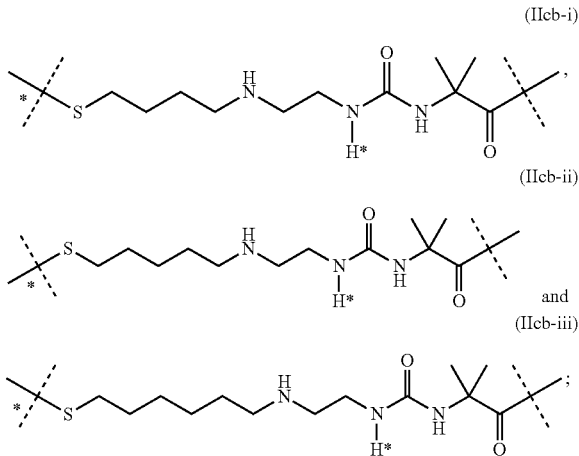

wherein
the unmarked dashed line indicates the attachment to a nitrogen of -D which is a PTH moiety by forming an amide bond; and
the dashed line marked with the asterisk indicates attachment to —Z or —Z'.

In a preferred embodiment the moiety -L$^1$-L$^2$- is of formula (IIca-ii).

In another preferred embodiment the moiety -L$^1$-L$^2$- is of formula (IIcb-iii).

Preferably, the controlled-release PTH compound for use of the present invention is of formula (Ia) with x=1.

The carrier —Z comprises a C$_{8-24}$ alkyl or a polymer. Preferably, —Z comprises a polymer, preferably a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

Preferably, —Z has a molecular weight ranging from 5 to 200 kDa. Even more preferably, —Z has a molecular weight ranging from 8 to 100 kDa, even more preferably ranging from 10 to 80 kDa, even more preferably from 12 to 60, even more preferably from 15 to 40 and most preferably —Z has a molecular weight of about 20 kDa. In another equally preferred embodiment —Z has a molecular weight of about 40 kDa.

In one embodiment such water-soluble carrier —Z comprises a protein. Preferred proteins are selected from the group consisting of carboxyl-terminal polypeptide of the chorionic gonadotropin as described in US 2012/0035101 A1 which are herewith incorporated by reference; albumin; XTEN sequences as described in WO 2011123813 A2 which are herewith incorporated by reference; proline/alanine random coil sequences as described in WO 2011/144756 A1 which are herewith incorporated by reference; proline/alanine/serine random coil sequences as described in WO 2008/155134 A1 and WO 2013/024049 A1 which are herewith incorporated by reference; and Fc fusion proteins.

In one embodiment —Z is a polysarcosine.

In another preferred embodiment —Z comprises a poly(N-methylglycine).

In a particularly preferred embodiment —Z comprises a random coil protein moiety.

In one preferred embodiment —Z comprises one random coil protein moiety.

In another preferred embodiment —Z comprises two random coil proteins moieties.

In another preferred embodiment —Z comprises three random coil proteins moieties.

In another preferred embodiment —Z comprises four random coil proteins moieties.

In another preferred embodiment —Z comprises five random coil proteins moieties.

In another preferred embodiment —Z comprises six random coil proteins moieties.

In another preferred embodiment —Z comprises seven random coil proteins moieties.

In another preferred embodiment —Z comprises eight random coil proteins moieties.

Preferably such random coil protein moiety comprises at least 25 amino acid residues and at most 2000 amino acids. Even more preferably such random coil protein moiety comprises at least 30 amino acid residues and at most 1500 amino acid residues. Even more preferably such random coil protein moiety comprises at least 50 amino acid residues and at most 500 amino acid residues.

In a preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine and proline. Even more preferably, at least 10%, but less than 75%, preferably less than 65%, of the total number of amino acid residues of such random coil protein moiety are proline residues. Preferably, such random coil protein moiety is as described in WO 2011/144756 A1 which is hereby incorporated by reference in its entirety. Even more preferably —Z comprises at least one moiety selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:51 and SEQ ID NO:61 as disclosed in WO2011/144756 which are hereby incorporated by reference. A moiety comprising such random coil protein comprising alanine and proline will be referred to as "PA" or "PA moiety".

Accordingly, —Z comprises a PA moiety.

In an equally preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, serine and proline. Even more preferably, at least 4%, but less than 40% of the total number of amino acid residues of such random coil protein moiety are proline residues. Preferably, such random coil protein moiety is as described in WO 2008/155134 A1 which is hereby incorporated by reference in its entirety. Even more preferably —Z comprises at least one moiety selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:40, SEQ ID NO:42, SEQ ID NO:44, SEQ ID NO:46, SEQ ID NO:50, SEQ ID NO:52, SEQ ID NO:54 and SEQ ID NO:56 as disclosed in WO 2008/155134 A1, which are hereby incorporated by reference. A moiety comprising such random coil protein moiety comprising alanine, serine and proline will be referred to as "PAS" or "PAS moiety".

Accordingly, —Z comprises a PAS moiety.

In an equally preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine and proline. A moiety comprising such random coil protein moiety comprising alanine, glycine and proline will be referred to as "PAG" or "PAG moiety".

Accordingly, —Z comprises a PAG moiety.

In an equally preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from proline and glycine. A moiety comprising such random coil protein moiety comprising proline and glycine will be referred to as "PG" or "PG moiety".

Preferably, such PG moiety comprises a moiety of formula (a-0)

$$[(Gly)_p\text{-Pro-}(Gly)_q]_r \quad (a\text{-}0);$$

wherein p is selected from the group consisting of 0, 1, 2, 3, 4 and 5;

q is selected from the group consisting of 0, 1, 2, 3, 4 and 5;

r is an integer ranging from and including 10 to 1000;

provided that at least one of p and q is at least 1;

Preferably, p of formula (a-0) is selected from the group consisting of 1, 2 and 3.

Preferably, q of formula (a-0) is selected from 0, 1 and 2.

Even more preferably the PG moiety comprises the sequence of SEQ ID NO:122:

GGPGGPGPGGPGGPGPGGPG

Even more preferably, the PG moiety comprises the sequence of formula (a-0-a)

$$(GGPGGPGPGGPGGPGPGGPG)_v \quad (a\text{-}0\text{-}a),$$

wherein v is an integer ranging from and including 1 to 50.

It is understood that the sequence of formula (a-0-a) comprises v replicates of the sequence of SEQ ID NO:122.

Accordingly, —Z comprises a PG moiety.

In an equally preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine, serine, threonine, glutamate and proline. Preferably, such random coil protein moiety is as described in WO 2010/091122 A1 which is hereby incorporated by reference. Even more preferably —Z comprises at least one moiety selected from the group consisting of SEQ ID NO:182, SEQ ID NO:183, SEQ ID NO:184; SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:1715, SEQ ID NO:1716, SEQ ID NO:1718, SEQ ID NO:1719, SEQ ID NO:1720, SEQ ID NO:1721 and SEQ ID NO:1722 as disclosed in WO2010/091122A1, which are hereby incorporated by reference. A moiety comprising such random coil protein moiety comprising alanine, glycine, serine, threonine, glutamate and proline will be referred to as "XTEN" or "XTEN moiety" in line with its designation in WO 2010/091122 A1.

Accordingly, —Z comprises an XTEN moiety.

In another preferred embodiment, —Z comprises a fatty acid derivate. Preferred fatty acid derivatives are those disclosed in WO 2005/027978 A2 and WO 2014/060512 A1 which are herewith incorporated by reference.

In another preferred embodiment —Z is a hyaluronic acid-based polymer.

In one embodiment —Z is a carrier.

In another embodiment —Z is a carrier as disclosed in WO 2013/024048 A1 which is herewith incorporated by reference.

In another preferred embodiment —Z is a PEG-based polymer, such as a linear, branched or multi-arm PEG-based polymer.

In one embodiment —Z is a linear PEG-based polymer.

In another embodiment —Z is a multi-arm PEG-based polymer. Preferably, —Z is a multi-arm PEG-based polymer having at least 4 PEG-based arms.

Preferably, such multi-arm PEG-based polymer —Z is connected to a multitude of moieties -L²-L¹-D, wherein each moiety -L²-L¹-D is preferably connected to the end of an arm, preferably to the end of an arm. Preferably such multi-arm PEG-based polymer —Z is connected to 2, 3, 4, 5, 6, 7, 8, 9, 10, 11, 12, 13, 14, 15 or 16 moieties -L²-L¹-D. Even more preferably such multi-arm PEG-based polymer —Z is connected to 2, 3, 4, 6 or 8 moieties -L²-L¹-D. Even more preferably such multi-arm PEG-based polymer —Z is connected to 2, 4 or 6 moieties -L²-L¹-D, even more preferably such multi-arm PEG-based polymer —Z is connected to 4 or 6 moieties -L²-L¹-D, and most preferably such multi-arm PEG-based polymer —Z is connected to 4 moieties -L²-L¹-D.

Preferably, such multi-arm PEG-based polymer —Z is a multi-arm PEG derivative as, for instance, detailed in the products list of JenKem Technology, USA (accessed by download from www.jenkemusa.com at the path/Pages/PEGProducts.aspx on Dec. 18, 2014), such as a 4-arm-PEG derivative, in particular a 4-arm-PEG comprising a pentaerythritol core, an 8-arm-PEG derivative comprising a hexaglycerin core, and an 8-arm-PEG derivative comprising a tripentaerythritol core. More preferably, the water-soluble PEG-based carrier —Z comprises a moiety selected from:

a 4-arm PEG Amine comprising a pentaerythritol core:

with n ranging from 20 to 500;
an 8-arm PEG Amine comprising a hexaglycerin core:

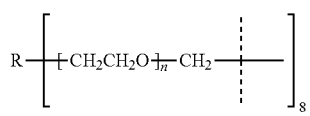

with n ranging from 20 to 500; and
R=hexaglycerin or tripentaerythritol core structure; and
a 6-arm PEG Amine comprising a sorbitol or dipentaerythritol core:

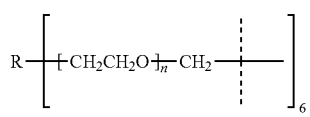

with n ranging from 20 to 500; and
R=comprising a sorbitol or dipentaerythritol core;
and wherein dashed lines indicate attachment to the rest of the PTH prodrug.

In a preferred embodiment —Z is a branched PEG-based polymer. In one embodiment —Z is a branched PEG-based polymer having one, two, three, four, five or six branching points. Preferably, —Z is a branched PEG-based polymer having one, two or three branching points. In one embodiment —Z is a branched PEG-based polymer having one branching point. In another embodiment —Z is a branched PEG-based polymer having two branching points. In another embodiment —Z is a branched PEG-based polymer having three branching points.

A branching point is preferably selected from the group consisting of —N<, —CH< and >C<.

Preferably, such branched PEG-based moiety —Z has a molecular weight of at least 10 kDa.

In one embodiment such branched moiety —Z has a molecular weight ranging from and including 10 kDa to 500 kDa, more preferably ranging from and including 10 kDa to 250 Da, even more preferably ranging from and including 10 kDa to 150 kDa, even more preferably ranging from and including 12 kDa to 100 kDa and most preferably ranging from and including 15 kDa to 80 kDa.

Preferably, such branched moiety —Z has a molecular weight ranging from and including 10 kDa to 80 kDa. In one embodiment the molecular weight is about 10 kDa. In another embodiment the molecular weight of such branched moiety —Z is about 20 kDa. In another embodiment the molecular weight of such branched moiety —Z is about 30 kDa. In another embodiment the molecular weight of such a branched moiety —Z is about 40 kDa. In another embodiment the molecular weight of such a branched moiety —Z is about 50 kDa. In another embodiment the molecular weight of such a branched moiety —Z is about 60 kDa. In another embodiment the molecular weight of such a branched moiety —Z is about 70 kDa. In another embodiment the molecular weight of such a branched moiety —Z is about 80 kDa. Most preferably, such branched moiety —Z has a molecular weight of about 40 kDa.

Preferably, —Z or —Z' comprises a moiety

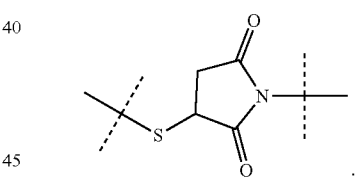

In an equally preferred embodiment —Z comprises an amide bond.

Preferably —Z comprises a moiety of formula (a)

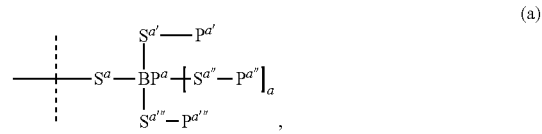

(a)

wherein
the dashed line indicates attachment to -L²- or to the remainder of —Z;
$BP^a$ is a branching point selected from the group consisting of —N<, —CR< and >C<;
—R is selected from the group consisting of —H and $C_{1-6}$ alkyl;

a is 0 if $BP^a$ is —N< or —CR< and n is 1 if $BP^a$ is >C<;

—$S^a$—, —$S^{a'}$—, —$S^{a''}$— and —$S^{a'''}$— are independently of each other a chemical bond or are selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more —$R^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^2$)—, —S(O)$_2$N($R^2$)—, —S(O)N($R^2$)—, —S(O)$_2$—, —S(O)—, —N($R^2$)S(O)$_2$N($R^{2a}$)—, —S—, —N($R^2$)—, —OC(O$R^2$)($R^{2a}$)—, —N($R^2$)C(O)N($R^{2a}$)—, and —OC(O)N($R^2$)—; each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —$R^1$, which are the same or different;

each —$R^1$ is independently selected from the group consisting of halogen, —CN, oxo (=O), —COO$R^3$, —O$R^3$, —C(O)$R^3$, —C(O)N($R^3R^{3a}$), —S(O)$_2$N($R^3R^{3a}$), —S(O)N($R^3R^{3a}$), —S(O)$_2R^3$, —S(O)$R^3$, —N($R^3$)S(O)$^2$N($R^{3a}R^{3b}$), —S$R^3$, —N($R^3R^{3a}$), —NO$_2$, —OC(O)$R^3$, —N($R^3$)C(O)$R^{3a}$, —N($R^3$)S(O)$_2R^{3a}$, —N($R^3$)S(O)$R^{3a}$, —N($R^3$)C(O)O$R^{3a}$, —N($R^3$)C(O)N($R^{3a}R^{3b}$), —OC(O)N($R^3R^{3a}$), and $C_{1-6}$ alkyl; wherein $C_{1-6}$ alkyl is optionally substituted with one or more halogen, which are the same or different;

each —$R^2$, —$R^{2a}$, —$R^3$, —$R^{3a}$ and —$R^{3b}$ is independently selected from the group consisting of —H, and $C_{1-6}$ alkyl, wherein $C_{1-6}$ alkyl is optionally substituted with one or more halogen, which are the same or different; and —$P^{a'}$, —$P^{a''}$ and —$P^{a'''}$ are independently a polymeric moiety.

In one embodiment $BP^a$ of formula (a) is —N<.

In another embodiment $BP^a$ of formula (a) is >C<.

In a preferred embodiment $BP^a$ of formula (a) is —CR<. Preferably, —R is —H. Accordingly, a of formula (a) is 0.

In one embodiment —$S^a$— of formula (a) is a chemical bond.

In another embodiment —$S^a$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of -T-, —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(O$R^4$)($R^{4a}$)—, N($R^4$)C(O)N($R^{4a}$)—, and —OC(O)N($R^4$)—; wherein -T- is a 3- to 10-membered heterocyclyl; and —$R^4$ and —$R^{4a}$ are independently selected from the group consisting of —H, methyl, ethyl, propyl and butyl.

Preferably —$S^a$— of formula (a) is selected from the group consisting of $C_{1-10}$ alkyl which is interrupted by one or more chemical groups selected from the group consisting of -T-, —C(O)N($R^4$)— and —O—.

In one embodiment —$S^{a'}$— of formula (a) is a chemical bond.

In another embodiment of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(O$R^4$)($R^{4a}$)N($R^4$)C(O)N($R^{4a}$) and —OC(O)N($R^4$)—; wherein —$R^4$ and —$R^{4a}$ are independently selected from the group consisting of —H, methyl, ethyl, propyl and butyl. Preferably —$S^{a'}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In one embodiment —$S$— of formula (a) is a chemical bond.

In another embodiment —$S^{a''}$ of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(O$R^4$)($R^{4a}$)—, N($R^4$)C(O)N($R^{4a}$) and —OC(O)N($R^4$)—; wherein —$R^4$ and —$R^{4a}$ are independently selected from the group consisting of —H, methyl, ethyl, propyl and butyl. Preferably —$S^{a''}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In one embodiment —$S^{a''}$— of formula (a) is a chemical bond.

In another embodiment —$S^{a'''}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(O$R^4$)($R^{4a}$)—, N($R^4$)C(O)N($R^{4a}$) and —OC(O)N($R^4$)—; wherein —$R^4$ and —$R^{4a}$ are independently selected from the group consisting of —H, methyl, ethyl, propyl and butyl. Preferably —$S^{a'}$— of formula (a) is selected from the group consisting of methyl, ethyl, propyl, butyl, which are optionally interrupted by one or more chemical groups selected from the group consisting of —O—, —C(O)— and —C(O)N($R^4$)—.

Preferably, —$P^{a'}$, —$P^{a''}$ and —$P^{a'''}$ of formula (a) independently comprise a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

More preferably, —$P^{a'}$, —$P^{a''}$ and —$P^{a'''}$ of formula (a) independently comprise a PEG-based moiety. Even more preferably, —$P^{a'}$, —$P^{a''}$ and —$P^{a'''}$ of formula (a) independently comprise a PEG-based moiety comprising at least 20% PEG, even more preferably at least 30%, even more preferably at least 40% PEG, even more preferably at least 50% PEG, even more preferably at least 60% PEG, even more preferably at least 70% PEG, even more preferably at least 80% PEG and most preferably at least 90% PEG.

Preferably, —$P^{a'}$, —$P^{a''}$ and —$P^{a'''}$ of formula (a) independently have a molecular weight ranging from and including 5 kDa to 50 kDa, more preferably have a molecular weight ranging from and including 5 kDa to 40 kDa, even more preferably ranging from and including 7.5 kDa to 35 kDa, even more preferably ranging from and 7.5 to 30 kDa, even more preferably ranging from and including 10 to 30 kDa.

In one embodiment —$P^{a'}$, —$P^{a'''}$ and —$P^{a'''}$ of formula (a) have a molecular weight of about 5 kDa.

In another embodiment —$P^{a'}$, —$P^{a''}$ and —$P^{a'''}$ of formula (a) have a molecular weight of about 7.5 kDa.

In another embodiment —$P^{a'}$, —$P^{a''}$ and —$P^{a'''}$ of formula (a) have a molecular weight of about 10 kDa.

In another embodiment —$P^{a'}$, —$P^{a''}$ and —$P^{a'''}$ of formula (a) have a molecular weight of about 12.5 kDa.

In another embodiment —$P^{a'}$, —$P^{a''}$ and —$P^{a'''}$ of formula (a) have a molecular weight of about 15 kDa.

In another embodiment —$P^{a'}$, —$P^{a''}$ and —$P^{a'''}$ of formula (a) have a molecular weight of about 20 kDa.

In one embodiment —Z comprises one moiety of formula (a).

In another embodiment —Z comprises two moieties of formula (a).

In another embodiment —Z comprises three moieties of formula (a).

Preferably, —Z is a moiety of formula (a).

More preferably, —Z comprises a moiety of formula (b) a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly (caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropyl-methacrylamides), poly(hydroxypropyl methacrylates), poly (hydroxypropyloxazolines), poly(iminocarbonates), poly (lactic acids), poly(lactic-co-glycolic acids), poly (methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

If the carrier —Z' is a hydrogel, it is preferably a hydrogel comprising PEG or hyaluronic acid. Most preferably such hydrogel comprises PEG.

Even more preferably, the carrier —Z' is a hydrogel as described in WO 2006/003014 A2, WO 2011/012715 A1 or WO 2014/056926 A1, which are herewith incorporated by reference in their entirety.

In another embodiment —Z' is a polymer network formed through the physical aggregation of polymer chains, which physical aggregation is preferably caused by hydrogen bonds, crystallization, helix formation or complexation. In

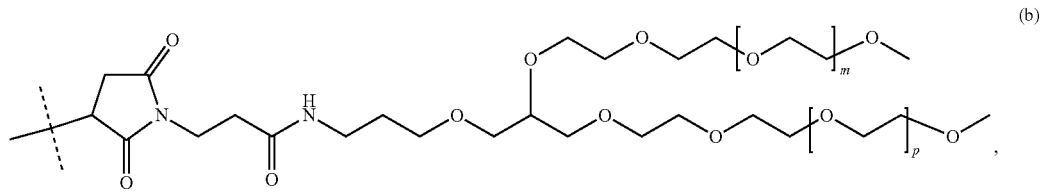

(b)

wherein
the dashed line indicates attachment to -$L^2$- or to the remainder of —Z; and
m and p are independently of each other an integer ranging from and including 150 to 1000; preferably an integer ranging from and including 150 to 500; more preferably an integer ranging from and including 200 to 500; and most preferably an integer ranging from and including 400 to 500.

Preferably, m and p of formula (b) are the same integer.

Most preferably m and p of formula (b) are about 450.

Preferably, —Z is a moiety of formula (b).

The carrier —Z' is a water-insoluble polymer, even more preferably a hydrogel. Preferably, such hydrogel comprises one embodiment such polymer network is a thermogelling polymer.

If the controlled-release PTH compound for use of the present invention is a prodrug, its total mass is preferably at least 10 kDa, such as at least 12 kDa, such as at least 15 kDa, such as at least 20 kDa or such as at least 30 kDa. If the controlled-release PTH compound is a water-soluble prodrug, its total mass preferably is at most 250 kDa, such as at most 200 kDa, 180 kDa, 150 kDa or 100 kDa. It is understood that no meaningful upper molecular weight limit can be provided in case the controlled-release PTH compound is water-insoluble.

In a preferred embodiment the controlled-release PTH compound is of formula (IIe-i):

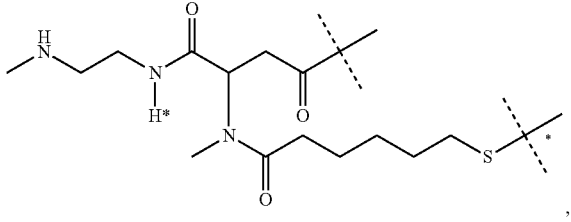
(IIe-i)

wherein
the unmarked dashed line indicates the attachment to a nitrogen of -D which is a PTH moiety by forming an amide bond; and
the dashed line marked with the asterisk indicates attachment to a moiety

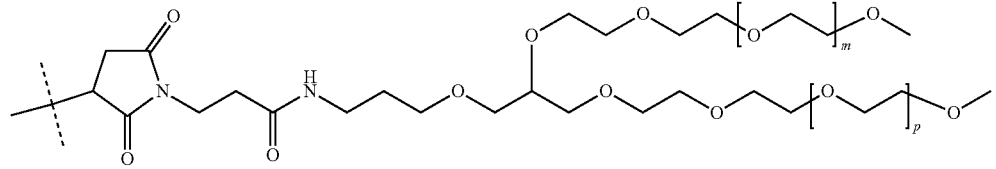

wherein
m and p are independently an integer ranging from and including 400 to 500.

Preferably, -D is attached to the PTH prodrug of formula (IIe-i) through the N-terminal amine functional group of the PTH moiety.

In another preferred embodiment the PTH prodrug for use of the present invention is of formula (IIf-i):

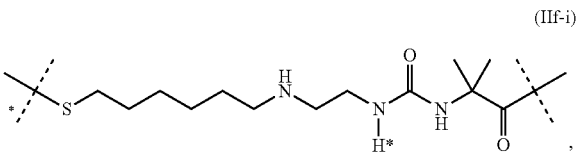
(IIf-i)

wherein
the unmarked dashed line indicates the attachment to a nitrogen of -D which is a PTH moiety by forming an amide bond; and
the dashed line marked with the asterisk indicates attachment to a moiety

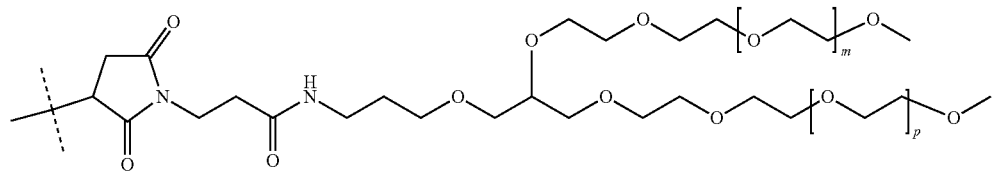

wherein
m and p are independently an integer ranging from and including 400 to 500.

Preferably, -D is attached to the PTH prodrug of formula (IIf-i) through the N-terminal amine functional group of the PTH moiety.

In a preferred embodiment the residual activity of the controlled-release PTH in the form of a PTH prodrug is less than 10%, more preferably less than 1%, even more preferably less than 0.1%, even more preferably less than 0.01%, even more preferably less than 0.001% and most preferably less than 0.0001%.

As used herein the term "residual activity" refers to the activity exhibited by the PTH prodrug with the PTH moiety bound to a carrier in relation to the activity exhibited by the corresponding free PTH. In this context the term "activity" refers to binding to an activation domain of the PTH/PTHrP1 receptor resulting in activation of adenylate cyclase to generate cAMP, phospholipase C to generate intracellular calcium, or osteoblastic expression of RANKL (which binds to RANK (Receptor Activator of Nuclear Factor kB) on osteoclasts. It is understood that measuring the residual activity of the PTH prodrug for use of the present invention takes time during which a certain amount of PTH will be released from the PTH prodrug and that such released PTH may distort the results measured for the PTH prodrug. It is thus accepted practice to test the residual activity of a prodrug with a conjugate in which the drug moiety, in this case PTH, is non-reversibly, i.e. stably, bound to a carrier, which as closely as possible resembles the structure of the PTH prodrug for which residual activity is to be measured.

Preferably, the pharmaceutical composition comprising at least one controlled-release PTH compound for use of the present invention has a pH ranging from and including pH 3 to pH 8. More preferably, the pharmaceutical composition has a pH ranging from and including pH 4 to pH 6. Most preferably, the pharmaceutical composition has a pH ranging from and including pH 4 to pH 5.

In one embodiment the pharmaceutical composition comprising at least one controlled-release PTH compound for use of the present invention is a liquid or suspension formulation. It is understood that the pharmaceutical composition is a suspension formulation if the controlled-release PTH compound for use of the present invention is water-insoluble.

In another embodiment the pharmaceutical composition comprising at least one controlled-release PTH compound for use of the present invention is a dry formulation which is reconstituted before administration to a patient.

Such liquid, suspension, dry or reconstituted pharmaceutical composition comprises at least one excipient. Excipients used in parenteral formulations may be categorized as, for example, buffering agents, isotonicity modifiers, preservatives, stabilizers, anti-adsorption agents, oxidation protection agents, viscosifiers/viscosity enhancing agents, or other auxiliary agents. However, in some cases, one excipient may have dual or triple functions. Preferably, the at least one excipient comprised in the pharmaceutical composition for use of the present invention is selected from the group consisting of (i) Buffering agents: physiologically tolerated buffers to maintain pH in a desired range, such as sodium phosphate, bicarbonate, succinate, histidine, citrate and acetate, sulphate, nitrate, chloride, pyruvate; antacids such as $Mg(OH)_2$ or $ZnCO_3$ may be also used;

(ii) Isotonicity modifiers: to minimize pain that can result from cell damage due to osmotic pressure differences at the injection depot; glycerin and sodium chloride are examples; effective concentrations can be determined by osmometry using an assumed osmolality of 285-315 mOsmol/kg for serum;

(iii) Preservatives and/or antimicrobials: multidose parenteral formulations require the addition of preservatives at a sufficient concentration to minimize risk of patients becoming infected upon injection and corresponding regulatory requirements have been established; typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride;

(iv) Stabilizers: Stabilisation is achieved by strengthening of the protein-stabilising forces, by destabilisation of the denatured state, or by direct binding of excipients to the protein; stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives; in addition, oligomers or polymers such as cyclodextrins, dextran, dendrimers, PEG or PVP or protamine or HSA may be used;

(v) Anti-adsorption agents: Mainly ionic or non-ionic surfactants or other proteins or soluble polymers are used to coat or adsorb competitively to the inner surface of the formulation's container; e.g., poloxamer (Pluronic F-68), PEG dodecyl ether (Brij 35), polysorbate 20 and 80, dextran, polyethylene glycol, PEG-polyhistidine, BSA and HSA and gelatins; chosen concentration and type of excipient depends on the effect to be avoided but typically a monolayer of surfactant is formed at the interface just above the CMC value;

(vi) Oxidation protection agents: antioxidants such as ascorbic acid, ectoine, methionine, glutathione, monothioglycerol, morin, polyethylenimine (PEI), propyl gallate, and vitamin E; chelating agents such as citric acid, EDTA, hexaphosphate, and thioglycolic acid may also be used;

(vii) Viscosifiers or viscosity enhancers: in case of a suspension retard settling of the particles in the vial and syringe and are used in order to facilitate mixing and resuspension of the particles and to make the suspension easier to inject (i.e., low force on the syringe plunger); suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly (hydroxy acids), such as poly(D,L- or L-lactic acid) (PLA) and poly(glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone;

such block copolymers as well as the abovementioned poloxamers may exhibit reverse thermal gelation behavior (fluid state at room temperature to facilitate administration and gel state above sol-gel transition temperature at body temperature after injection);

(viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue; a spreading agent such as but not limited to hyaluronidase temporarily decreases the viscosity of the extracellular matrix and promotes diffusion of injected drugs; and (ix) Other auxiliary agents: such as wetting agents, viscosity modifiers, antibiotics, hyaluronidase; acids and bases such as hydrochloric acid and sodium hydroxide are auxiliary agents necessary for pH adjustment during manufacture.

A further aspect of the present invention is a method of treating, controlling, delaying or preventing in a mammalian patient one or more conditions that can be treated, controlled, delayed or prevented with PTH, comprising the step of administering a pharmaceutical composition comprising at least one controlled-release PTH compound or a pharmaceutically acceptable salt, hydrate or solvate thereof no more frequent than once every 24 hours with a dosage of the controlled-release PTH compound that corresponds to no more than 70% of the molar equivalent dose of PTH 1-84 administered at the same dosing frequency required to maintain serum calcium within normal levels over a 24 hour period.

Preferably, the mammalian patient is a human patient.

Preferred embodiments of, for example, the controlled-release PTH compound, the administration frequency, i.e. the time between two injections, mode of administration and dosage are as described above.

Preferably, the condition that can be treated, controlled, delayed or prevented with PTH is selected from the group consisting of hypoparathyroidism, hyperphosphatemia, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfecta, fibrous dysplasia, rheumatoid arthritis, Paget's disease, humoral hypercalcemia associated with malignancy, osteopenia, periodontal disease, bone fracture, alopecia, chemotherapy-induced alopecia, and thrombocytopenia. More preferably, the condition that can be treated, controlled, delayed or prevented with PTH is selected from the group consisting of hypoparathyroidism, hyperphosphatemia, fracture repair, arthritis, osteoarthritis, rheumatoid arthritis, osteopenia, periodontal disease, bone fracture, alopecia, chemotherapy-induced alopecia, and thrombocytopenia.

Most preferably said condition is hypoparathyroidism.

EXAMPLES

Materials and Methods

Side chain protected PTH(1-34) (SEQ ID NO:51) on TCP resin having Boc protected N-terminus and ivDde protected side chain of Lys26 (synthesized by Fmoc-strategy) was obtained from custom peptide synthesis providers.

Side chain protected PTH(1-34) on TCP resin having Fmoc protected N-terminus (synthesized by Fmoc-strategy) was obtained from custom peptide synthesis providers.

PEG 2×20 kDa maleimide, Sunbright GL2-400MA was purchased from NOF Europe N.V., Grobbendonk, Belgium. S-Trityl-6-mercaptohexanoic acid was purchased from Polypeptide, Strasbourg, France. HATU was obtained from Merck Biosciences GmbH, Schwalbach/Ts, Germany. Fmoc-N-Me-Asp(OBn)-OH was obtained from Peptide International Inc., Louisville, Ky., USA. Fmoc-Aib-OH was purchased from Iris Biotech GmbH, Marktredwitz, Germany. All other chemicals and reagents were purchased from Sigma Aldrich GmbH, Taufkirchen, Germany, unless a different supplier is mentioned.

Compound 11a (examples 11-15) was synthesized following the procedure described in patent WO2009/095479A2, example 1.

Syringes equipped with polyethylenene frits (MultiSyn-Tech GmbH, Witten, Germany) were used as reaction vessels or for washing steps of peptide resins.

General procedure for the removal of ivDde protecting group from side chain protected PTH on resin: The resin was pre-swollen in DMF for 30 min and the solvent was discarded. The ivDde group was removed by incubating the resin with DMF/hydrazine hydrate 4/1 (v/v, 2.5 mL/g resin) for 8×15 min. For each step fresh DMF/hydrazine hydrate solution was used. Finally, the resin was washed with DMF (10 x), DCM (10×) and dried in vacuo.

General procedure for the removal of Fmoc protecting group from protected PTH on resin: The resin was pre-swollen in DMF for 30 min and the solvent was discarded. The Fmoc group was removed by incubating the resin with DMF/piperidine/DBU 96/2/2 (v/v/v, 2.5 mL/g resin) for 3×10 min. For each step fresh DMF/piperidine/DBU hsolution was used. Finally, the resin was washed with DMF (10 x), DCM (10 x) and dried in vacuo.

RP-HPLC Purification:

For preparative RP-HPLC a Waters 600 controller and a 2487 Dual Absorbance Detector was used, equipped with the following columns: Waters XBridge™ BEH300 Prep C18 5 µm, 150×10 mm, flow rate 6 mL/min, or Waters XBridge™ BEH300 Prep C18 10 µm, 150×30 mm, flow rate 40 mL/min. Linear gradients of solvent system A (water containing 0.1% TFA v/v) and solvent system B (acetonitrile containing 0.1% TFA v/v) were used. HPLC fractions containing product were pooled and lyophilized if not stated otherwise.

Flash Chromatography:

Flash chromatography purifications were performed on an Isolera One system from Biotage AB, Sweden, using Biotage KP-Sil silica cartridges and n-heptane and ethyl acetate as eluents. Products were detected at 254 nm.

Ion Exchange Chromatography:

Ion exchange chromatography (IEX) was performed using an Amersham Bioscience AEKTAbasic system equipped with a MacroCap SP cation exchanger column (Amersham Bioscience/GE Healthcare). 17 mM acetic acid pH 4.5 (solvent A) and 17 mM acetic acid, 1 M NaCl, pH 4.5 (solvent B) were used as mobile phases.

Size Exclusion Chromatography:

Size exclusion chromatography (SEC) was performed using an Amersham Bioscience AEKTAbasic system equipped with HiPrep 26/10 desalting columns (Amersham Bioscience/GE Healthcare). 0.1% (v/v) acetic acid was used as mobile phase.

Analytical Methods

Analytical ultra-performance LC (UPLC)-MS was performed on a Waters Acquity system equipped with a Waters BEH300 C18 column (2.1×50 mm, 1.7 µm particle size, flow: 0.25 mL/min; solvent A: water containing 0.04% TFA (v/v), solvent B: acetonitrile containing 0.05% TFA (v/v)) coupled to a LTQ Orbitrap Discovery mass spectrometer from Thermo Scientific or coupled to a Waters Micromass ZQ.

Quantitative measurements of serum calcium (sCa), urinary calcium and serum phosporous (sP) were performed on a Roche-Hitachi P800 modular biochemistry instrument.

Example 1

Synthesis of Linker Reagent 1f

Linker reagent 1f was synthesized according to the following scheme:

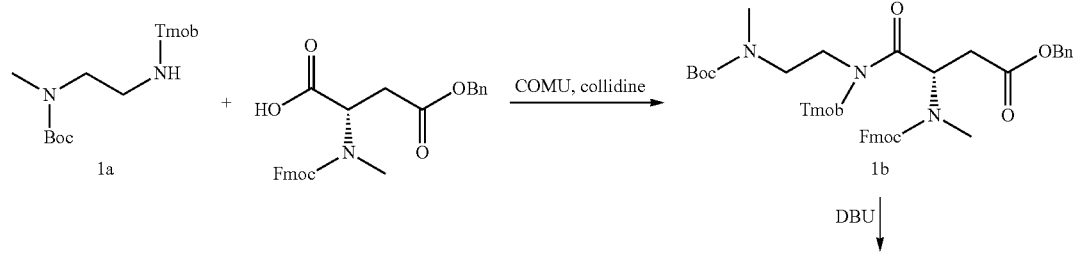

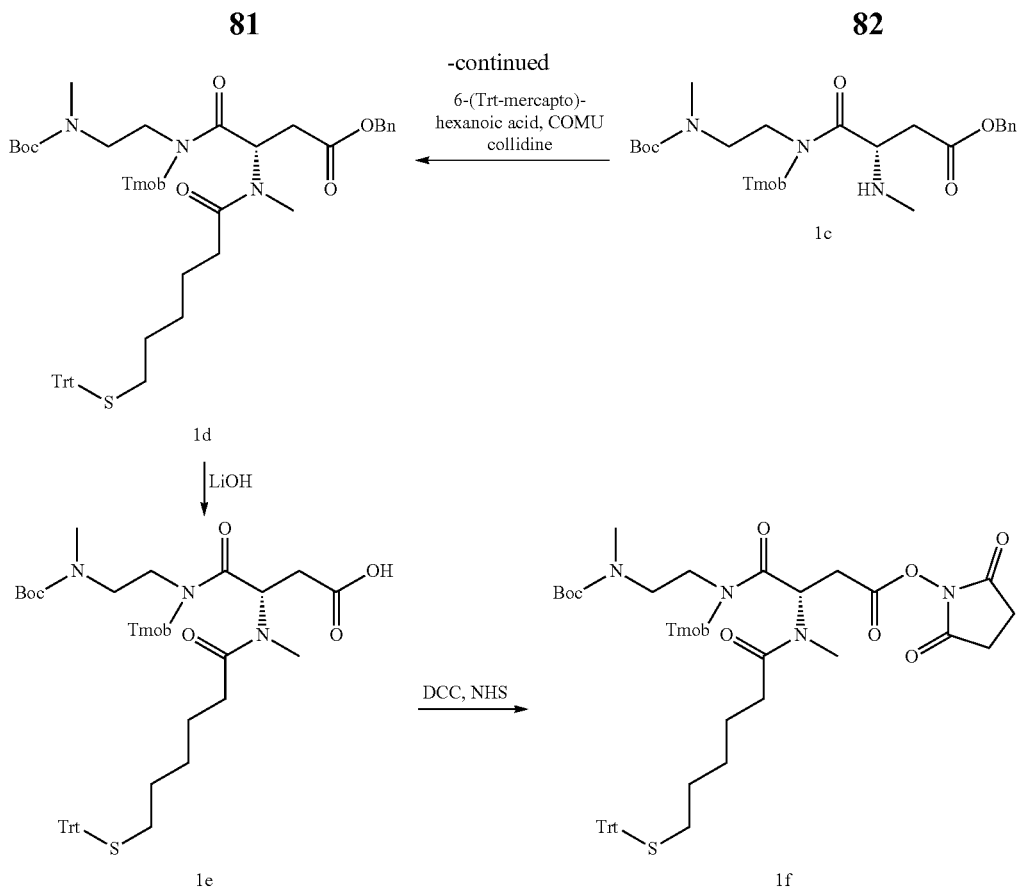

To a solution of N-methyl-N-Boc-ethylenediamine (2 g, 11.48 mmol) and NaCNBH$_3$ (819 mg, 12.63 mmol) in MeOH (20 mL) was added 2,4,6-trimethoxybenzaldehyde (2.08 g, 10.61 mmol) portion wise. The mixture was stirred at rt for 90 min, acidified with 3 M HCl (4 mL) and stirred further 15 min. The reaction mixture was added to saturated NaHCO$_3$ solution (200 mL) and extracted 5× with DCM. The combined organic phases were dried over Na$_2$SO$_4$ and the solvents were evaporated in vacuo. The resulting N-methyl-N-Boc-N'-Tmob-ethylenediamine 1a was dried in high vacuum and used in the next reaction step without further purification.

Yield: 3.76 g (11.48 mmol, 89% purity, 1a: double Tmob protected product=8:1)

MS: m/z 355.22=[M+H]$^+$, (calculated monoisotopic mass=354.21).

To a solution of 1a (2 g, 5.65 mmol) in DCM (24 mL) COMU (4.84 g, 11.3 mmol), N-Fmoc-N-Me-Asp(OBn)-OH (2.08 g, 4.52 mmol) and 2,4,6-collidine (2.65 mL, 20.34 mmol) were added. The reaction mixture was stirred for 3 h at rt, diluted with DCM (250 mL) and washed 3× with 0.1 M H$_2$SO$_4$ (100 mL) and 3× with brine (100 mL). The aqueous phases were re-extracted with DCM (100 mL). The combined organic phases were dried over Na$_2$SO$_4$, filtrated and the residue concentrated to a volume of 24 mL. 1b was purified using flash chromatography.

Yield: 5.31 g (148%, 6.66 mmol)

MS: m/z 796.38=[M+H]$^+$, (calculated monoisotopic mass=795.37).

To a solution of 1b (5.31 g, max. 4.52 mmol ref. to N-Fmoc-N-Me-Asp(OBn)-OH) in THF (60 mL) DBU (1.8 mL, 3% v/v) was added. The solution was stirred for 12 min at rt, diluted with DCM (400 mL) and washed 3× with 0.1 M H$_2$SO$_4$ (150 mL) and 3× with brine (150 mL). The aqueous phases were re-extracted with DCM (100 mL). The combined organic phases were dried over Na$_2$SO$_4$ and filtrated. 1c was isolated upon evaporation of the solvent and used in the next reaction without further purification.

MS: m/z 574.31=[M+H]$^+$, (calculated monoisotopic mass=573.30). 1c (5.31 g, 4.52 mmol, crude) was dissolved in acetonitrile (26 mL) and COMU (3.87 g, 9.04 mmol), 6-tritylmercaptohexanoic acid (2.12 g, 5.42 mmol) and 2,4,6-collidine (2.35 mL, 18.08 mmol) were added. The reaction mixture was stirred for 4 h at rt, diluted with DCM (400 mL) and washed 3× with 0.1 M H$_2$SO$_4$ (100 mL) and 3× with brine (100 mL). The aqueous phases were re-extracted with DCM (100 mL). The combined organic phases were dried over Na$_2$SO$_4$, filtered and 1d was isolated upon evaporation of the solvent. Product 1d was purified using flash chromatography.

Yield: 2.63 g (62%, 94% purity)

MS: m/z 856.41=[M+H]$^+$, (calculated monoisotopic mass=855.41).

To a solution of 1d (2.63 g, 2.78 mmol) in i-PrOH (33 mL) and H$_2$O (11 mL) was added LiOH (267 mg, 11.12 mmol) and the reaction mixture was stirred for 70 min at rt. The mixture was diluted with DCM (200 mL) and washed 3× with 0.1 M H$_2$SO$_4$ (50 mL) and 3× with brine (50 mL). The aqueous phases were re-extracted with DCM (100 mL). The combined organic phases were dried over Na$_2$SO$_4$, filtered and 1e was isolated upon evaporation of the solvent. 1e was purified using flash chromatography.

Yield: 2.1 g (88%)

MS: m/z 878.4=[M+Na]$^+$, (calculated monoisotopic mass=837.40).

To a solution of 1e (170 mg, 0.198 mmol) in anhydrous DCM (4 mL) were added DCC (123 mg, 0.59 mmol), and a catalytic amount of DMAP. After 5 min, N-hydroxysuccinimide (114 mg, 0.99 mmol) was added and the reaction mixture was stirred at rt for 1 h. The reaction mixture was filtered, the solvent was removed in vacuo and the residue was taken up in 90% acetonitrile plus 0.1% TFA (3.4 mL). The crude mixture was purified by RP-HPLC. Product fractions were neutralized with 0.5 M pH 7.4 phosphate buffer and concentrated. The remaining aqueous phase was extracted with DCM and 1f was isolated upon evaporation of the solvent.

Yield: 154 mg (81%)

MS: m/z 953.4=[M+H]$^+$, (calculated monoisotopic mass=952.43)

Example 2

Synthesis of Linker Reagent 2 g

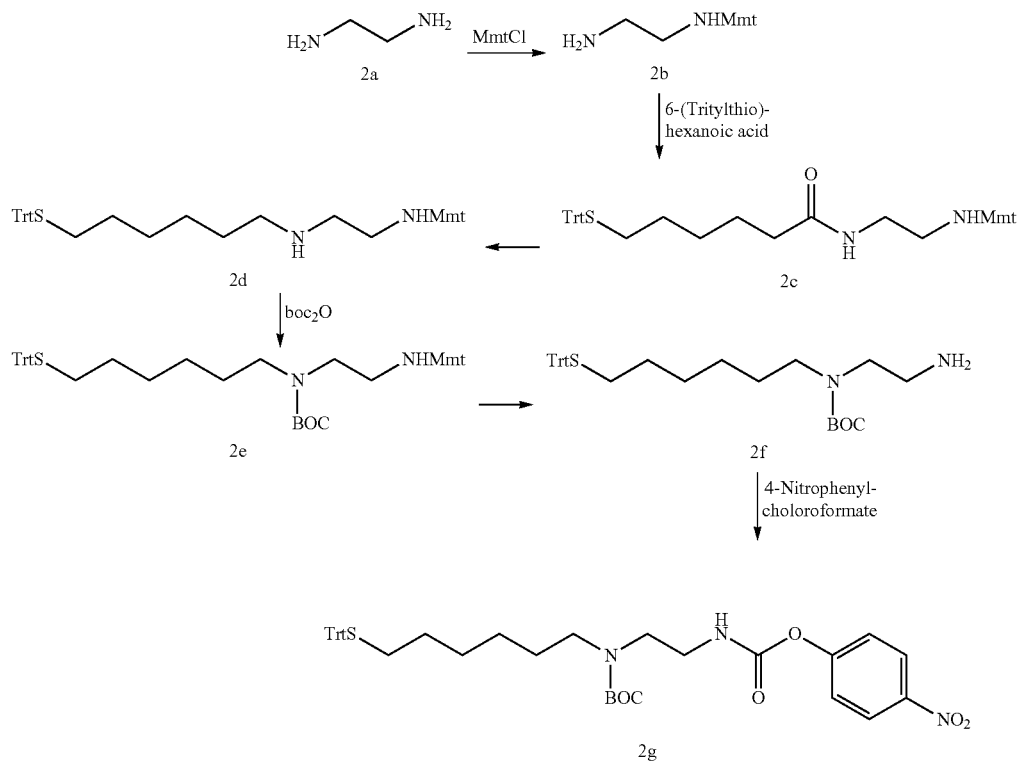

4-Methoxytriphenylmethyl chloride (3.00 g, 9.71 mmol) was dissolved in DCM (20 mL) and added dropwise under stirring to a solution of ethylenediamine 2a (6.5 mL, 97.3 mmol) in DCM (20 mL). The reaction mixture was stirred for 2 h at rt after which it was diluted with diethyl ether (300 mL), washed 3× with brine/0.1 M NaOH 30/1 (v/v) and once with brine. The organic phase was dried over Na$_2$SO$_4$ and 2b was isolated upon evaporation of the solvent.

Yield: 3.18 g (98%)

Mmt protected intermediate 2b (3.18 g, 9.56 mmol) was dissolved in DCM (30 mL). 6-(Tritylthio)-hexanoic acid (4.48 g, 11.5 mmol), PyBOP (5.67 g, 10.9 mmol) and DIPEA (5.0 mL, 28.6 mmol) were added and the mixture was stirred for 30 min at rt. The solution was diuted with diethyl ether (250 mL), washed 3× with brine/0.1 M NaOH 30/1 (v/v) and once with brine. The organic phase was dried over Na$_2$SO$_4$ and the solvent was removed in vacuo. 2c was purified using flash chromatography.

Yield: 5.69 g (85%)

MS: m/z 705.4=[M+H]$^+$, (calculated monoisotopic mass=704.34).

Compound 2c (3.19 g, 4.53 mmol) was dissolved in abhydrous THF (50 mL), 1 M BH$_3$.THF solution in THF (8.5 mL, 8.5 mmol) was added and the mixture was stirred for 16 h at rt. More 1 M BH$_3$.THF solution in THF (14 mL, 14.0 mmol) was added and the mixture was stirred for further 16 h at rt. Methanol (8.5 mL) and N,N'-dimethylethylenediamine (3.00 mL, 27.9 mmol) were added and the mixture was heated under reflux for 3 h. The mixture was allowed to cool down and ethyl acetate (300 mL) was added. The solution was washed 2× with aqueous Na$_2$CO$_3$ and 2× with aqueous NaHCO$_3$. The organic phase was dried over Na$_2$SO$_4$ and the solvent was removed in vacuo to obtain 2d.

Yield: 3.22 g (103%)

MS: m/z 691.4=[M+H]$^+$, (calculated monoisotopic mass=690.36).

Di-tert-butyl dicarbonate (2.32 g, 10.6 mmol) and DIPEA (3.09 mL, 17.7 mmol) were dissolved in DCM (5 mL) and added to a solution of 2d (2.45 g, 3.55 mmol) in DCM (5 mL). The mixture was stirred for 30 min at rt. The solution was concentrated in vacuo and purified by flash chromatography to obtain product 2e.

Yield: 2.09 g (74%)

MS: m/z 791.4=[M+H]$^+$, (calculated monoisotopic mass=790.42).

Compound 2e (5.01 g, 6.34 mmol) was dissolved in acetonitrile (80 mL). 0.4 M aqueous HCl (80 mL) followed by acetonitrile (20 mL) was added and the mixture was stirred for 1 h at rt. The pH was adjusted to pH 5.5 by addition of aqueous 5 M NaOH. The organic solvent was removed in vacuo and the remaining aqueous solution was extracted 4× with DCM. The combined organic phases were dried over $Na_2SO_4$ and the solvent was removed in vacuo to obtain product 2f.

Yield: 4.77 g (95%)

MS: m/z 519.3=$[M+H]^+$, (calculated monoisotopic mass=518.30).

Compound 2f (5.27 g, 6.65 mmol) was dissolved in DCM (30 mL) and added to a solution of p-nitrophenyl chloroformate (2.01 g, 9.98 mmol) in DCM (25 mL). 2,4,6-trimethylpyridine (4.38 mL, 33.3 mmol) was added and the solution was stirred for 45 min at rt. The solution was concentrated in vacu and purified by flash chromatography to obtain product 2 g.

Yield: 4.04 g (89%)

MS: m/z 706.32=$[M+Na]^+$, (calculated monoisotopic mass=683.30).

Example 3

Synthesis of Permanent S1 PTH(1-34) Conjugate 3

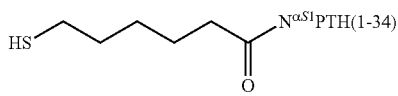

Side chain protected PTH(1-34) on TCP resin having Fmoc protected N-terminus was Fmoc deprotected according to the procedure given in Materials and Methods. A solution of 6-tritylmercaptohexanoic acid (62.5 mg, 160 µmol), PyBOP (80.1 mg, 154 µmol) and DIPEA (53 µL, 306 µmol) in DMF (2 mL) was added to 0.21 g (51 µmol) of the resin. The suspension was agitated for 80 min at rt. The resin was washed 10× with DMF, 10× with DCM and dried in vacuo. Cleavage of the peptide from the resin and removal of protecting groups was achieved by adding 10 mL cleavage cocktail 100/3/3/2/1 (v/w/v/v/v) TFA/DTT/TES/water/thioanisole and agitating the suspension for 1 h at rt. Crude 3 was precipitated in pre-cooled diethyl ether (−18° C.). The precipitate was dissolved in ACN/water and purified by RP-HPLC. The product fractions were freeze-dried.

Yield: 36 mg (14%), 3*8 TFA

MS: m/z 1062.31=$[M+4H]^{4+}$, (calculated monoisotopic mass for $[M+4H]^{4+}$=1062.30).

Example 4

Synthesis of Permanent K26 PTH(1-34) Conjugate 4

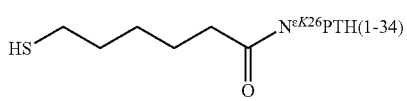

Side chain protected PTH(1-34) on TCP resin having Boc protected N-terminus and ivDde protected side chain of Lys26 was ivDde deprotected according to the procedure given in Materials and Methods. A solution of 6-tritylmercaptohexanoic acid (107 mg, 273 µmol), PyBOP (141 mg, 273 µmol) and DIPEA (95 µL, 545 µmol) in DMF (3 mL) was added to 0.80 g (90.9 µmol) of the resin. The suspension was agitated for 1 h at rt. The resin was washed 10× with DMF, 10× with DCM and dried in vacuo. Cleavage of the peptide from the resin and removal of protecting groups was achieved by adding 6 mL cleavage cocktail 100/3/3/2/1 (v/w/v/v/v) TFA/DTT/TES/water/thioanisole and agitating the suspension for 1 h at rt. Crude 4 was precipitated in pre-cooled diethyl ether (−18° C.). The precipitate was dissolved in ACN/water and purified by RP-HPLC. The product fractions were freeze-dried.

Yield: 40 mg (8%), 4*8 TFA

MS: m/z 1062.30=$[M+4H]^{4+}$, (calculated monoisotopic mass for $[M+4H]^{4+}$=1062.30).

Example 5

Synthesis of Transient S1 PTH(1-34) Conjugate

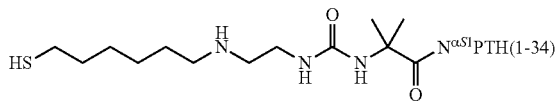

Side chain protected PTH(1-34) on TCP resin having Fmoc protected N-terminus was Fmoc deprotected according to the procedure given in Materials and Methods. A solution of Fmoc-Aib-OH (79 mg, 244 µmol), PyBOP (127 mg, 244 µmol) and DIPEA (64 µL, 365 µmol) in DMF (1.5 mL) was added to 0.60 g (61 µmol) of the resin. The suspension was agitated for 16 h at rt. The resin was washed 10× with DMF and Fmoc-deprotected as described above. A solution of 2 g (167 mg, 244 µmol) and DIPEA (64 µL, 365 µmol) in DMF (1.5 mL) was added to the resin. The suspension was agitated for 24 h at rt. The resin was washed 10× with DMF, 10× with DCM and dried in vacuo. Cleavage of the peptide from the resin and removal of protecting groups was achieved by adding 7 mL cleavage cocktail 100/3/3/2/1 (v/w/v/v/v) TFA/DTT/TES/water/thioanisole and agitating the suspension for 1 h at rt. Crude 5 was precipitated in pre-cooled diethyl ether (−18° C.). The precipitate was dissolved in ACN/water and purified by RP-HPLC. The product fractions were freeze-dried.

Yield: 78 mg (24%), 5*9 TFA

MS: m/z 1101.59=$[M+4H]^{4+}$, (calculated monoisotopic mass for $[M+4H]^{4+}$=1101.57).

Example 6

Synthesis of Transient S1 PTH(1-34) Conjugate 6

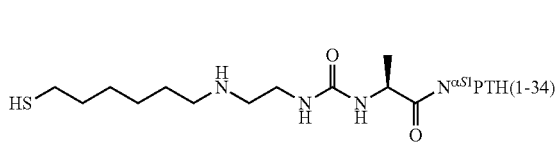

Side chain protected PTH(1-34) on TCP resin having Fmoc protected N-terminus was Fmoc deprotected according to the procedure given in Materials and Methods. A solution of Fmoc-Ala-OH (32 mg, 102 µmol), PyBOP (53 mg, 102 µmol) and DIPEA (27 µL, 152 µmol) in DMF (3 mL) was added to 0.25 g (25 µmol) of the resin. The suspension was shaken for 1 h at rt. The resin was washed 10× with DMF, 10× with DCM and dried under vacuum.

Fmoc-deprotection was performed as described above. A solution of 2 g (69 mg, 102 µmol) and DIPEA (27 µL, 152 µmol) in DMF (3 mL) was added to the resin. The suspension was agitated for 1.5 h at rt. The resin was washed 10× with DMF, 10× with DCM and dried in vacuo. Cleavage of the peptide from the resin and removal of protecting groups was achieved by adding 3 mL cleavage cocktail 100/3/3/2/1 (v/w/v/v/v) TFA/DTT/TES/water/thioanisole and agitating the suspension for 1 h at rt. Crude 6 was precipitated in pre-cooled diethyl ether (−18° C.). The precipitate was dissolved in ACN/water and purified by RP-HPLC. The product fractions were freeze-dried.

Yield: 25 mg (18%), 6*9 TFA

MS: m/z 1098.75=[M+4H]$^{4+}$, (calculated monoisotopic mass for [M+4H]$^{4+}$=1098.07).

Example 7

Synthesis of Transient S1 PTH(1-34) Conjugate 7

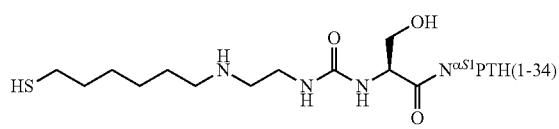

7

Side chain protected PTH(1-34) on TCP resin having Fmoc protected N-terminus was Fmoc deprotected according to the procedure given in Materials and Methods. A solution of Fmoc-Ser(Trt)-OH (117 mg, 205 µmol), PyBOP (108 mg, 207 µmol) and DIPEA (53 µL, 305 µmol) in DMF (2 mL) was added to 0.50 g (51 µmol) of the resin. The suspension was agitated for 1 h at rt. The resin was washed 10× with DMF, 10× with DCM and dried under vacuum.

Fmoc-deprotection was performed as described above. A solution of 2 g (144 mg, 211 µmol) and DIPEA (53 µL, 305 µmol) in DMF (1.8 mL) was added to the resin. The suspension was shaken for 7 h at rt. The resin was washed 10× with DMF, 10× with DCM and dried in vacuo. Cleavage of the peptide from the resin and removal of protecting groups was achieved by adding 6 mL cleavage cocktail 100/3/3/2/1 (v/w/v/v/v) TFA/DTT/TES/water/thioanisole and agitating the suspension for 1 h at rt. Crude 7 was precipitated in pre-cooled diethyl ether (−18° C.). The precipitate was dissolved in ACN/water and purified by RP-HPLC. The product fractions were freeze-dried.

Yield: 54 mg (20%), 7*9 TFA

MS: m/z 1102.08=[M+4H]$^{4+}$, (calculated monoisotopic mass for [M+4H]$^{4+}$=1102.07).

Example 8

Synthesis of Transient S1 PTH(1-34) Conjugate 8

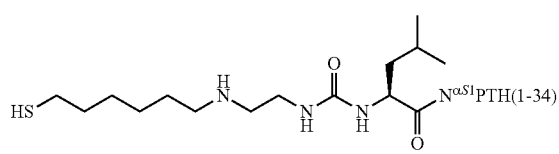

8

Side chain protected PTH(1-34) on TCP resin having Fmoc protected N-terminus was Fmoc deprotected according to the procedure given in Materials and Methods. A solution of Fmoc-Leu-OH (36 mg, 102 µmol), PyBOP (53 mg, 102 µmol) and DIPEA (27 µL, 152 µmol) in DMF (3 mL) was added to 0.25 g (25 µmol) of the resin. The suspension was agitated for 1 h at rt. The resin was washed 10× with DMF, 10× with DCM and dried under vacuum.

Fmoc-deprotection was performed as described above. A solution of 2 g (69 mg, 102 µmol) and DIPEA (27 µL, 152 µmol) in DMF (3 mL) was added to the resin. The suspension was agitated for 1.5 h at rt. The resin was washed 10× with DMF, 10× with DCM and dried in vacuo. Cleavage of the peptide from the resin and removal of protecting groups was achieved by adding 3 mL cleavage cocktail 100/3/3/2/1 (v/w/v/v/v) TFA/DTT/TES/water/thioanisole and agitating the suspension for 1 h at rt. Crude 8 was precipitated in pre-cooled diethyl ether (−18° C.). The precipitate was dissolved in ACN/water and purified by RP-HPLC. The product fractions were freeze-dried.

Yield: 31 mg (22%), 8*9 TFA

MS: m/z 1109.32=[M+4H]$^{4+}$, (calculated monoisotopic mass for [M+4H]$^{4+}$=1108.58).

Example 9

Synthesis of Transient S1 PTH(1-34) Conjugate 9

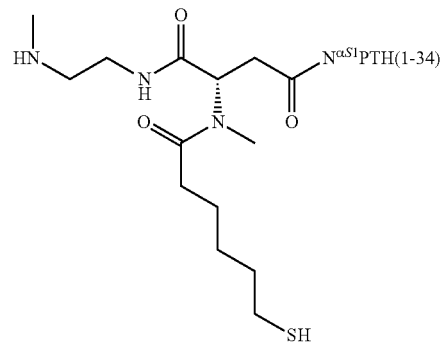

9

Side chain protected PTH(1-34) on TCP resin having Fmoc protected N-terminus was Fmoc deprotected according to the procedure given in Materials and Methods. A solution of 1e (182 mg, 213 µmol), PyBOP (111 mg, 213 µmol) and DIPEA (93 µL, 532 µmol) in DMF (5 mL) was added to 2.00 g (107 µmol) of the resin. The suspension was agitated for 16 h at rt. The resin was washed 10× with DMF, 10× with DCM and dried under vacuum. Cleavage of the peptide from the resin and removal of protecting groups was achieved by adding 20 mL cleavage cocktail 100/3/3/2/1 (v/w/v/v/v) TFA/DTT/TES/water/thioanisole and agitating the suspension for 1 h at rt. Crude 9 was precipitated in pre-cooled diethyl ether (−18° C.). The precipitate was dissolved in ACN/water and purified by RP-HPLC. The product fractions were freeze-dried.

Yield: 47 mg (8%), 9*9 TFA

MS: m/z 1108.58=[M+4H]$^{4+}$, (calculated monoisotopic mass for [M+4H]$^{4+}$=1108.57).

Example 10

Synthesis of Transient K26 PTH(1-34) Conjugate 10

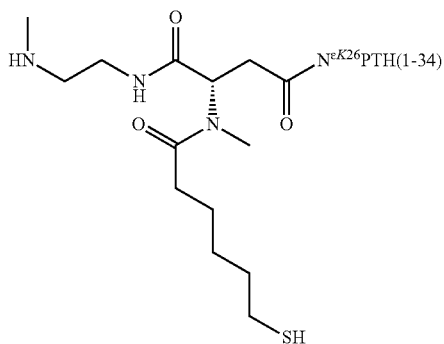

Side chain protected PTH(1-34) on TCP resin having Boc protected N-terminus and ivDde protected side chain of Lys26 was ivDde deprotected according to the procedure given in Materials and Methods. A solution of 1f (867 mg, 910 μmol) and DIPEA (0.24 mL, 1.36 mmol) in DMF (5 mL) was added to 1.91 g (227 μmol) of the resin. The suspension was agitated for 1 h at rt. The resin was washed 10× with DMF, 10× with DCM and dried under vacuum. Cleavage of the peptide from the resin and removal of protecting groups was achieved by adding 20 mL cleavage cocktail 100/3/3/2/1 (v/w/v/v/v) TFA/DTT/TES/water/thioanisole and shaking the suspension for 1 h at rt. Crude 10 was precipitated in pre-cooled diethyl ether (−18° C.). The precipitate was dissolved in ACN/water and purified by RP-HPLC. The product fractions were freeze-dried.

Yield: 92 mg (7%), 10*9 TFA

MS: m/z 1108.58=[M+4H]$^{4+}$, (calculated monoisotopic mass for [M+4H]$^{4+}$=1108.57).

Example 11

Synthesis of Low Molecular Weight Transient 51 PEG Conjugate 11b

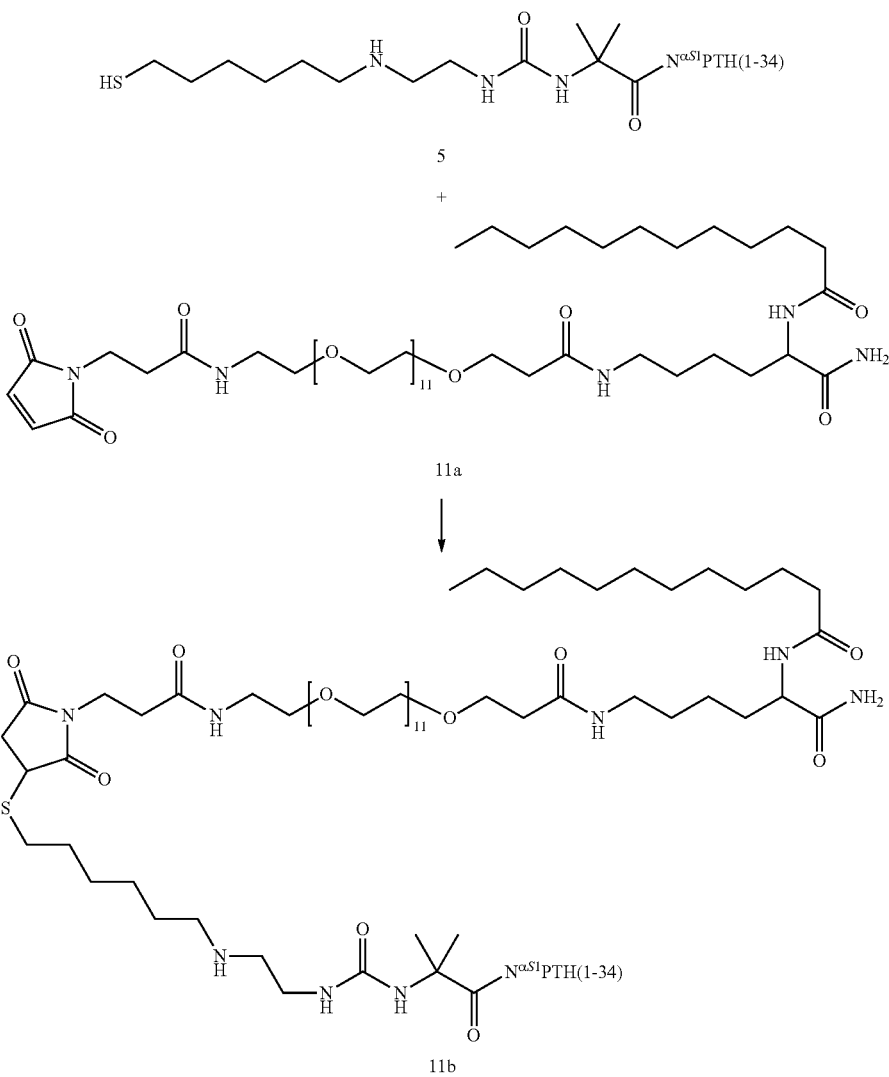

0.15 mL of a 0.5 M NaH$_2$PO$_4$ buffer (pH 7.4) was added to 0.5 mL of a 20 mg/mL solution of thiol 5 (10 mg, 1.84 μmol) in 1/1 (v/v) acetonitrile/water containing 0.1% TFA (v/v). The solution was incubated at rt for 10 min after which 238 μL of a 10 mg/mL solution of maleimide 11a (2.4 mg, 2.21 μmol) in 1/1 (v/v) acetonitrile/water containing 0.1% TFA (v/v) were added. The solution was incubated for 20 min at rt. 10 μL TFA was added and the mixture was purified by RP-HPLC. The product fractions were freeze-dried to obtain 11b.

Yield: 3.1 mg (26%), 11b*9 TFA

MS: m/z 1097.00=[M+4H]$^{4+}$, (calculated monoisotopic mass for [M+5H]$^{5+}$=1096.99).

Example 12

Synthesis of Low Molecular Weight Transient S1 PEG Conjugate 12

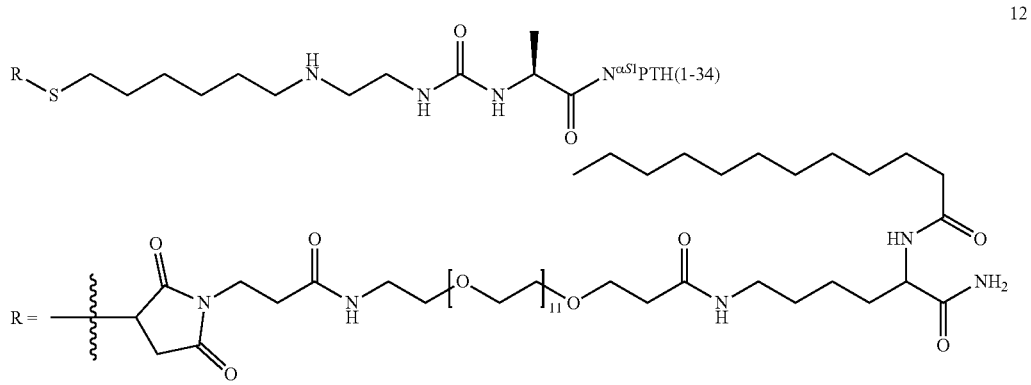

12

Conjugate 12 was synthesized as described for 11b by using thiol 6 (10 mg, 1.85 μmol) and maleimide 11a (2.4 mg, 2.21 μmol).

Yield: 10 mg (83%), 12*9 TFA

MS: m/z 1094.20=[M+4H]$^{4+}$, (calculated monoisotopic mass for [M+4H]$^{4+}$=1094.19).

Example 13

Synthesis of Low Molecular Wight Tansient 51 PEG Cnjugate 13

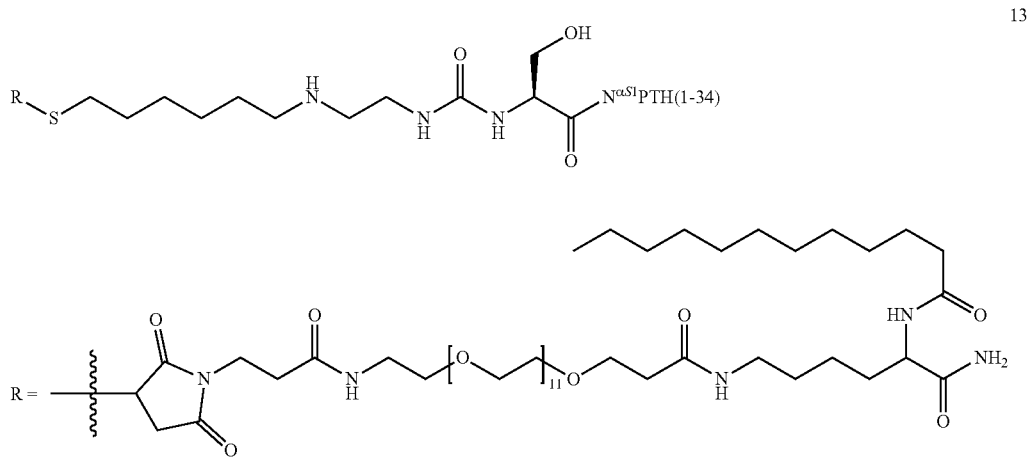

13

Conjugate 13 was synthesized as described for 11b by using thiol 7 (10 mg, 1.84 µmol) and maleimide 11a (2.4 mg, 2.21 µmol).

Yield: 8 mg (67%), 13*9 TFA

MS: m/z 1097.40=[M+5H]$^{5+}$, (calculated monoisotopic mass for [M+5H]$^{5+}$=1097.39).

Example 14

Synthesis of Low Molecular Weight Transient S1 PEG Conjugate 14

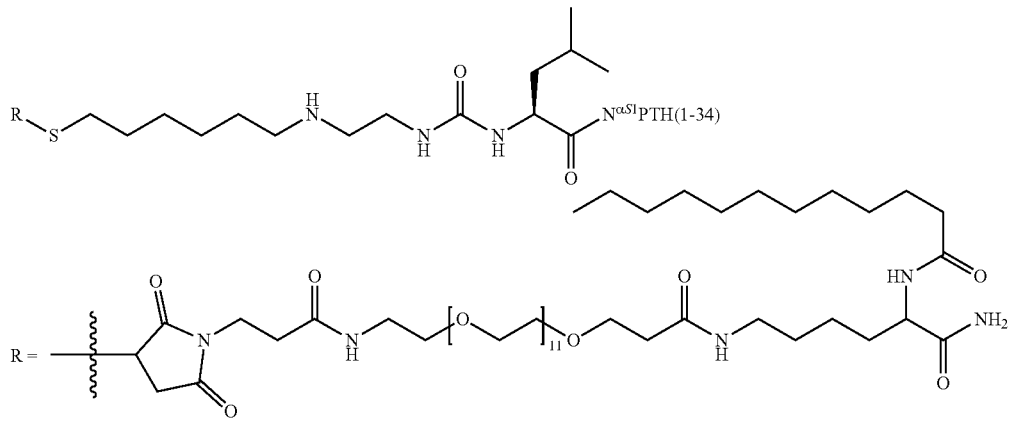

14

Conjugate 14 was synthesized as described for 11b by using thiol 8 (10 mg, 1.83 µmol) and maleimide 11a (2.4 mg, 2.21 µmol).

Yield: 4 mg (33%), 14*9 TFA m/z 1378.01=[M+4H]$^{4+}$, (calculated monoisotopic mass for [M+4H]$^{4+}$=1378.00).

Example 15

Synthesis of Low Molecular Weight Transient K26 PEG Conjugate 15

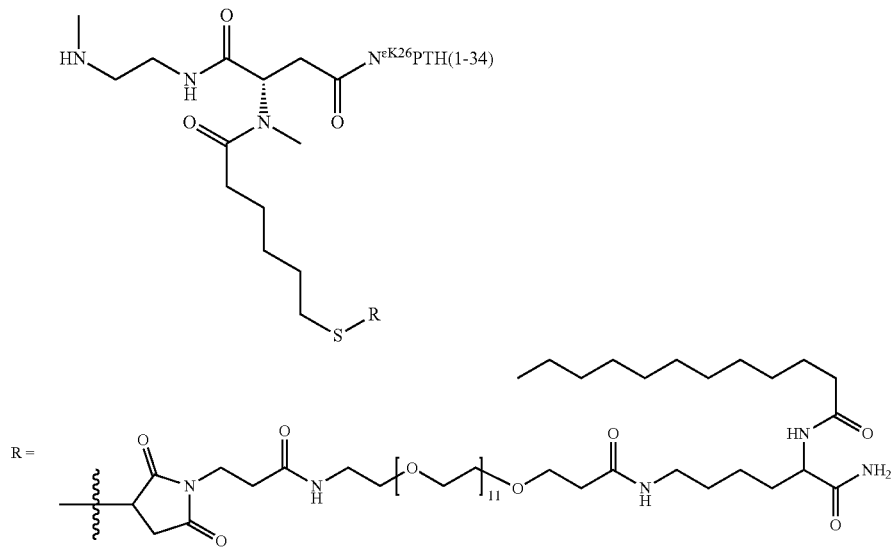

15

Conjugate 15 was synthesized as described for 11b by using thiol 10 (5.2 mg, 0.95 µmol) and maleimide 11a (1.23 mg, 1.14 µmol).

Yield: 2.1 mg (33%), 15*9 TFA

MS: m/z 1102.60=[M+5H]$^{5+}$, (calculated monoisotopic mass for [M+5H]$^{5+}$=1102.59).

Example 16

Synthesis of Permanent 2×20 kDa S1 PEG Conjugate 16

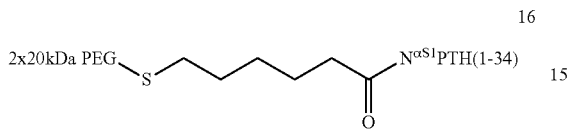

772 µL of a solution containing thiol 3 (19.4 mg/mL, 15 mg, 3.54 µmol) and 2.5 mg/mL Boc-L-Met in 1/1 (v/v) acetonitrile/water containing 0.1% TFA (v/v) were added to 1.87 mL of a solution containing PEG 2×20 kDa maleimide (Sunbright GL2-400MA, 187 mg, 4.32 µmol) and 2.5 mg/mL Boc-L-Met in water containing 0.1% TFA (v/v). 0.5 M NaH$_2$PO$_4$ buffer (0.66 mL, pH 7.0) was added and the mixture was stirred for 30 min at rt. 10 µL of a 270 mg/mL solution of 2-mercaptoethanol in water was added. The mixture was stirred for 5 min at rt and 0.33 mL 1 M HCl were added. Conjugate 16 was purified by IEX followed by RP-HPLC using a linear gradient of solvent system A (water containing 0.1% AcOH v/v) and solvent system B (acetonitrile containing 0.1% AcOH v/v). The product containing fractions were freeze-dried.

Yield: 97 mg (2.01 µmol, 57%) conjugate 16*8 AcOH

Example 17

Synthesis of Permanent 2×20 kDa K26 PEG Conjugate 17

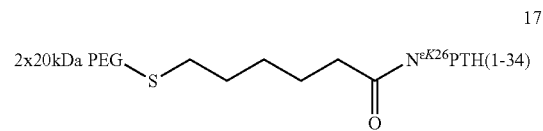

Conjugate 17 was prepared as described for 16 by reaction of thiol 4 (15 mg, 3.53 µmol) and PEG 2×20 kDa maleimide (Sunbright GL2-400MA, 187 mg, 4.32 µmol).

Yield: 80 mg (1.79 µmol, 51%) conjugate 17*8 AcOH

Example 18

Synthesis of Transient 2×20 kDa 51 PEG Conjugate 18

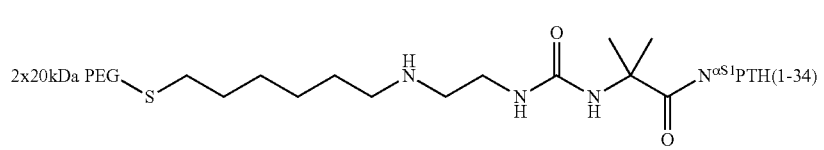

Conjugate 18 was prepared as described for 16 by reaction of thiol 5 (37 mg, 8.40 µmol) and PEG 2×20 kDa maleimide (Sunbright GL2-400MA, 445 mg, 9.24 µmol). The reaction was quenched by addition of 50 µL TFA without prior addition of 2-mercaptoethanol. Conjugate 18 was purified by IEX followed by SEC for desalting. The product containing fractions were freeze-dried.

Yield: 161 mg (3.33 µmol, 40%) conjugate 18*9 AcOH

Example 19

Synthesis of Transient 2×20 kDa 51 PEG Conjugate 19

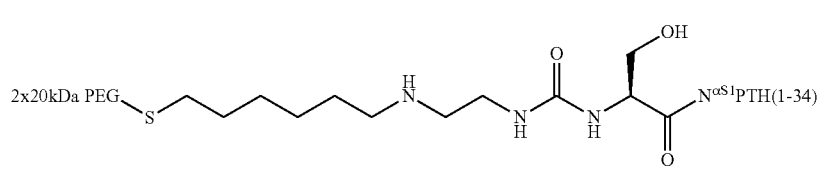

Conjugate 19 was prepared as described for 16 by reaction of thiol 7 (27 mg, 6.14 µmol) and PEG 2×20 kDa maleimide (Sunbright GL2-400MA, 325 mg, 7.50 mol).

Yield: 249 mg (5.16 µmol, 84%) conjugate 19*9 AcOH

Example 20

Synthesis of transient 2×20 kDa S1 PEG Conjugate 20

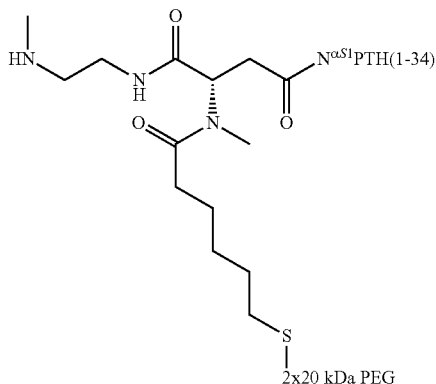

Conjugate 20 was prepared as described for 16 by reaction of thiol 9 (38 mg, 8.59 µmol) and PEG 2×20 kDa maleimide (Sunbright GL2-400MA, 455 mg, 9.45 µmol). The reaction was quenched by addition of 50 µL TFA without prior addition of 2-mercaptoethanol. Conjugate 20 was purified by IEX followed by SEC for desalting. The product containing fractions were freeze-dried.

Yield: 194 mg (4.01 µmol, 47%) conjugate 20*9 AcOH

Example 21

Synthesis of Transient 2×20 kDa K26 PEG Conjugate 21

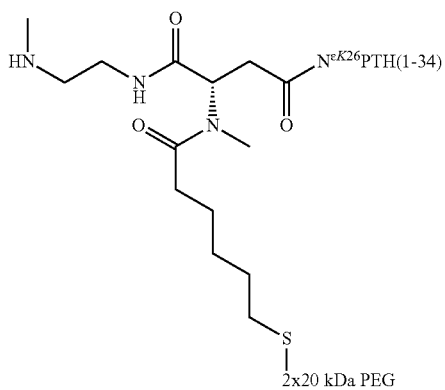

Conjugate 21 was prepared as described for 16 by reaction of thiol 10 (34 mg, 7.58 µmol) and PEG 2×20 kDa maleimide (Sunbright GL2-400MA, 401 mg, 9.26 µmol).

Yield: 256 mg (5.30 µmol, 70%) conjugate 21*9 AcOH

Example 22

Pharmacodynamic Actions in Thyroparathyroidectomised (TPTx) Rats During a 28-Days Study With Daily Subcutaneous Injections With Conjugate 18 or PTH(1-84)

This study was performed in order to test and compare the effect of daily subcutaneous injection of compound 18 and PTH(1-84), the current standard of care, in an animal disease model relevant for investigating treatment of hypoparathyroidism (HP). Rats subjected to thyroparathyroidectomy (TPTx) by blunt dissection are unable to produce parathyroid hormone, PTH, the major regulator of calcium homeostasis. Hence, TPTx rats develop hypocalcemia and hyperphosphatemia characteristic of HP. 17 weeks old female SD TPTx rats (n=9/group) were dosed subcutaneously for 28 days with compound 18 (5 µg PTH eq/kg/d; 1.2 nmol/kg/d, in 10 mM succinic acid, 46 g/L mannitol, pH 4.0), PTH(1-84) (70 µg PTH eq/kg/d; 7.3 nmol/kg/d; in 10 mM citrate, mannitol 39.0 g/L, pH 5.0) or vehicle. Additionally, one group of sham operated rats (n=9) representing normophysiological background control were also given vehicle. Serum calcium (sCa) and phosporous (sP) levels in the animals were measured pre- and post-dose on days 1, 6, 12 and 27. Moreover, bone turnover markers (P1NP and CTx) were measured and bone quality assessed by ex vivo pQCT.

Results: The average sCa in the TPTx rats pre-dosing at day 1 was 8.3 mg/dL compared to 10.9 mg/dL in the sham operated control rats. The sP values were 8.7 mg/dL and 5.9 mg/dL, respectively. Compound 18 given daily at 1.2 nmol/kg elevated sCa to near-normal levels while lowering sP within a few days of administration. At day 12 (day 5 at steady state with compound 18) sCa had stabilised at normal level (10.7 mg/dL) in this group of animals (compound 18/sham-control ratio=1.01) as opposed to the hypocalceamic level (8.1 mg/dL) measured in the PTH(1-84) treated rats (PTH(1-84)/sham-control ratio=0.76). Additionally, the 24-hour urinary Ca excretion at day 12 was comparable between the animals treated with compound 18 and sham-control. Bone mineral density (BMD) and bone mineral content (BMC) were increased in TPTx controls as seen in HP patients. Treatment with Compound 18 decreased BMD, BMC and area in parallel with an increase in CTx compared to sham and vehicle-treated TPTx animals. A significant increase in trabecular BMD was observed in animals dosed with PTH(1-84) compared to both control groups.

It was concluded that compound 18 at a dosage even as low as less than 20% of the molar equivalent of the here tested dose of PTH(1-84) was able to maintain sCa at a level comparable to the sCa level in sham-control animals (here representing normal level) over a 24 hour period. In contrast, PTH(1-84) at a dose of 7.3 nmol/kg/d did not lead to increase in sCa as compared to the levels in the vehicle-injected TPTx rats. However, a minimal decrease in sP was observed in the PTH(1-84) dosed animals confirming exposure and response to PTH(1-84) in the rats. Following the 28-days of treatment with Compound 18, trabecular and cortical BMD in vertebrae were within normal range, whereas an anabolic effect was observed for PTH(1-84) on trabecular and cortical bone in vertebrae.

Abbreviations:
ACN acetonitrile
AcOH acetic acid
Aib 2-aminoisobutyric acid
BMD bone mineral density
Bn benzyl
Boc tert-butyloxycarbonyl
COMU (1-cyano-2-ethoxy-2-oxoethylidenaminooxy)dimethylamino-morpholino-carbenium hexafluorophosphate
cAMP cyclic adenosine monophosphate
d day
DBU 1,3-diazabicyclo[5.4.0]undecene
DCC N,N'-dicyclohexylcarbodiimide
DCM dichloromethane
DIPEA N,N-diisopropylethylamine
DMAP dimethylamino-pyridine
DMF N,N-dimethylformamide
DMSO dimethylsulfoxide DTT dithiothreitol
EDTA ethylenediaminetetraacetic acid
eq stoichiometric equivalent
ESI-MS electrospray ionization mass spectrometry
Et ethyl
Fmoc 9-fluorenylmethyloxycarbonyl
Glu-C endoproteinase Glu-C
h hour
HATU O-(7-azabenzotriazole-1-yl)-N,N,N',N'-tetramethyl-uronium hexafluorophosphate
HP hypoparathyroidism
HPLC high performance liquid chromatography
ivDde 4,4-dimethyl-2,6-dioxocyclohex-1-ylidene)-3-methylbutyl
LC liquid chromatography
LTQ linear trap quadrupole
Lys-C endoproteinase Lys-C
LLOQ lower limit of quantification
Mal 3-maleimido propyl
Me methyl
MeOH methanol
min minutes
Mmt monomethoxytrityl
MS mass spectrum/mass spectrometry
m/z mass-to-charge ratio
OtBu tert-butyloxy
PEG poly(ethylene glycol)
pH potentia Hydrogenii
PK pharmacokinetics
Pr propyl
PTH parathyroid hormone
PyBOP benzotriazol-1-yl-oxytripyrrolidinophosphonium hexafluorophosphate
Q-TOF quadrupole time-of-flight
RP-HPLC reversed-phase high performance liquid chromatography
rt room temperature
sCa serum calcium
SIM single ion monitoring
SEC size exclusion chromatography
sc subcutaneous
sP serum phosphate
$t_{1/2}$ half life
TCP tritylchloride polystyrol
TES triethylsilane
TFA trifluoroacetic acid
THF tetrahydrofuran
Tmob 2,4,6-trimethoxybenzyl
TPTx thyroparathyroidectomy
Trt triphenylmethyl, trityl
ULOQ upper limit of quantification
UPLC ultra performance liquid chromatography
UV ultraviolet
ZQ single quadrupole

---

The invention claimed is:

1. A method of treating or controlling hypoparathyroidism in a mammalian patient, comprising the step of administering a pharmaceutical composition comprising at least one controlled-release parathyroid hormone (PTH) compound or a pharmaceutically acceptable salt thereof by subcutaneous injection no more frequently than once every 24 hours with a dosage of the controlled-release PTH compound that corresponds to 20-40% of the molar equivalent dose of PTH 1-84 administered subcutaneously every 24 hours, which is required to maintain a serum albumin-adjusted calcium level in serum of above 8.5 mg/dL over a 24 hour period in humans and wherein the controlled release PTH compound is of formula:

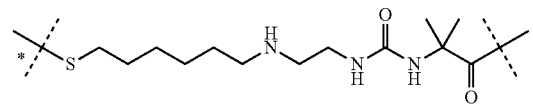

wherein the unmarked dashed line indicates the attachment to an N-terminal amine group of -D, which is a PTH moiety having the amino sequence of SEQ ID NO:51, by an amide bond; and the dashed line marked with the asterisk indicates attachment to a moiety

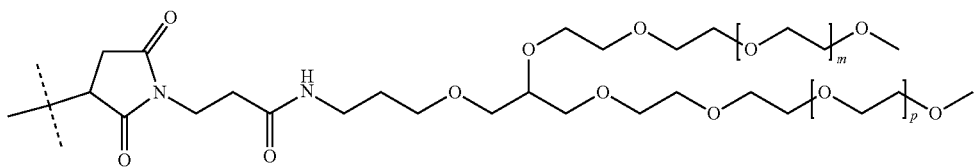

wherein each of m and p is independently an integer ranging from and including 400 to 500.

2. The method of claim 1, wherein the pharmaceutical composition is administered once every 24 hours.

3. The method of claim 1, wherein the pharmaceutical composition has a pH ranging from and including pH 3 to pH 8.

4. The method of claim 1, wherein the mammalian patient is a human patient.

5. The method of claim 1, wherein the dosage of the controlled-release PTH compound corresponds to no more than 30% of the molar equivalent dose of PTH 1-84.

* * * * *